United States Patent
Mizutani et al.

(10) Patent No.: US 7,601,146 B2
(45) Date of Patent: Oct. 13, 2009

(54) INTERLABIAL PAD INDIVIDUAL PACKAGING VESSEL

(75) Inventors: Satoshi Mizutani, Kagawa (JP); Koichi Yamaki, Kagawa (JP); Yuki Noda, Kagawa (JP); Megumi Tokumoto, Kagawa (JP); Akane Sakai, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 10/705,673

(22) Filed: Nov. 10, 2003

(65) Prior Publication Data

US 2004/0162539 A1 Aug. 19, 2004

Related U.S. Application Data

(63) Continuation of application No. PCT/JP02/04882, filed on May 21, 2002.

(30) Foreign Application Priority Data

May 22, 2001 (JP) .............................. 2001-152403
Jan. 24, 2002 (JP) .............................. 2002-016191

(51) Int. Cl.
*A61F 13/551* (2006.01)
*A61F 13/56* (2006.01)
*A61F 13/84* (2006.01)

(52) U.S. Cl. .............................. 604/385.17; 604/385.02; 604/385.03; 604/387; 604/385.01

(58) Field of Classification Search ......... 604/327–329, 604/346–347, 355, 385.03, 385.08–385.09, 604/385.14, 385.18–385.19, 387
See application file for complete search history.

(56) References Cited

U.S. PATENT DOCUMENTS

| | | | | |
|---|---|---|---|---|
| 1,587,280 A | * | 6/1926 | Burke | ...................... 229/87.08 |
| 4,556,146 A | | 12/1985 | Swanson et al. | |
| 4,595,392 A | | 6/1986 | Johnson et al. | |
| 4,595,932 A | | 6/1986 | Ruhl | |
| 4,677,697 A | * | 7/1987 | Hayes | ............................ 2/159 |
| 4,735,316 A | | 4/1988 | Froidh et al. | |

(Continued)

FOREIGN PATENT DOCUMENTS

CN 1268040 A 9/2000

(Continued)

OTHER PUBLICATIONS

Mizutani, et al., "Interlabial Pad", U.S. Appl. No. 10/705,780, filed Nov. 10, 2003.

(Continued)

*Primary Examiner*—Karin M Reichle
(74) *Attorney, Agent, or Firm*—Darby & Darby P.C.

(57) ABSTRACT

An interlabial pad individual wrapping container is presented which facilitates sanitary application and removal of an interlabial pad between the labia of a wearer. The interlabial individual wrapping container can be used as a preferred handling member at the time of application or removal of the interlabial pad. Two fingers of the left hand are inserted in finger insertion openings formed from a belt body attached on the wrapping container, the wrapping container is separated into the sections along a separation part by opening these fingers to the left and right, and in this state, the action for applying the interlabial pad held on a finger of the right hand is performed.

4 Claims, 40 Drawing Sheets

U.S. PATENT DOCUMENTS

| | | | |
|---|---|---|---|
| 5,025,503 A * | 6/1991 | O'Brien | 2/163 |
| 5,839,648 A * | 11/1998 | Brigand et al. | 229/87.05 |
| D404,814 S | 1/1999 | Mayer | |
| 5,868,727 A | 2/1999 | Barr et al. | |
| 5,891,126 A | 4/1999 | Osborn, III et al. | |
| 5,916,205 A | 6/1999 | Olson et al. | |
| 6,036,679 A * | 3/2000 | Balzar et al. | 604/378 |
| 6,131,575 A | 10/2000 | Lenker et al. | |
| 6,131,736 A | 10/2000 | Farris et al. | |
| 6,183,457 B1 | 2/2001 | Kuhn et al. | |
| 6,309,104 B1 * | 10/2001 | Koch et al. | 383/200 |
| 6,687,911 B2 * | 2/2004 | Fitz | 2/21 |
| 6,698,928 B2 * | 3/2004 | Miller | 383/205 |
| 6,918,392 B2 * | 7/2005 | Kassman | 128/844 |
| 2001/0049838 A1 | 12/2001 | Fitz | |

FOREIGN PATENT DOCUMENTS

| | | |
|---|---|---|
| EP | 0888764 | 1/1999 |
| FR | 2703244 | 10/1994 |
| JP | 493722 | 1/1974 |
| JP | 61108258 | 7/1986 |
| JP | S61164974 | 7/1986 |
| JP | 61-232845 A1 | 10/1986 |
| JP | 62-9450 A1 | 1/1987 |
| JP | 63260556 | 10/1988 |
| JP | S63154023 U | 10/1988 |
| JP | 0356366 | 3/1991 |
| JP | 05237151 | 9/1993 |
| JP | 05293138 | 11/1993 |
| JP | 6-506368 A1 | 7/1994 |
| JP | 0640203 | 10/1994 |
| JP | 7-96001 A1 | 4/1995 |
| JP | H07323045 A | 12/1995 |
| JP | 8-47506 A1 | 2/1996 |
| JP | 08-215242 A1 | 8/1996 |
| JP | 10-127688 A1 | 5/1998 |
| JP | 11-104167 A1 | 4/1999 |
| JP | 2000-051267 | 12/1999 |
| JP | 2001087306 | 4/2001 |
| JP | 2001-509402 | 7/2001 |
| JP | 2002-513633 A1 | 5/2002 |
| JP | 02534163 | 10/2002 |
| TW | 247431 A1 | 5/1995 |
| TW | 294591 A1 | 1/1997 |
| TW | 338315 A1 | 8/1998 |
| TW | 386060 A1 | 4/2000 |
| TW | 386872 A1 | 4/2000 |
| TW | 394681 A1 | 6/2000 |
| TW | 416847 A1 | 1/2001 |
| TW | 442278 A1 | 6/2001 |
| TW | 450802 A1 | 8/2001 |
| TW | 454503 A1 | 9/2001 |
| TW | 470640 A1 | 1/2002 |
| TW | 524677 A1 | 3/2003 |
| WO | 92/11825 | 7/1992 |
| WO | 9422405 | 10/1994 |
| WO | 9500094 A1 | 1/1995 |
| WO | 95/17148 A2 | 6/1995 |
| WO | 9602217 | 2/1996 |
| WO | 9901093 | 1/1999 |
| WO | WO-99/01096 A1 | 1/1999 |
| WO | WO-99/25295 A1 | 5/1999 |
| WO | WO-99/26574 A1 | 6/1999 |
| WO | WO-99/26575 A1 | 6/1999 |
| WO | 99/56681 | 11/1999 |
| WO | WO-99/56689 A1 | 11/1999 |
| WO | 0040192 | 7/2000 |
| WO | 0147458 A1 | 7/2001 |

OTHER PUBLICATIONS

Mizutani, et al, "Interlabial Pad and Package", U.S. Appl. No. 10/706,303, filed Nov. 10, 2003.

Mizutani, et al., "Interlabial Pad", U.S. Appl. No. 10/705,403, filed Nov. 10, 2003.

Mizutani, et al., "Interlabial Pad", U.S. Appl. No. 10/705,399, filed Nov. 10, 2003.

Mizutani, et al., "Interlabial Pad", U.S. Appl. No. 10/705,811, filed Nov. 10, 2003.

Mizutani, et al., "Interlabial Pad and Package Thereof", U.S. Appl. No. 10/705,400, filed Nov. 10, 2003.

Mizutani, et al., "Flap-Equipped Interlabial Pad", U.S. Appl. No. 10/705,670, filed Nov. 10, 2003.

Mizutani, et al., "Interlabial Pad Individual Packaging Vessel, and Individual Packaging Body", U.S. Appl. No. 10/705,781, filed Nov. 10, 2003.

Mizutani, Satoshi, "Interlabial Product Having Form for Finger Securement, and Individual Package", U.S. Appl. No. 10/705,779, filed Nov. 10, 2003.

Mizutani, et al., "Interlabial Pad", U.S. Appl. No. 10/705,778, filed Nov. 10, 2003.

Mizutani, et al., "Interlabial Pad Individual Packaging Body", U.S. Appl. No. 10/705,669, filed Nov. 10, 2003.

Mizutani, et al., "Interlabial Pad", U.S. Appl. No. 10/705,812, filed Nov. 10, 2003.

Mizutani, et al., "Individual Packaging Body and Outer Vessel Therefor", U.S. Appl. No. 10/705,402, filed Nov. 10, 2003.

Mizutani, et al., "Interlabial Pad", U.S. Appl. No. 10/705,407, filed Nov. 10, 2003.

Mizutani, et al., "Interlabial Pad and Package Thereof", U.S. Appl. No. 10/705,404, filed Nov. 10, 2003.

Mizutani, et al., "Interlabial Pad", U.S. Appl. No. 10/705,408, filed Nov. 10, 2003.

Mizutani, et al., "Interlabial Pad", U.S. Appl. No. 10/705,406, filed Nov. 10, 2003.

Mizutani, et al., "Interlabial Pad and Package Thereof", U.S. Appl. No. 10/705,810, filed Nov. 10, 2003.

Chinese Office Action dated Oct. 20, 2006 corresponding to Chinese Patent Application 200510072194.7.

* cited by examiner

FIG. 1
(A)
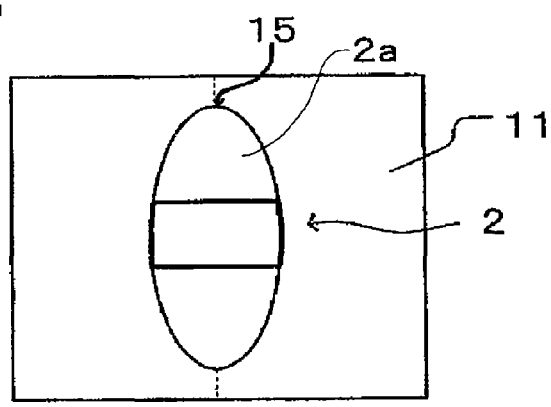
(B)
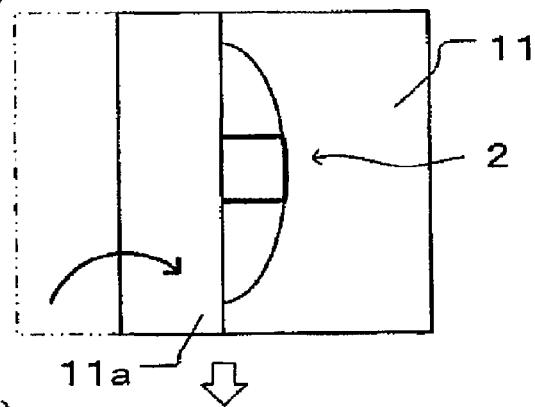
(C)
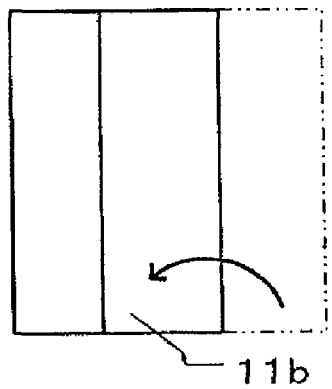
(D)
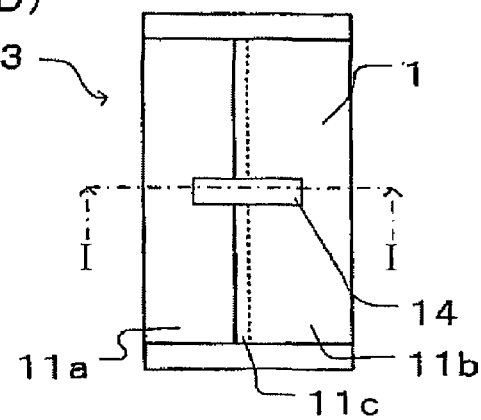

FIG. 5
(A)
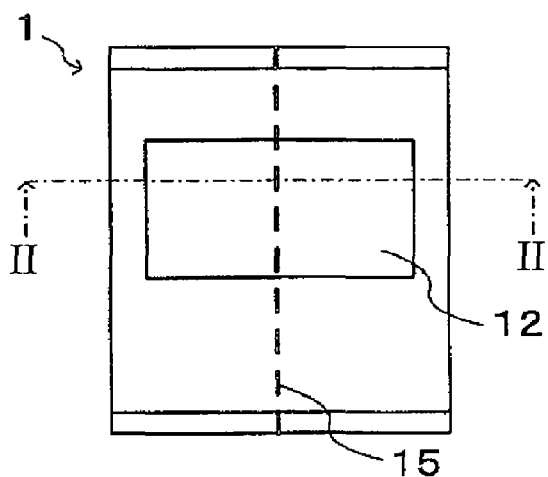
(B)
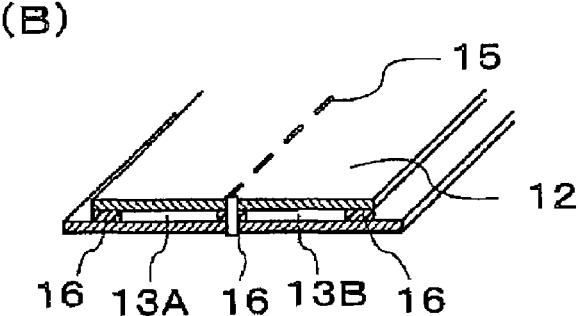
(C)
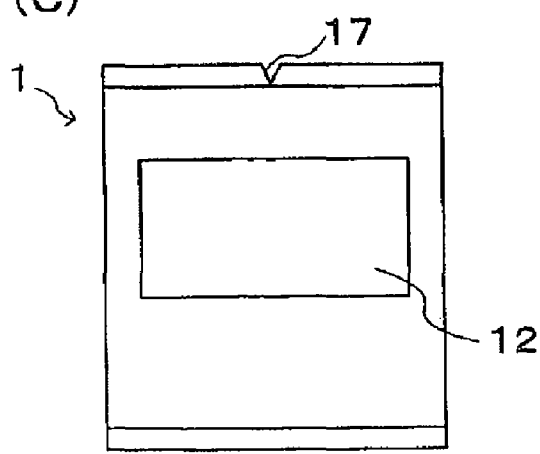
(D)
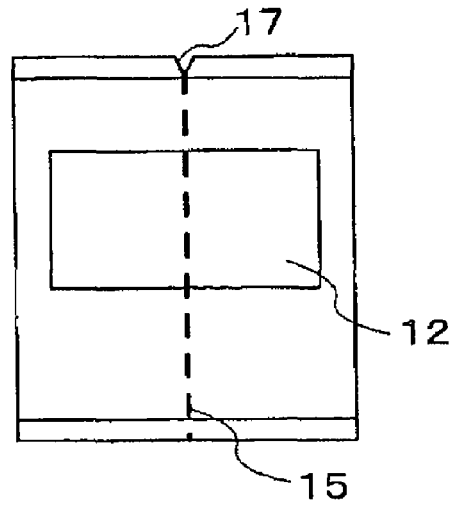

FIG. 6
(A)
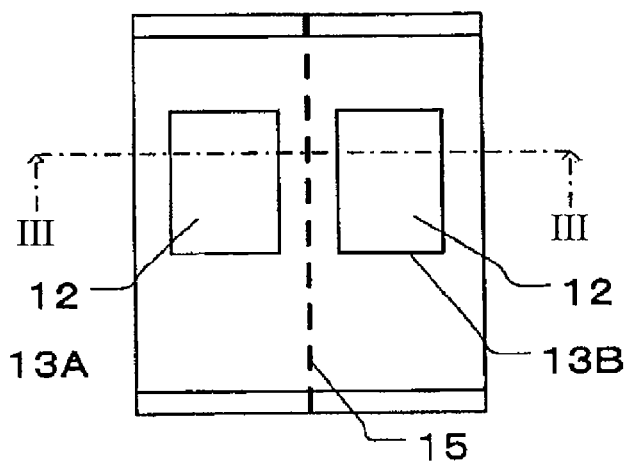
(B)
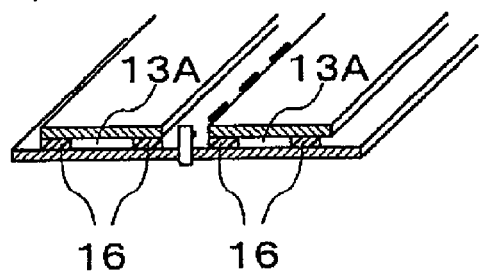
(C)
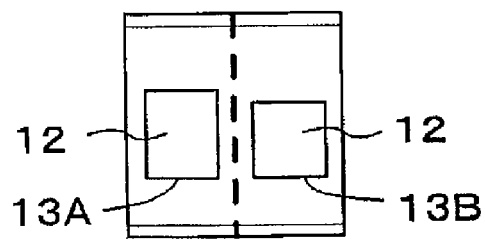
(D)
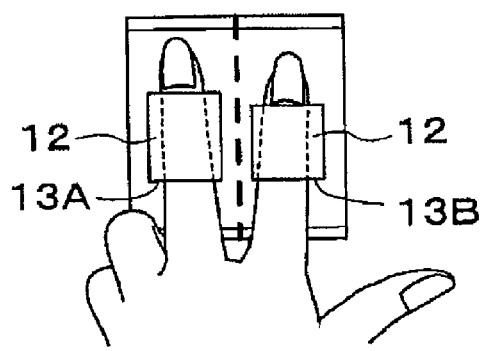

FIG. 12
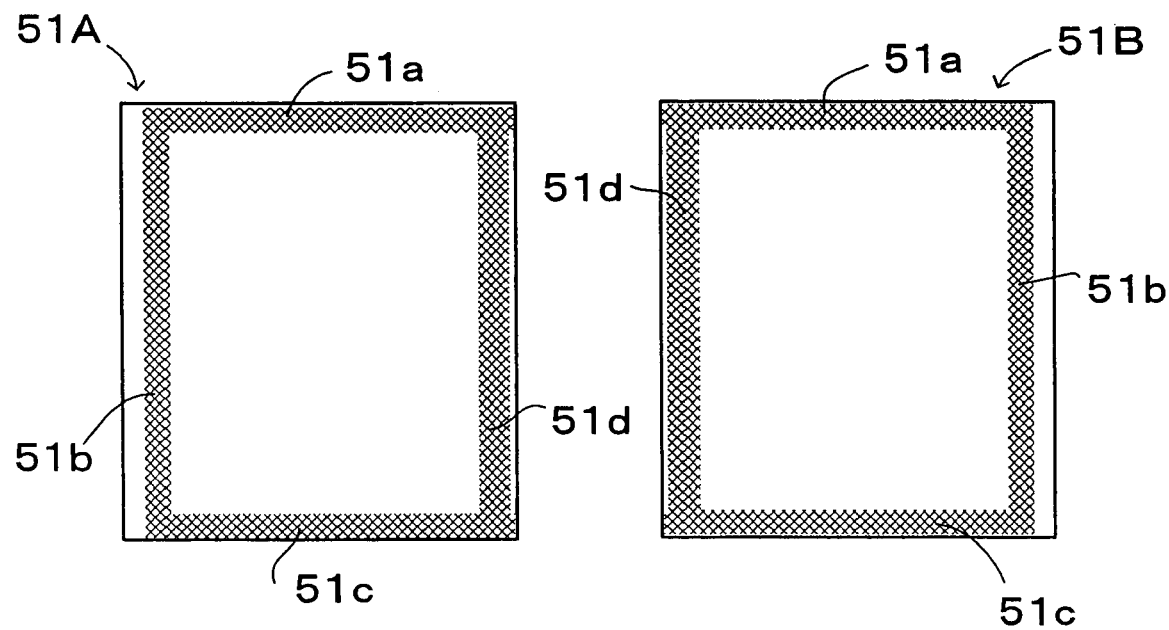
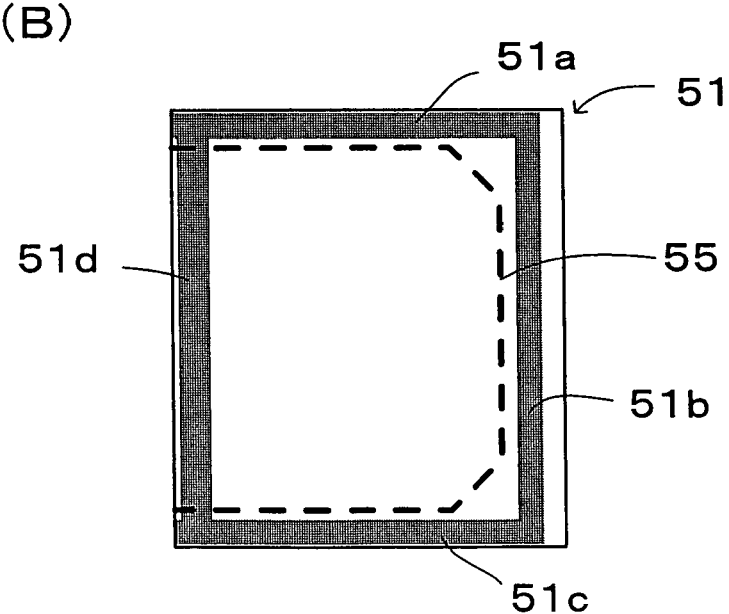

FIG. 17
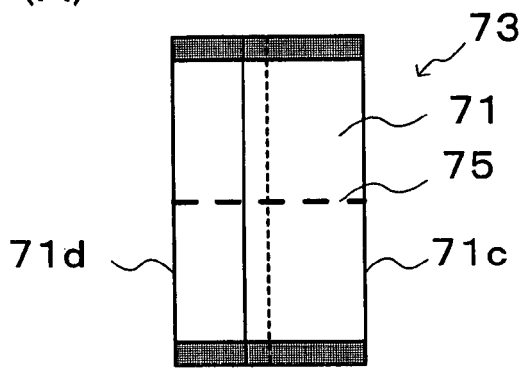
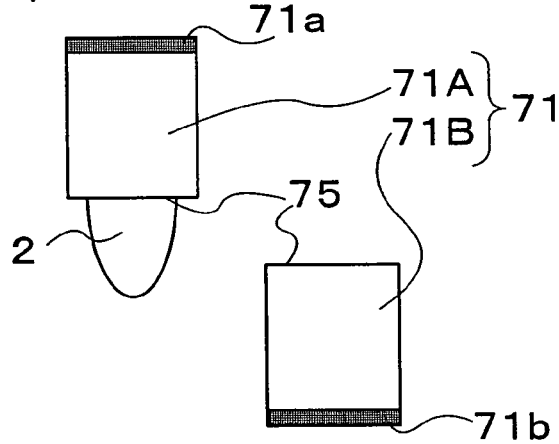
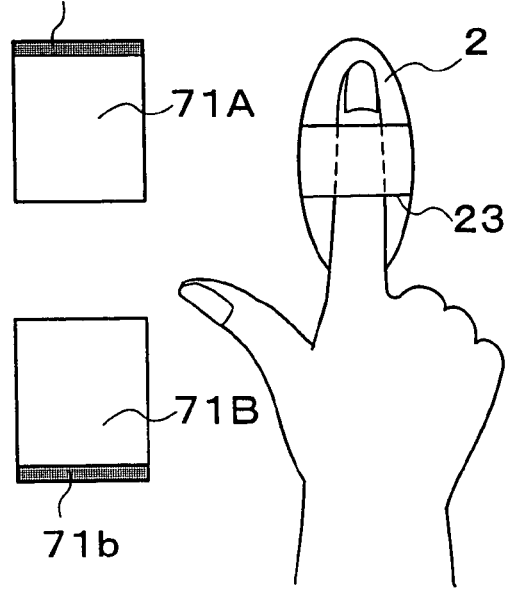
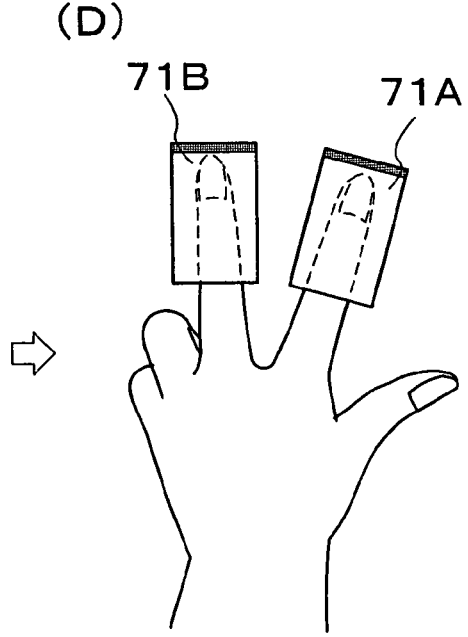

FIG. 21
(A)
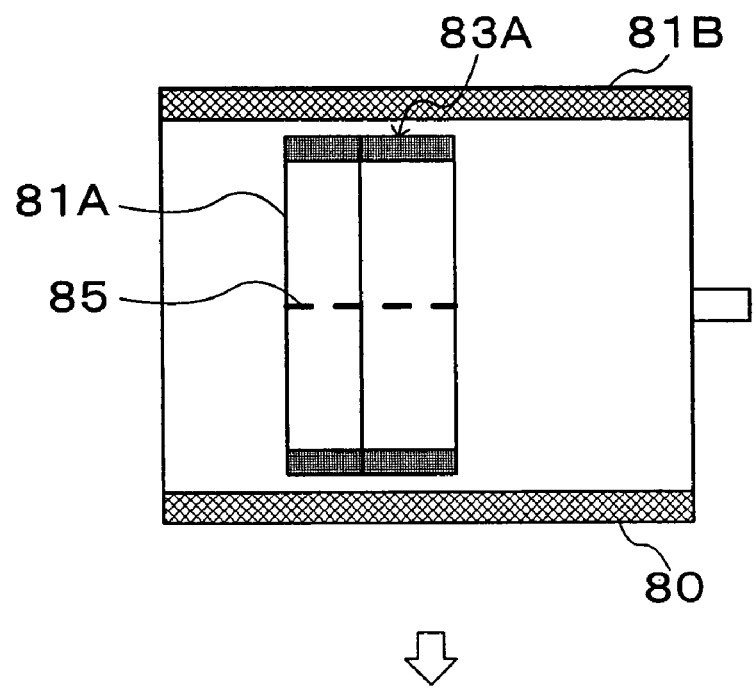
(B)
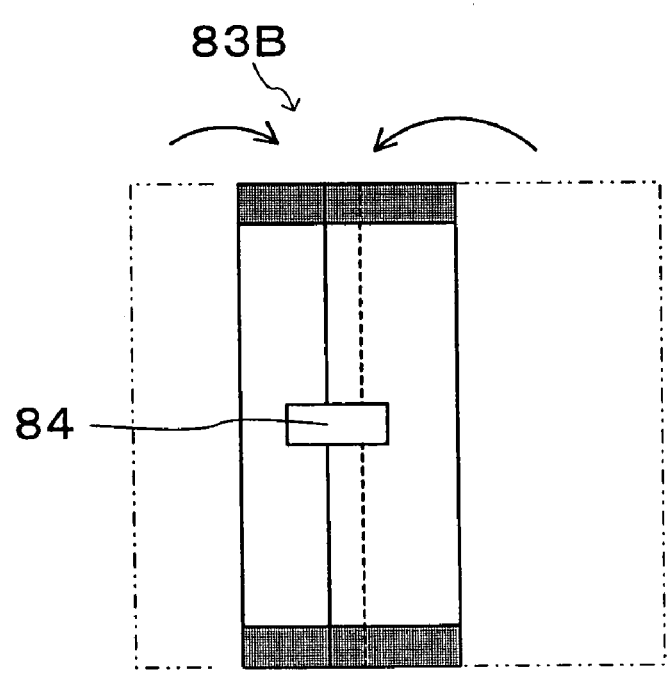

FIG. 22
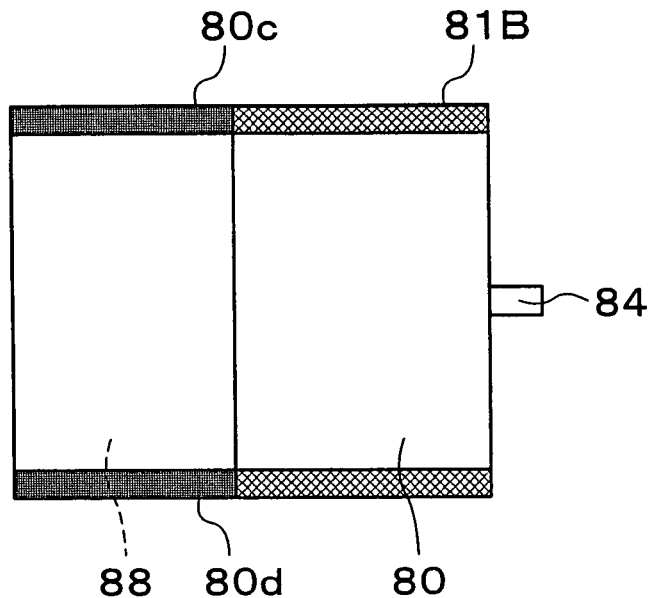
FIG. 23
(A)
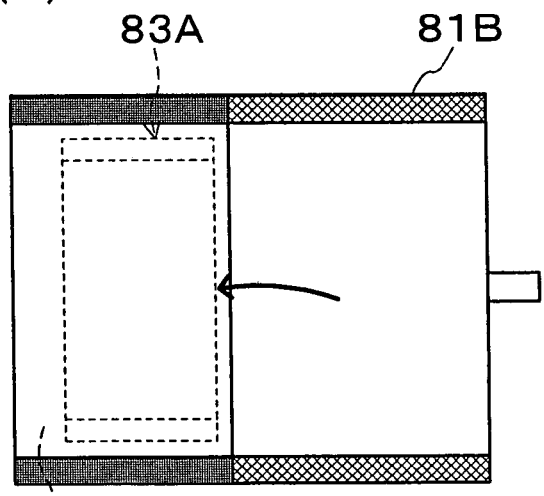
(B)
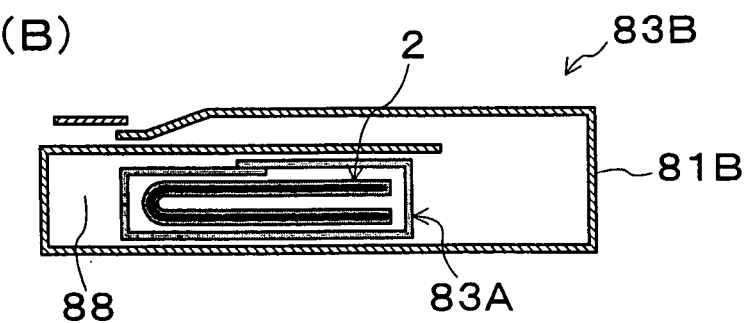

FIG. 24
(A)
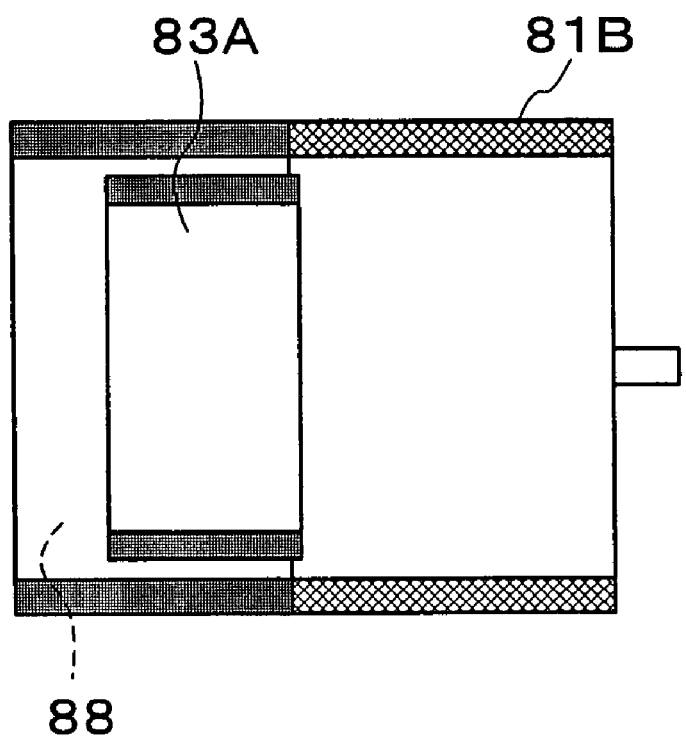
(B)
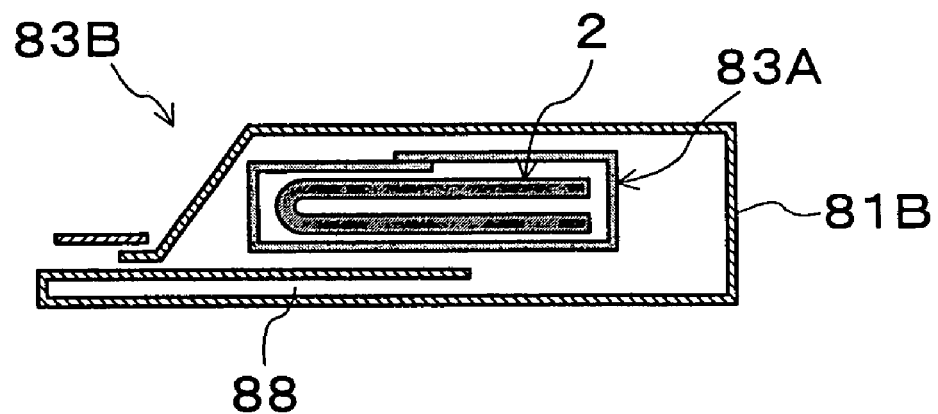

FIG. 31
(A)
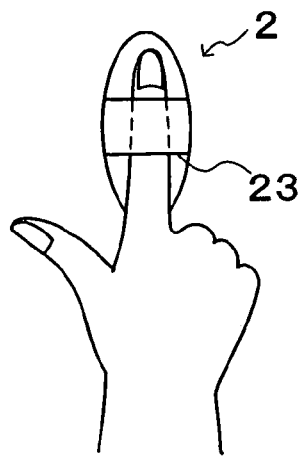
(B)
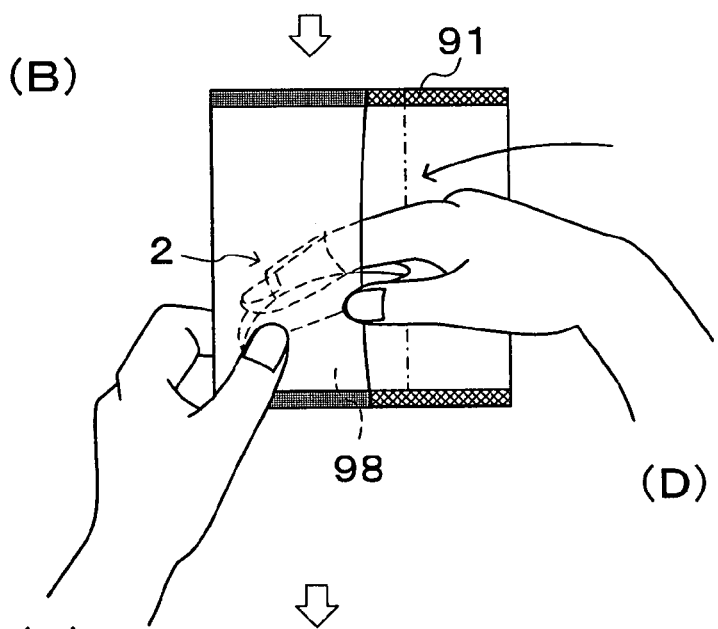
(C)
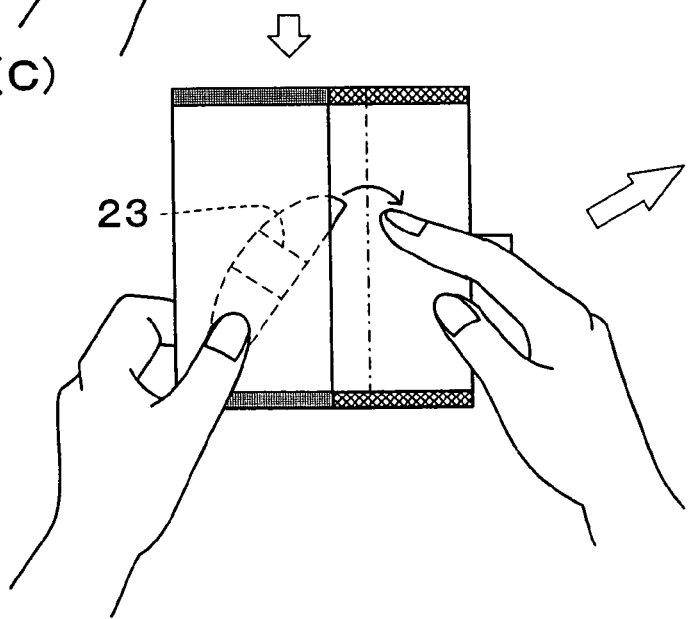
(D)
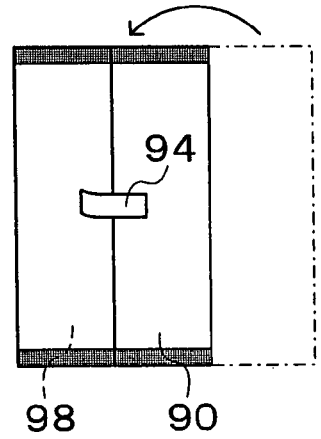

FIG. 32
(A)
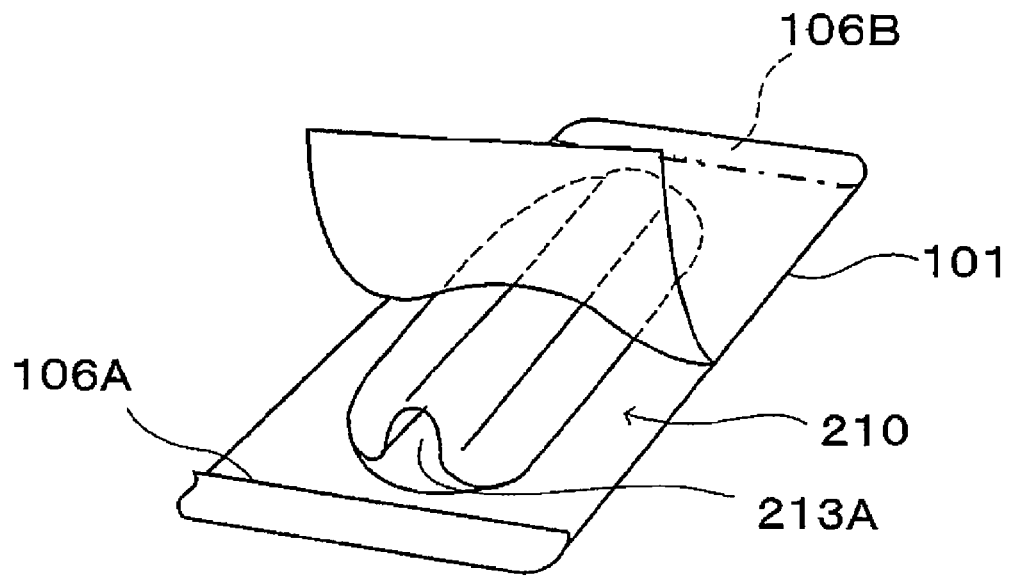
(B)
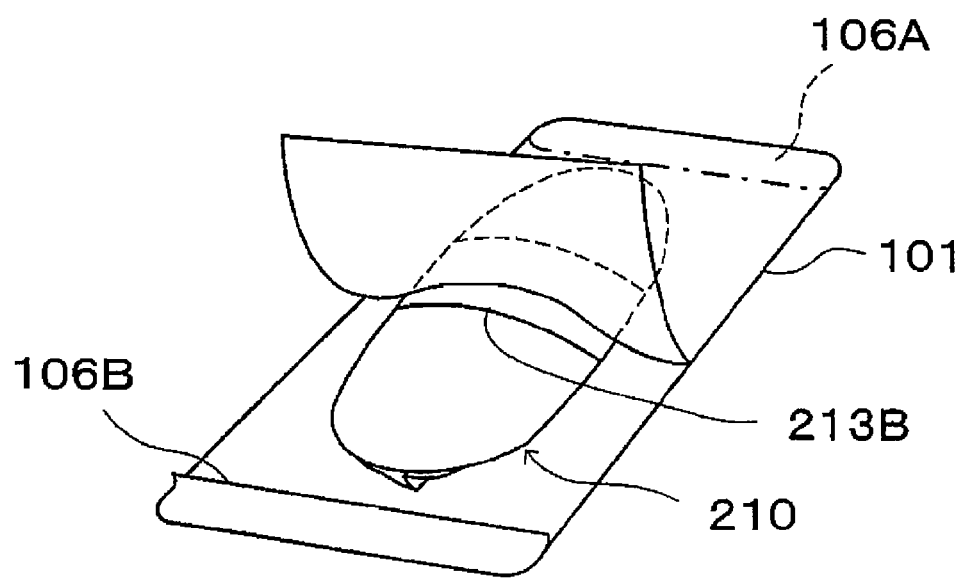

FIG. 35
(A)
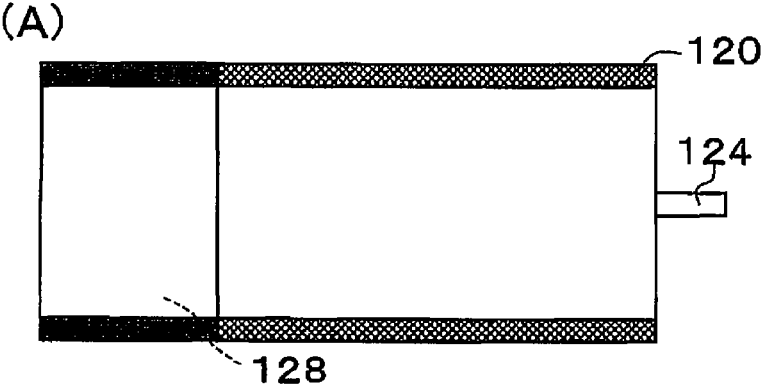
(B)
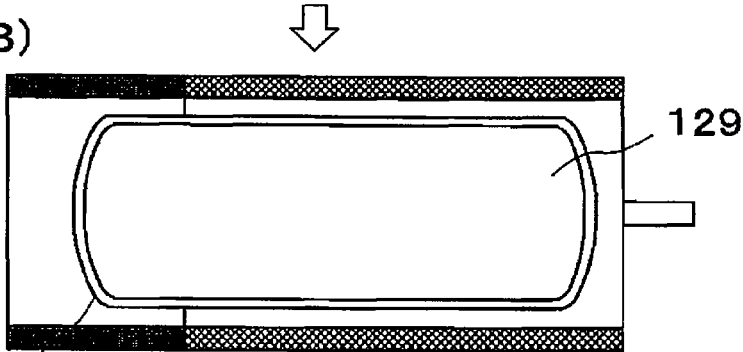
(C)
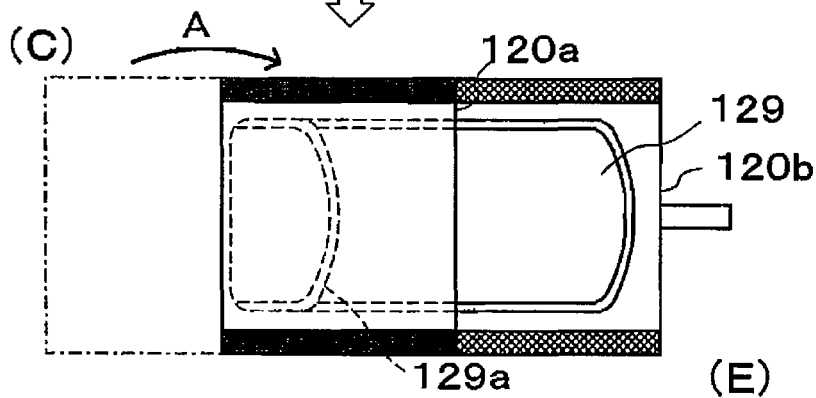
(D)
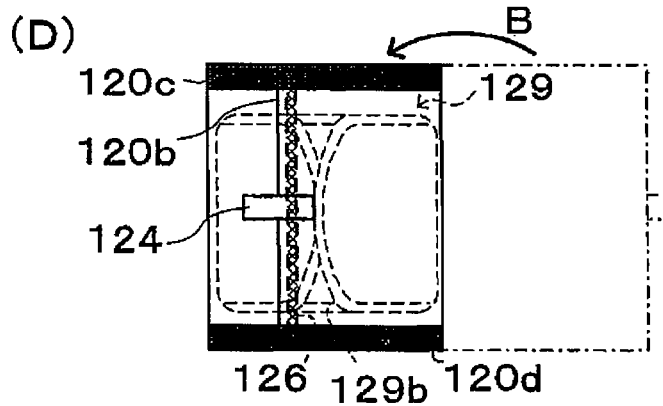
(E)
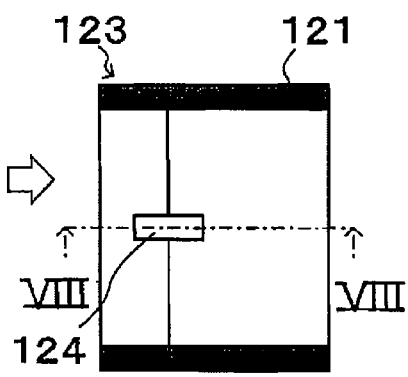

FIG. 39
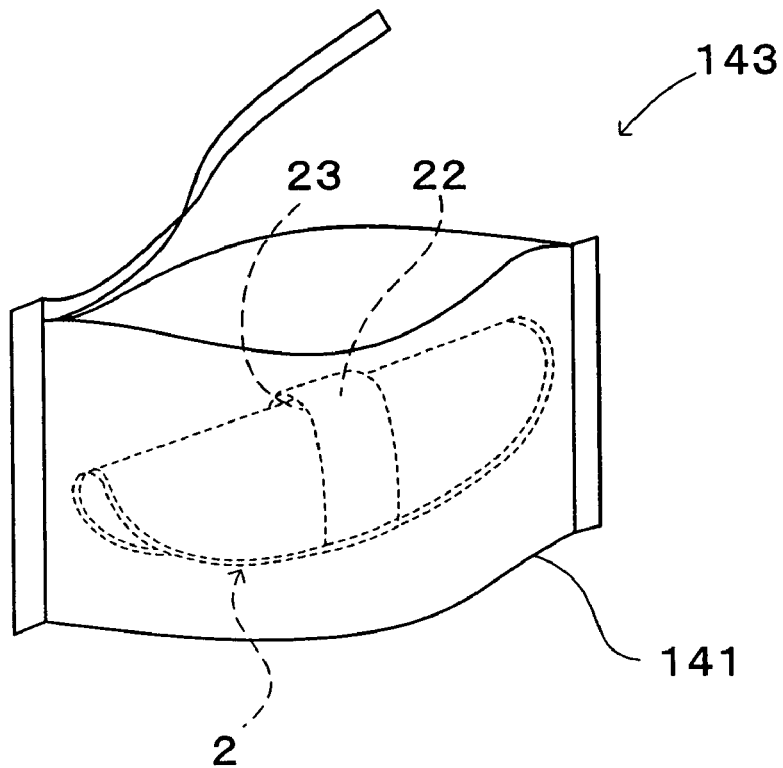
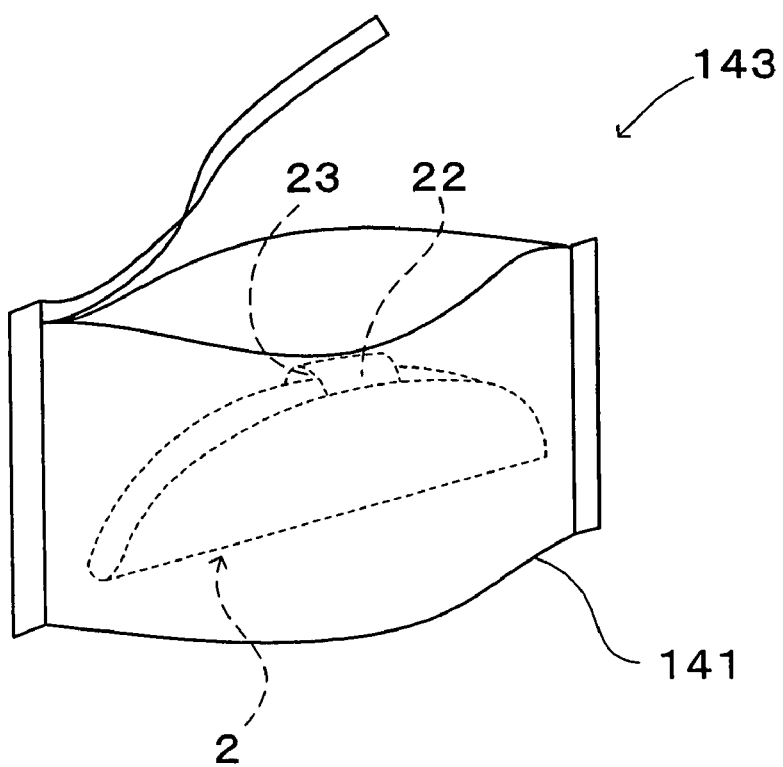

FIG. 40
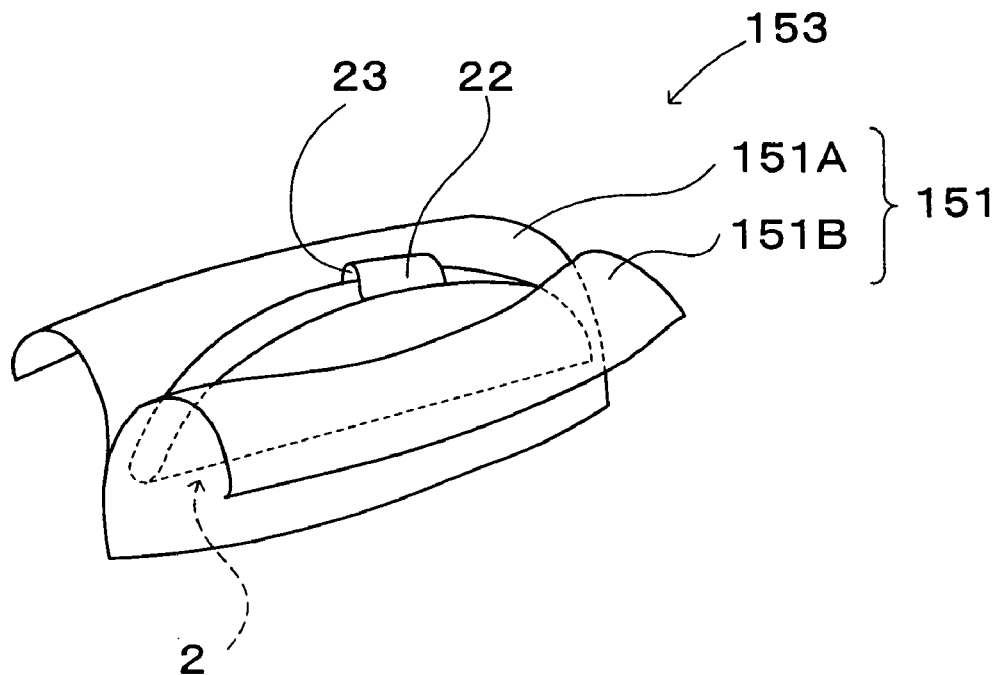
FIG. 41
(A)
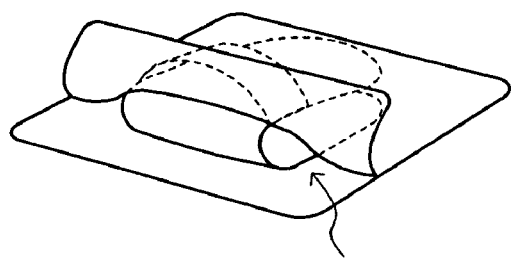
(B)
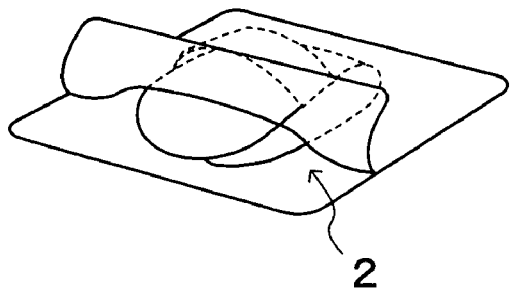

FIG. 47
(A)
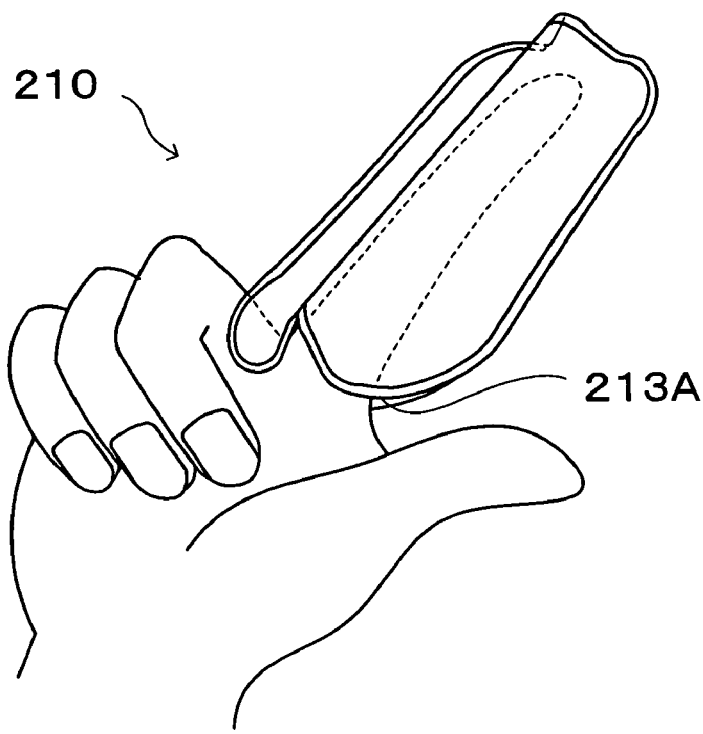
(B)
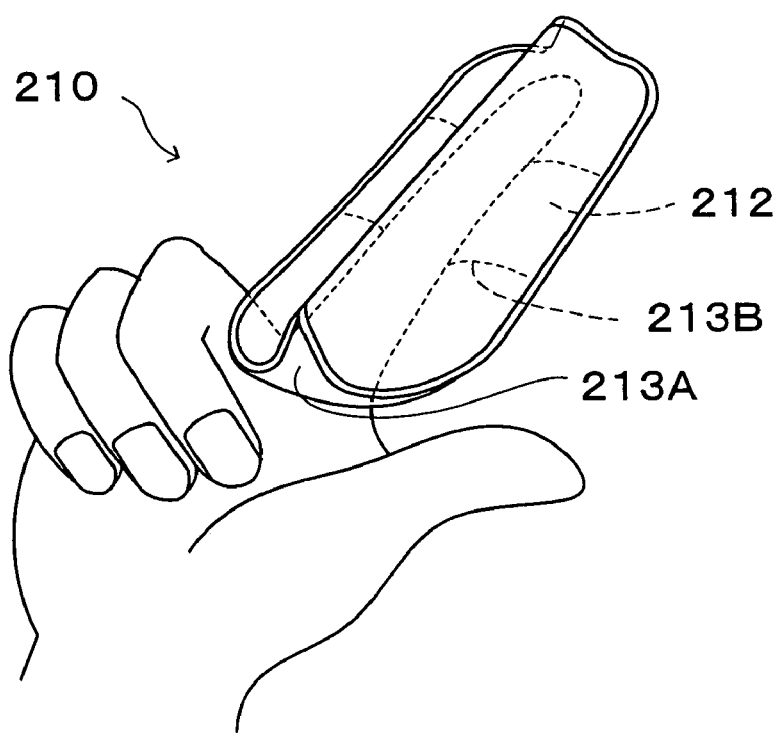

INTERLABIAL PAD INDIVIDUAL PACKAGING VESSEL

CROSS-REFERENCE TO RELATED APPLICATIONS

This application is a Continuation of International Application No. PCT/JP02/04882 filed May 21, 2002, which application published in Japanese on Nov. 28, 2002 as WO 02/094146 A1 under PCT Article 21(2).

BACKGROUND OF THE INVENTION

1. Technical Field

The present invention relates to a wrapping container for individually wrapping an interlabial pad of such a structure as facilitates surely and sanitarily fixing and unfixing the interlabial pad between the labia, and an individual wrapping body of the interlabial pad.

2. Background Art

Conventionally, a sanitary napkin and a tampon are used generally as female sanitary products. Here, there have been great efforts to prevent the leak of menstrual blood from gap caused by poor adhesion near the ostium vaginae as for the sanitary napkin. Moreover, as for the tampon, there have been great efforts for relieving the foreign feeling and the discomfort when wearing the sanitary products and intervaginal wearing trouble due to the nature of those products.

Under such situation, sanitary products of the interlabial pad have attracted people as a sanitary product positioned between the sanitary napkin and the tampon in recent years.

The interlabial pad is fixed by inserting it between the labia, having characteristics that it is difficult to cause the leak of menstrual blood because of higher adhesion to the body than that of the sanitary napkin and psychological resistance thereof on wearing is lower than that of the tampon which is inserted into the vagina.

Here, as to such an interlabial pad, developments and arrangements concerning the materials therefore and their peripheral members are insufficient.

The present invention has been made considering the problems as the above, and the purpose is to provide a preferred wrapping container for wrapping the interlabial pad as a preferred handling member of the interlabial pad.

Moreover, another purpose is to provide a wrapping container which can smoothly be held on a fingertip at the time of opening the wrapping container of the interlabial pad having a finger insertion opening.

SUMMARY OF THE INVENTION

In order to solve the problems as mentioned above, according to the present invention, the interlabial pad wrapping container is characterized in that it not only serves as a finger cot when the interlabial pad is fixed in, but also permits an wrapping container opening action and a finger cot fixing action at the same time.

Moreover, the wrapping container is also characterized in that to the interlabial pad provided with a finger insertion opening for being fixed on the tip of a finger, the wrapping container opening action is an action itself to smoothly insert a finger into the finger insertion opening as it is.

To be more concrete, the following arrangement is provided according to the following implementations of the present invention.

A wrapping container for individually wrapping an interiabial pad, includes a separation portion for separating the wrapping container into two separated sections. Each separated section after the separation turns up to be an operation member for wearing or removing the interlabial pad.

The wrapping container for individually wrapping the interlabial pad (hereafter, simply called the wrapping container) according to an implementation of the present invention, is made multi-functional only by arranging a separation part for separating the wrapping container into suitable sizes and shapes. Namely, the separation part is arranged on the wrapping container so that the wrapping container is suitable as an auxiliary member for fixing/unfixing the interlabial pad in/from labia. For example, a separation ratio etc. of the wrapping container separated by the separation part are determined so as to be suitable for such a separation part to exert its effect. Therefore, the individual wrapping container possesses not only its original function that it permits to singly, sanitarily, and easily carry only the interlabial pad to be used, but also the function that it can be used for fixing and unfixing the interlabial pad, and it permits to perform sanitarily fixing and unfixing the interlabial pad without such trouble as putting another finger cot on the finger.

The wrapping container for individually wrapping an interlabial pad can also be provided respectively with a finger insertion portion for inserting a finger respectively in a portion becoming respectively an separated section after the separation; and in a state where the wrapping container is separated into respective separated section at the separation portion, the finger is inserted in the finger insertion portion of respective separated sections which turn up to be an operation member for wearing or removing the interlabial pad.

The wrapping container for individually packaging an interlabial pad (hereafter, simply called a wrapping container) according to an implementation of the present invention, is provided with a separation part for dividing the wrapping container itself in two there, and finger insertion parts permitting to insert fingers therein in each part divided by the separation part. Therefore, a wearer can easily separate the wrapping container into two pieces by firstly inserting two fingers (for example, an index finger and a middle finger) into such insertion parts, respectively, and then opening the two fingers to the left and right, and also in this separated state, the pieces of the separated wrapping container are fixed on the tips of the fingers as a result. And, by maintaining this state, it becomes possible to fix and unfix the interlabial pad using the sections of the divided and separated wrapping container.

Here, since the labia differ in form among individuals, fixing procedures are sometimes different when the interlabial pad is fixed. For example, in the case of a wearer having a separate type labia shape, she can directly fix the interlabial pad in the labia by bending the posture. On the other hand, in the case of a wearer having a joint type labia shape, the inside of the labia is sometimes hard to be exposed only by bending the posture, and in such a case, she has to fix the interlabial pad therein while forcibly keeping the labia open using fingers of another hand which is not holding the interlabial pad.

When a labia opening action is performed, the fingers of the wearer have to come into direct contact with the labia. For this reason, dirt on the fingers may adhere to the labia, and this is a sanitary problem. Moreover, the mucous membrane may be stimulated. On the other hand, menstrual blood is apt to adhere to fingers, therefore, the wearer is obliged to do such an uncomfortable and troublesome action as washing out the menstrual blood adhering to the fingers every time she fixes the interlabial pad therein.

Regarding this point, the Japanese Utility Model Provisional Publication 61-232845(232845/1986) discloses a finger cot peelably adhered on a mount as a usable one when a tampon is inserted in a vagina. Thus, since the fingers of the wearer are prevented from coming into direct contact with the labia by fixing the interlabial pad by putting on such finger cots on the fingers, the labia part can be kept sanitary. Especially, since the finger cots are wrapped so as to be put on fingers without direct contact with the fingers, they have also an effect of remarkably reducing a risk that the dirt on the fingers adheres to the labia.

Moreover, the Japanese Utility Model Provisional Publication 62-9450(9450/1987) discloses such a finger cot as is provided with a grip part for preventing the finger cot from coming off a finger. It has been considered that non-contact between the labia and fingers may be more secured when such finger cots are used, because the finger cots fixed on the fingertips at the time of fixing an interlabial pad are prevented from coming off the fingers of the wearer.

However, since the interlabial pad is fixed between the labia which are difficult to watch, the fixing is not necessarily easy. Therefore, since putting on the separate finger cots at the time of fixing the interlabial pad as the example described above complicates the handling procedure, there is a fear that the fixing action may be made more difficult.

Then, it causes a longer fixing time if many actions have to be done at the time of fixing, and in such a case, menstrual blood may drop from inside of labia and adheres to an underwear and a toilet bowl or the periphery thereof, to make wearer feel uncomfortable for the treatments.

As to this point, according to an implementation of the present invention, the fixing action can be aided through the use of the sections of the torn wrapping container, moreover, when using such pieces, they are already held on the fingertips when the wrapping container is separated, therefore, the work process for purposely fixing them on the fingertips is unnecessary. Further, when separating the wrapping container, the wrapping container can easily be torn only by inserting two fingers of a non-dominant hand in the finger insertion parts and then opening them to the right and left, therefore, the fixing work can be speeded up.

Further, when unfixing an used interlabial pad from labia, it is possible to unfix it through the use of an interlabial pad to be newly used in order to prevent menstrual blood from adhering to fingers or prevent the fingers from contacting the labia.

Moreover, a "separation part" in this specification means what is specified in some form as a separated place of the wrapping container, and as a structure, perforations or the like which are an alternate arrangement of torn parts and untorn parts, or something to start tearing the wrapping container by making a cut part at the beginning of the separation part can be mentioned.

When the separation part is formed of perforations, a slit part is preferred to be 0.5-5 mm long and 3 mm wide at the maximum, and an unslit part is preferred to be 0.5-5 mm long. In such a manner, it is possible to guide the slit direction by the wearer not to deviate from the separation part, and is also possible to prevent dirt or the like from penetrating into the wrapping container from the separation part. Moreover, in order for the separation part to be easily slit, it is preferable to bring the separation part into penetration state in the direction of thickness.

As far as the starting point of the separation part formed of perforations is started from one end edge of the wrapping container prepared at least for finger insertion, it does not matter even if the starting point is connected up to another end edge or it is arranged only up to an intermediate position from the one end edge.

The breaking strength of the perforations is preferably 0.2-3.0 N/25 mm, more preferably 0.3-1.5 N/25 mm, under the pulling conditions of a 25 mm width and 100 mm/min when the perforations are pulled in the direction orthogonal to the perforations with the perforations positioned in the center.

The wrapping container for individually wrapping an interlabial pad includes a finger insertion portion composed of a mini sheet piece for a wrapping container attached so that an opening for inserting a finger be formed, with, two or more bonding portions to the wrapping container, and one or more non-bonding portions; and the mini sheet piece for wrapping container is attached in a state striding across the separation portion in the wrapping container, or attached respectively to both sides of the separation portion.

BRIEF DESCRIPTION OF THE DRAWINGS

FIGS. 1(A)-(D) illustrate the interlabial individual wrapping container of the first embodiment, and show a process drawing illustrating the process for forming the wrapping body while packaging the interlabial pad in the wrapping sheet.

FIGS. 5(A)-(D) show the rear face of FIG. 3.

FIGS. 6(A)-(D) illustrate another form of the mini-sheet piece for the wrapping container of the interlabial pad individual wrapping container in accordance with the first embodiment.

FIGS. 12(A)-(B) illustrate another constitution of the wrapping container for individually wrapping an interlabial pad in accordance with the second embodiment, and illustrates a mode in which the wrapping container for individually wrapping an interlabial pad is formed by sticking two wrapping sheets together.

FIGS. 17(A)-(D) illustrate a method for separating the wrapping container of the fourth embodiment into two sections to open the same and a method for fixing the two sections on the fingertips.

FIGS. 21A-B illustrate the wrapping container in accordance with the fifth embodiment.

FIG. 22 shows drawings illustrating a state in which the outer wrapping container of the wrapping container for individually wrapping an interlabial pad in accordance with the fifth embodiment has pocket portion.

FIGS. 23(A)-(B) illustrate a state in which an inner wrapping body is enclosed in the pocket portion arranged on the outer wrapping container of the wrapping container for individually wrapping an interlabial pad in accordance with fifth embodiment, to make an outer wrapping body.

FIGS. 24(A)-(B) illustrate a state in which the inner wrapping body is arranged on the pocket portion provided on the outer wrapping container of the wrapping container for individually wrapping an interlabial pad in accordance with the fifth embodiment, to make the outer wrapping container.

FIGS. 31(A)-(D) illustrate a process for unfixing a used interlabial pad by using the interlabial pad individual wrapping container in accordance with the sixth embodiment.

FIGS. 32(A)-(13) illustrate the interlabial pad individual wrapping container in accordance with the seventh embodiment.

FIGS. 35(A)-(E) illustrate a method for keeping the sanitary napkin in the sanitary napkin wrapping container with the pocket portion, to make the package into the wrapping body.

FIGS. 39(A)-(B) illustrate the wrapping body in which the interlabial pad in accordance with this embodiment is contained in the interlabial pad individual wrapping container where the mini-sheet for the interlabial pad is folded so as to form a chevron.

FIG. 40 illustrates the wrapping body with interlabial pad individual wrapping container containing therein the interlabial pad in accordance with this embodiment to be opened like double doors opening outward.

FIGS. 41(A)-(B) illustrate different methods for folding the interlabial pad.

FIGS. 47(A)-(3) illustrate a state in which an interlabial pad with two finger insertion openings is held on the fingertip.

DETAILED DESCRIPTION OF THE INVENTION

Figure 2:
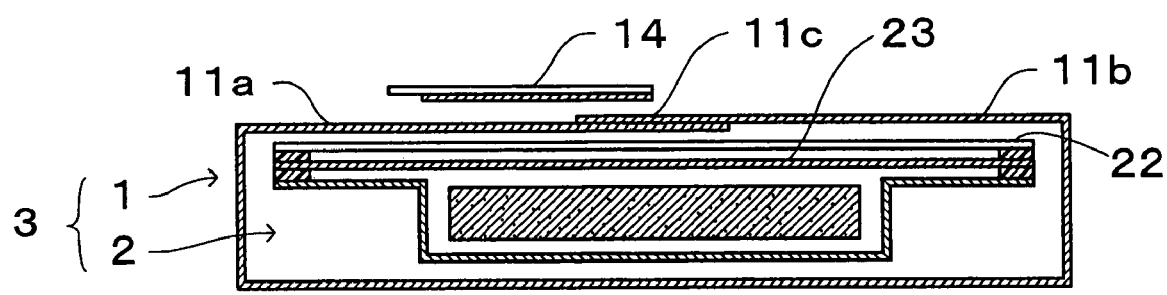
FIG. 2 is a sectional view taken along the arrow line I-I of the FIG. 1(D).

According to the wrapping container for individually wrapping an interlabial pad (hereafter, simply called a wrapping container) according to an implementation of the present invention, the finger insertion part is formed by attaching the finger insertion opening part and the following finger insertion space part to the wrapping container in a state unconnected to the wrapping container surface. Therefore, a wearer can insert a finger from the opening of the finger insertion opening and fix the wrapping container on the fingertip (refer to FIG. 7).

When a mini-sheet piece for the wrapping container is made to be a belt-like piece in an implementation of the present invention, the belt-like piece is to be attached to the wrapping container in the state striding over the separation part (refer to FIG. 5). Associated with this, the separation part is arranged in the state penetrating both the wrapping container and the mini-sheet piece for the wrapping container in the direction of thickness, therefore, it is necessary to take care so as not to damage the mini-sheet piece for the wrapping container.

Moreover, according to an implementation of the present invention, a plurality of the mini-sheet pieces for the wrapping container can be arranged on both sides bordered by the separation part (refer to FIG. 6). Thus, the separation part is not arranged on the mini-sheet pieces for the wrapping container. Namely, the mini-sheet pieces for the wrapping container and the adhesion part do not exist on the separation part, so the breaking strength of the whole separation part can be made almost constant at the time of slitting and dividing the separation part. Therefore, the wrapping container can stably be separated compared with the case in which a piece of belt-like mini-sheet for the wrapping container is attached striding over the separation part.

The mini-sheet pieces for the wrapping container can be joined to the wrapping container not only with an adhesive, but also by means of heat-sealing, ultrasonic sealing, an adhesive tape, or the like.

Moreover, for easy discrimination of the mini-sheet pieces for the wrapping container by a wearer, the mini-sheet pieces for the wrapping container are adjusted so as to have a different tone and pattern or chromaticity from those of the wrapping container by means of coloring or printing a pattern or the like.

The mini sheet piece for wrapping container can be attached to an outer face side and/or inner face side of the wrapping container.

According to the wrapping container for individually packaging interlabial pad (hereafter, simply called a wrapping container) according to an implementation of the present invention, the wrapping container is provided with the mini-sheet pieces on the outer surface or the inner surface, or on both of the outer and inner surfaces.

Here, according to an implementation of the present invention, the wrapping container comes into contact with the labia on the inside surface. Therefore, in order to realize fixing or unfixing of a sanitary interlabial pad by reducing adhesion of dirt and dust to labia, it is especially more preferable to arrange the mini-sheet pieces for the wrapping container on the outside than on the inside.

The wrapping container can have a finger insertion opening; and the wrapping container for individually wrapping an interlabial pad is provided with a pre-unwrapped opening that allows the finger insertion opening of the interlabial pad contained therein to be exposed naturally at the beginning of unwrapping of the wrapping container for individually wrapping an interlabial pad, in addition to the separation section.

According to the wrapping container for individually packaging the interlabial pad (hereafter, simply called a wrapping container) according to an implementation of the present invention, the wrapping container is provided with a "pre-unwrapped opening" separately from the separation part for slitting up the wrapping container. Since the finger insertion opening provided on the enclosed interlabial pad is exposed by opening such a pre-unwrapped opening, the finger insertion opening is brought into the state in which a wearer can watch it. Thus, the wearer is then able to insert a finger in the finger insertion opening immediately after the wearer has opened the wrapping container.

Moreover, in the present invention, the "pre-unwrapped opening" means what forms an unwrapped opening permitting to insert a finger in the finger insertion opening of the interlabial pad through there. In the present invention, the size of this "pre-unwrapped opening" is sufficient as long as the wearer can watch the finger insertion opening of the interlabial pad through the pre-unwrapped opening by unsealing it and she can insert her finger in the finger insertion opening, but as a size permitting to unfixing the interlabial pad, the pre-unwrapped opening may be sized for permitting to unfix the interlabial pad through there.

The wrapping container for individually wrapping an interlabial pad can be composed of a series of wrapping sheet wound in a way to form a overlapping part where a part thereof is folded, or of a series of wrapping sheet wound in a way to form a overlapping part where both ends thereof are superposed each other, wherein: the pre-unwrapped opening is formed of the overlapping part.

The wrapping container for individually wrapping the interlabial pad (hereafter, simply called a wrapping container) according to an implementation of the present invention is formed by folding a wrapping sheet. And, a pre-unwrapped opening for opening the wrapping container is formed from the overlapping part of both side parts of the folded wrapping sheet. Therefore, a wearer is easily able to open the wrapping container by opening the overlapping part of the wrapping sheet.

Figure 9:
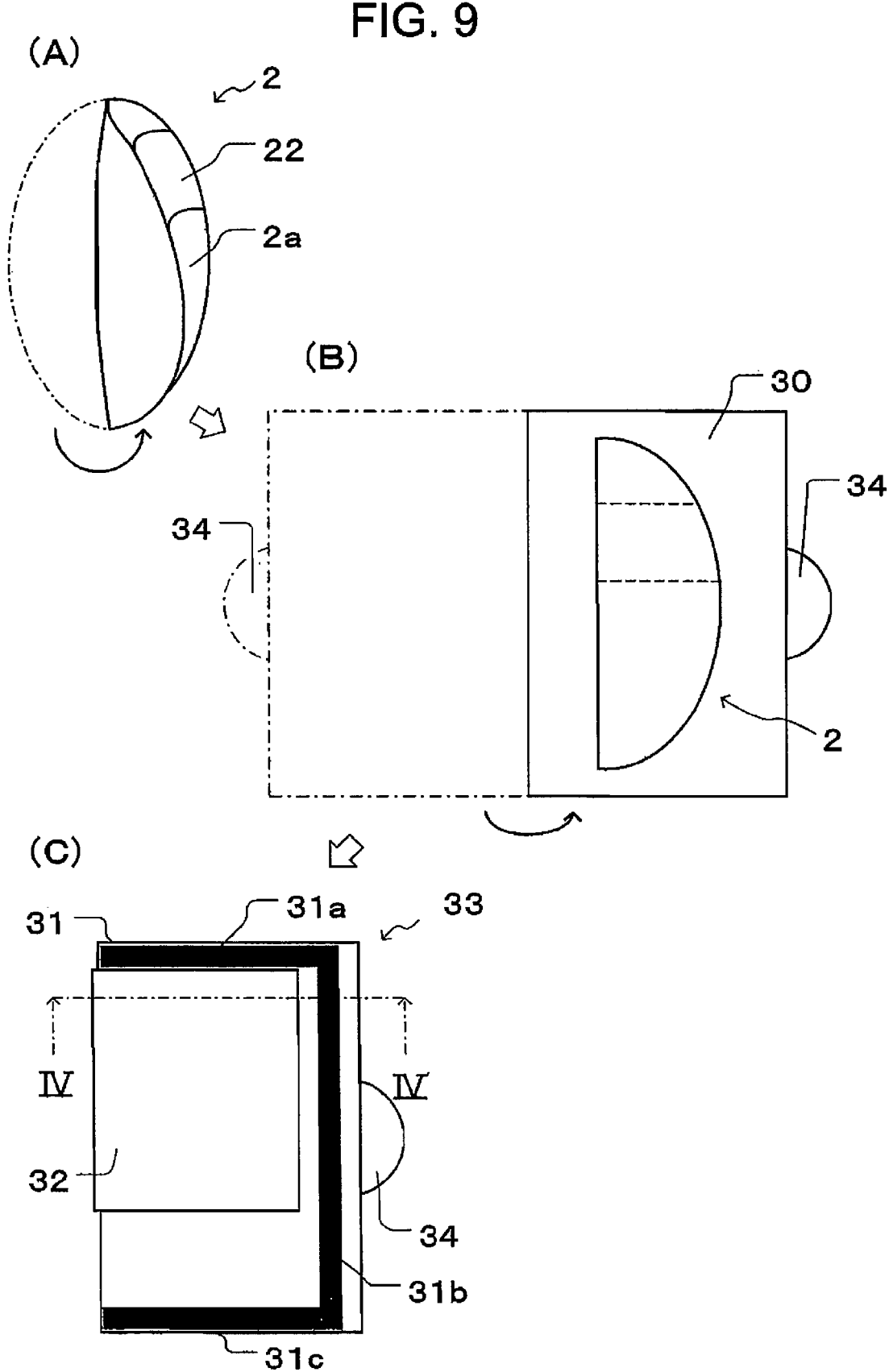
FIGS. 9(A)-(C) illustrate the wrapping container for individually wrapping an interlabial pad in the second embodiment, and is a process drawing showing a process for wrapping the interlabial pad in the wrapping sheet in accordance with the second embodiment.

As typical methods for folding a wrapping sheet, such methods can be mentioned as the wrapping sheet folded in three where the interlabial pad is placed approximately in the middle of the wrapping sheet and the wrapping sheet is folded inside from both side parts thereof (refer to FIGS. 1(A)-(D)), and the wrapping sheet is folded in half holding the interlabial pad in between (refer to FIG. 9). In these cases, the overlapping part, where the side parts of the folded wrapping sheet are layered, serves as the pre-unwrapped opening, and is stuck by heat-sealing or the like so as to be peelable.

Moreover, in order to facilitate unsealing the pre-unwrapped opening, in the case of the three-folded one, the overlapping part of the wrapping sheet can be provided with a stop tape with dry edges thereon, and in the case of the double-folded one, the overlapping part can be provided with a tab thereon. Thus, since a wearer can easily open the pre-unwrapped opening by picking up such a stop tape and tab, an action for fixing the interlabial pad can be made speedier.

The pre-unwrapped opening can be composed of a broken line whose both ends are connected to the separation portion, and a tearing portion formed by tearing off a part of the wrapping container for individually wrapping an interlabial pad along the broken line; and the unwrapping is executed by tearing off a part of the wrapping container for individually wrapping an interlabial pad along the broken line.

According to the wrapping container for individually wrapping interlabial pad (hereafter, simply called a wrapping container) according to an implementation of the present invention, the pre-unwrapped opening for forming an unwrapped opening is opened by tearing a part of the wrapping container along a broken line and pulling down the torn part.

The "broken line" is formed in an inner side than the joining part for sealing the wrapping container in the overlapping part of the wrapping sheet, and the composition thereof is the same as the separation part described above in the Summary section.

Moreover, when the pre-opening part is comprised of the broken line, it is preferable to form the wrapping container by folding the wrapping sheet in two. In this case, the three edges except the folded part are joined by heat-sealing or the like.

The separation portion and the pre-unwrapped opening can be oppositely positioned.

According to the wrapping container for individually wrapping interlabial pad (hereafter, simply called a wrapping container) according to an implementation of the present invention, the pre-unwrapped opening and the separation part are arranged in the opposite positions to each other. Here, since the finger insertion part with the finger insertion openings is arranged in the neighborhood of the separation part, this allows a wearer to open the pre-unwrapped opening and insert fingers of her dominant hand therefrom into the finger insertion openings of the interlabial pad, while this also allows her to insert fingers of another hand into the finger insertion opening of the wrapping container. As a result of this, the interlabial pad can be taken out of the wrapping container by using both hands, therefore, such an unfixing action is made efficient and smooth.

The wrapping container can have a finger insertion opening; the wrapping container is provided with a pre-unwrapped opening that allows the finger insertion opening of the interlabial pad contained therein to be exposed naturally at the beginning of unwrapping of the wrapping container, and a separation edge turning to be the separation portion; the wrapping container has a bean sheath shape, provided with the pre-unwrapping edge along one edge thereof and, at the same time, the separation edge is provided along the other edge continuous to this pre-unwrapping edge, and a finger cot where a finger can be inserted is formed right and left respective sides face becoming respectively an separated section after the separation of the wrapping container along the separation edge; and in a state where the wrapping container is separated into respective piece, the finger is inserted in the finger cot section portion in respective piece which turns up to be an operation member for wearing or removing the interlabial pad.

According to the wrapping container for individually wrapping interlabial pad (hereafter, simply called a wrapping container) according to an implementation of the present invention, when the interlabial pad is folded with the approximate center area in the longitudinal direction used as an axis and enclosed therein, the pad is shaped to be easy to fit. Therefore, this makes it possible to eliminate unnecessary gaps in the wrapping container, and also make it compact.

Moreover, the wrapping container according to an implementation of the present invention is provided with two finger cots on the side for inserting fingers therein. Therefore, a wearer inserts two fingers (for example, an index finger and a middle finger) in each finger cot, respectively, and then opens the fingers to both sides, and can thereby easily slit the wrapping container into two pieces. As a result of this, the slit pieces are firmly held on respective fingers, therefore, this state allows the wearer to fix or unfix the interlabial pad. Thus, even when the wearer performs an action of opening the labia or the like, she can prevent the labia from touching the fingers.

(The pre-unwrapping edge can be composed of a broken line whose both ends are connected the separation portion, and a tearing portion formed by tearing off a part of the wrapping container for individually wrapping an interlabial pad along the broken line; the unwrapping of the pre-unwrapping edge is executed by tearing off a part of the wrapping container for individually wrapping an interlabial pad along the broken line; and the starting point of the broken line is disposed in such a place to be positioned near the finger insertion opening of the interlabial pad, when the interlabial pad is contained.

According to the wrapping container for individually wrapping interlabial pad (hereafter, simply called a wrapping container) according to an implementation of the present invention, a broken line is formed on a pre-unwrapped edge. Therefore, the wearer tears a part of the wrapping container along this broken line, and thereby she can open the pre-unwrapped edge, which is one edge part of the wrapping container, to make the finger insertion openings of the enclosed interlabial pad to be exposed, and can insert the fingers in such finger insertion openings.

The wrapping container can include a flat cylindrical shape longer than is wide where both ends are closed; in a state where the wrapping container is separated into respective separated section at the separation portion, the wrapped interlabial pad is exposed and, at the same time, the separation portion of the separated respective piece becomes an opening where a finger can be inserted, and, with a finger is inserted from the opening, the separated section turns up to be an operation member for wearing or removing the interlabial pad.

According to the wrapping container for individually wrapping interlabial pad (hereafter, simply called a wrapping container) according to an implementation of the present invention, the two split pieces themselves serve as the finger cots for the interlabial pad handling members. Therefore, as described above, this arrangement eliminates the need for such a manufacturing process as attaching a mini-sheet piece separately, and permits to simplify the manufacturing process.

Moreover, since the length from the inside of the joint part of both closed edges up to the separation part is an insertion length of a single finger, the dimension needs to be such a length as each section does not easily slip off the fingers inserted from the opening, namely, the separation part, before, during, and after the action for fixing and unfixing the interlabial pad. Further, in the state before separation, the length from the inside of the joined part of one edge end up to the inside of the other edge end needs to have a dimension permitting to enclose the interlabial pad. From these, the length is preferable to be at least 40 mm, more preferably, it is in a range of 60-90 mm to avoid causing a feeling of too much slack. Moreover, it is customary that, as to the joined part at both edge ends of the wrapping container, the length from the end of the wrapping container toward the separation part is arranged within a range of 2-5 mm.

Also as to a width dimension of the wrapping container, the width is preferred to be 20 mm or wider considering fixation of the enclosed interlabial pad to the wrapping container, finger insertion, and holding ability of the inserted state, more preferably, the width is to be arranged within a range of 25-40 mm.

When the separation part is formed from a broken line, the intervals between the slits of the broken line are arbitrarily arranged, however, the tear strength of the broken line is at least 1 N/25 mm or more, preferably, it is within a range of 0.2-3.0 N/25 mm, considering that the break of the wrapping container should be guided along the broken line; the packaging material should not be damaged; and it should have a preservation capability. Moreover, the numerical value is defined as a reading of the maximum load when measuring the tear strength at a speed 100 mm/min by holding respective edge ends with the upper and lower chucks using a tensilon tensile tester and then partly cutting the tip of the broken line with scissors.

The separation portion can be set in such length that the starting point thereof starts from one end edge and the terminal thereof does not reach the opposed other end edge.

According to the wrapping container for individually packaging interlabial pad (hereafter, simply called a wrapping container) according to an implementation of the present invention, the separation part is arranged so as to start from one edge end of the wrapping container and not to be extended up to the other edge end, but to end in the neighborhood thereof. To be more concrete, for example, in a portrait form wrapping container, the separation part is started from the edge end which is one side part in the longitudinal direction, and ended so as not to reach the other side part opposite thereto (refer to FIG. 19). Therefore, the wrapping container is not completely separated into two before it has been fixed or unfixed, but is maintained as it is, in the connected state in the part where the separation part does not exists. As a result of this, to put the separated sections on the fingertips, the two fingers can be inserted in the respective sections at the same time, and moreover, one of the sections is prevented from being lost, therefore, handling is simplified and also speeded up.

Moreover, when an interlabial pad with finger insertion openings is enclosed, the interlabial pad is enclosed so that such finger insertion openings are directed to the edge end side where the separation part is started, and thereby a wearer can watch the finger insertion openings immediately after opening the wrapping container. Moreover, the range where the separation part is not provided is preferred to be about 2-10 mm from one edge end.

A wrapping container for individually wrapping an interlabial pad, includes a containment container for wrapping directly an interlabial, and an outer wrapping container for wrapping an inner wrapping body containing the interlabial pad in the inner wrapping container, wherein: the inner wrapping container composes a flat cylindrical shape longer than is wide where both ends are closed; the inner wrapping container is provided with a separation portion for separating the wrapping container into two small pieces; and in a state where the wrapping container is separated into respective separated section at the separation portion, the separation portion of respective piece becomes an opening where a finger can be inserted, and by inserting the finger from the opening, turns up to be an operation member for wearing or removing the interlabial pad.

According to the wrapping container for individually packaging interlabial pad (hereafter, simply called a wrapping container) according to an implementation of the present invention, the wrapping container is double-structured consisting of an inner wrapping container and an outer wrapping container, and the inner wrapping container of them is a member for aiding the fixing and unfixing actions of the wrapping container. Therefore, they can also be properly used; for example, the inner wrapping container is used for fixing and unfixing the interlabial pad, and the outer wrapping container is used for enclosing the used interlabial pad, so menstrual blood having adhered to the wrapping container can be prevented from further adhering to the fingers.

The wrapping container can be made of a wrapping sheet having a pocket portion capable of an interlabial pad of a size and shape allowing to hold by pinching between the labia, in a state where the interlabial pad is folded half longitudinally taking the longitudinal direction of interlabial pad as an axis.

According to the wrapping container for individually packaging interlabial pad (hereafter, simply called a wrapping container) according to an implementation of the present invention, a pocket portion is formed on the wrapping container beforehand. Therefore, by enclosing an unused interlabial pad in this pocket portion beforehand, the interlabial pad is prevented from falling out when a wearer opens the wrapping container to take out the interlabial pad. Moreover, by directing the finger insertion openings of the interlabial pad toward the opening of this pocket portion, the fingers can be inserted in the finger insertion openings making good use of the state in which the interlabial pad is enclosed in the pocket portion (refer to FIG. 30).

Moreover, when a wearer holds an interlabial pad on the fingertips by inserting the fingers in the finger insertion openings of the interlabial pad to unfix the interlabial pad which has been fixed in the labia, she inserts the interlabial pad in the pocket portion together with the fingers at the time of taking out the used interlabial pad from the fingertips, and fixes the interlabial pad in the pocket portion by picking it from the outside (outside of the wrapping container) of the pocket portion by the other hand, and she can draw her fingers from the finger insertion openings in that state (refer to FIG. 31(C)). In such a manner, the finger can be drawn out without adhesion of menstrual blood or the like to the finger. Moreover, the used interlabial pad can be thrown away without contact between the menstrual blood and the hands of the wearer, and further, since the used interlabial pad can be enclosed in the individual wrapping container, it looks also sanitary.

When the used interlabial pad is re-held in the wrapping container, the menstrual blood absorbed in the interlabial pad sometimes contacts with the pocket portion in the neighborhood of its opening and adheres thereto. Therefore, the menstrual blood is prevented from adhering to a wearer's hand by covering the opening of the pocket portion by the part other than the pocket portion in the wrapping sheet, and this ensures a sanitary treatment.

Moreover, the wrapping container is preferred to be provided with a sealing means such as a stop tape on the part covering the pocket portion. This arrangement makes it possible to surely keep the used interlabial pad enclosed in the wrapping container, and prevents the interlabial pad from falling out and also prevents the menstrual blood from oozing, and permits to throw it away sanitarily.

The pocket portion can include a place where a part of a series of wrapping sheet is bent.

According to the wrapping container for individually packaging interlabial pad (hereafter, simply called a wrapping container) according to an implementation of the present invention, the pocket portion is formed by folding a part of a series of wrapping sheets. Therefore, the pocket portion communicates with the other parts of the wrapping container, and a holding capability of the pocket portion to the wrapping container is secured.

Such a wrapping container forms the pocket portion, for example, by folding one lengthwise end part of a series of portrait form wrapping sheets toward the surface (inside) where the interlabial pad is to be placed, and joining both side edges or one side edge where the wrapping sheets overlap each other on each side. Thus, to form the pocket portion, it is preferable to arrange the joined part only in the contact area of the wrapping sheets. Thus, the joined part of the wrapping container is surely maintained at the time of re-housing the used interlabial pad.

In such a constitution, the wrapping sheets can be folded toward the pocket portion in other part where the pocket portion is formed, and it becomes possible to cover the menstrual blood adhering to the pocket portion in the neighborhood of its opening when re-housing the used interlabial pad in the pocket portion, and a risk that menstrual blood may adhere to fingers is reduced.

A wrapping container for individual wrapping of an interlabial pad provided with a mini sheet piece of interlabial pad forming a finger insertion opening, and with the vertical direction, wherein: a vertical direction means is provided for indicating the vertical direction related to the pre-unwrapping portion for unwrapping the wrapping container.

According to the wrapping container for individually packaging interlabial pad (hereinafter, simply called a wrapping container) according to an implementation of the present invention, a top and a bottom of the wrapping container are indicated. Therefore, a wearer can easily grasp the position of the pre-opening part as the place to be unsealed.

As to "an vertical direction indication means" in the present invention, for example, the following means can be mentioned such as a visually checkable means by printing a pattern or characters, etc. on the wrapping container and a finger-touch comprehensible means by arranging ruggedness on the wrapping container by tooling or the like. Here, by using a company emblem (house mark) and a company name instead of the pattern and characters, the wrapping container can also be provided with the effects of advertisement and quality assurance in addition to the above effect (the upper and lower indication of the product).

According to an implementation of the present invention, "the vertical direction related to the pre-opening part" means such a state as the suggestion of the vertical direction seems to indicate the position of the pre-opening part as it is, when there is something like a kind of tendency (for example, the upper part is opened more often or the lower part is opened more often) concerning the place where the upper and lower directional wrapping container is to be opened.

A pre-unwrapping portion can be provided for unwrapping the individual wrapping container, the pre-unwrapping portion is disposed in plurality according to the finger insertion point based on the personal equation of the individually wrapped interlabial and, moreover, the wrapping container is provided with an unwrapping position guide means for guiding the kind of the finger insertion position.

According to the wrapping container for individually packaging interlabial pad (hereafter, simply called a wrapping container) according to an implementation of the present invention, when a plurality of finger insertion openings are arranged for holding the interlabial pad on fingertips, the wrapping container is also provided with plural pre-opening parts corresponding thereto, and a wearer is instructed which pre-opening part to open. Therefore, before opening the wrapping container, the wearer can easily know from the appearance of the wrapping container which pre-opening part should be opened to immediately insert finger in the fingers insertion holes suitable for herself.

As an "opening position instruction means" in the present invention, it may only be such a means as the wearer can grasp the optimal pre-opening part, and for example, printing and coloring of characters and patterns or the like, ruggedness by tooling or the like, etc. arranged in the periphery of the pre-opening part or all the pre-opening parts can be mentioned.

The pre-unwrapping portion for unwrapping the wrapping container can be unwrapped by tearing off a part of the wrapping container along a broken line introducing the position of the pre-unwrapping portion; and the interlabial pad is enclosed so that the finger insertion opening is exposed first, in a state where the pre-unwrapping portion is unwrapped.

According to the wrapping container for individually packaging interlabial pad (hereafter, simply called a wrapping container) according to an implementation of the present invention, the pre-opening parts are formed of broken lines. Namely, such broken lines are provided on the side inner than the part joined for forming the wrapping container, therefore, a wearer does not peel the joined part of the wrapping container but tear a part of the wrapping container along the broken lines, and can thereby unseal such pre-opening part(s) to take out the interlabial pad.

These broken lines have only to show the tearing position and direction to the wearer, and as to the structure, an alternate sequence of slits and non-slits like perforations can be mentioned. The broken lines of such a structure are preferred to have 0.5-5 mm long slit parts, a 3 mm maximum width, and 0.5-3 mm long non-slit parts. Such arrangements can not only guide the direction torn by the wearer not to deviate from the broken lines but can prevent dirt and dust from entering through the broken lines.

Moreover, according to an implementation of the present invention, such broken lines have only to be arranged within the range to form a frontage only permitting to take out the interlabial pad at least.

The breaking strength of the broken line is preferred to be 0.2-3.0 N/25 mm when the broken line is arranged in the center and is pulled in the directions orthogonal to the broken line under the tensile conditions of 25 mm width and 100 mm/min, and more preferably, it is 0.3-1.5 N/25 mm.

In order for a wearer to visually grasp the broken line with ease, a starting point of the broken line can be provided with a printed arrow or a section in the neighborhood of the starting point different from that for the end part (for example, the end part is rounded etc.).

Moreover, by forming the wrapping container gradually wider in the direction of the starting point of the broken line and narrower in the opposite direction on the other hand, it is also possible to attach the mini-sheet piece for the wrapping container so that the finger insertion opening(s) is positioned in the direction opposite to the direction in which the wrapping container is formed wider. In such a manner, when a wearer handles the wrapping container enclosing the interlabial pad therein, it is possible to induce the wearer to take the narrower-formed side of the wrapping container by the hand, therefore, the wearer is able to insert her fingers in the finger insertion opening(s) provided in the wrapping body without changing the direction of the wrapping container. Further, the wearer can smoothly insert her finger(s) in the finger insertion opening(s) without changing the direction of the interlabial pad as well as the wrapping container by arranging the finger insertion opening(s) also to be faced in the same direction as the finger insertion opening(s) of the wrapping container.

Moreover, to reduce misconception of an opening action of the pre-opening part, the joined part of the wrapping container positioned outside of the broken lines is preferred to be increased in joining strength beforehand.

The wrapping container for individually wrapping an interlabial pad can be composed of a laminate material having fiber sheet at the inner face side, and film sheet on the outer face side.

According to the wrapping container for individually packaging interlabial pad (hereafter, simply called a wrapping container) according to an implementation of the present invention, the wrapping container is constituted of the laminated materials of a fiber sheet for the inside surface side and a film sheet for the outside surface side. Therefore, the wrapping container can be made excellent in wiping property and anti-liquid property.

As detailed materials to be placed in the "inside surface side," the following materials can be mentioned considering the requirements that the materials permit to smoothly pull out the interlabial pad from the wrapping container and they should have hydrophilic property, fiber density and soft feeling, etc. For example, they are; wet spun lace nonwoven fabric which is a mixture of crepe tissue of 15-50 g/m$^2$ and cotton and pulp and is obtained in the range of 15-70 g/m$^2$ by adjusting the cotton at 10% wt at least, spun lace nonwoven fabric obtained in the range of 20-70 g/m$^2$ by adjusting rayon fiber at 30% wt at least, melt blown nonwoven fabric composed of polypropylene obtained in the range of 20-50 g/m$^2$, composite nonwoven fabric composed of spunbond, melt blown, and spun bond ranging 6-10 g/m$^2$, 5-20 g/m$^2$, and 6-10 g/m$^2$ by weight, respectively, etc.

As detailed materials to be placed on the "outside surface side," considering water resisting property, a polyethylene film obtained in the range of 10-30 g/m$^2$, and an open hole plastic sheet with an open hole rate of 10-30% adjusted to the range of 15-30 g/m$^2$ can be mentioned.

The materials for the inside surface side and outside surface side are laminated by means of known techniques such as hot melt adhesive, heat embossing, and ultrasonic sealing.

Considering the feeling, it is preferable in such laminating that a coating quantity is made within a range of 3-10 g/m$^2$ and the laminating is performed within a 5-40% coating area in a spiral or striped form arrangement in the case of a hot melt adhesive, and that the laminating is performed within a 5-20% sealing area in an arrangement in dotted, linear, crossover line form, etc. in the case of heat or ultrasonic sealing.

The wrapping container for individually wrapping an interlabial pad can be composed of a biodegradable material and/or water-soluble material and/or water dispersible material.

According to the wrapping container for individually packaging interlabial pad (hereafter, simply called a wrapping container) according to an implementation of the present invention, the composition materials are a biodegradable material and/or a water-soluble material and/or a water-dispersible material. Therefore, when the wrapping container is made of the water-soluble material or the water-dispersible material, a wearer can throw it into the toilet bowl, therefore, the wearer is relieved from the trouble of the disposal, and also it is possible to reduce rubbish in the toilette.

As detailed examples of such a wrapping container, a composite material laminating tissue adjusted to a 15-40 g/m$^2$ specific weight per unit area and polyvinyl alcohol of a 20-50 g/m$^2$ specific weight per unit area and coated with silicone within a range of 0.5-1 μm on the side of polyvinyl alcohol, spun bond nonwoven fabric of poly-lactic fiber as a main substance adjusted to a 15-40 g/m$^2$ specific weight per unit area, etc. can be mentioned.

Moreover, the interlabial pad enclosed in such a wrapping container is preferred to be biodegradable, water-soluble, and water-dispersible. Such arrangements make it possible to throw away an used interlabial pad into the toilet bowl, therefore, the used interlabial pad can easily and sanitarily be disposed. And, since the interlabial pad can be thrown away into the toilet bowl together with the wrapping container, the arrangement have another effect of further reducing rubbish in the toilet.

Here in this specification, the "biodegradability" means that a substance is degraded into gases like carbon dioxide, methane, etc., water, and biomass according to the process of the nature under the existence of bacteria starting with ray fungi and other microorganisms under an anaerobic or aerobic condition, and that the biodegradability (biodegradable rate, biodegradable degree, etc.) of the substance compares with a naturally produced material like fallen leaves or the like or synthetic polymer generally recognized as biodegradable in the same environment. The "water dispersibility" means as same as water degradability, meaning such a property as a substance is not influenced by a limited quantity of water (menstrual blood) when used but the fibers are easily dispersed into small pieces to such a limit as they do not cause clogging ordinary toilet wiping with themselves at least in a large quantity of water or water current. The "water solubility" means such a property as the substance is not influenced by a limited quantity of water (menstrual blood) when used but dissolved in a large quantity of water or water current.

A wrapping body, including an interlabial pad provided with a mini sheet piece for interlabial pad forming a finger insertion opening where an opening of fingerbreadth is secured and a finger insertion space following the same, and a wrapping container for individually wrapping an interlabial pad for individually wrapping the interlabial pad, The interlabial pad is enclosed as folded so that the finger insertion opening opens when the pre-unwrapping portion is opened in order to open the wrapping container.

According to the wrapping body according to an implementation of the present invention, the interlabial pad is folded so that the finger insertion opening(s) provided with the interlabial pad are opened, and enclosed in the wrapping container for individually wrapping interlabial pad (hereafter, simply called wrapping container).

Regarding this point, a sheet-like sanitary product such as a napkin generally encloses the content folded therein for making the wrapping body compact, however, according to an implementation of the present invention, the folded interlabial pad is opened as the wrapping container for individual interlabial pad is opened, and this makes a gap between the mini-sheet piece and the back sheet of the interlabial pad and the wrapping container will thus have an another effect of naturally forming the finger insertion opening(s) in addition to such compact-making.

As such a folding method, for example, the interlabial pad is folded along the approximately longitudinal center line of the interlabial pad with the surface with the mini-sheet piece of the interlabial pad faced inside.

The interlabial pad can be contained, so that the mini sheet piece for the interlabial pad is folded toward the opposite side to the body side along the substantial central line in the longitudinal direction of the interlabial pad.

Moreover, according to an implementation of the present invention, the meaning of "so as to be folded toward opposite side to the body side" includes not only the case that it is completely folded to be convex toward opposite side to the body side but also the case that it is curved to be convex toward opposite side to the body side.

A wrapping body includes an interlabial pad provided with a mini sheet piece for interlabial pad forming a finger insertion opening where an opening of fingerbreadth is secured and a finger insertion space following the same, and a wrapping container for individually wrapping an interlabial pad for individually wrapping the interlabial pad. The interlabial pad is contained in a direction orthogonal to the wrapping container for individually wrapping an interlabial pad.

In the wrapping body according to an implementation of the present invention, the opening direction and the finger insertion direction can be made the same to a wearer by wrapping the interlabial pad provided with anisotropy to the wrapping container, the arrangement makes easier for the wearer to insert her fingers therein.

In this case, the interlabial pad can be packaged, for example, with the mini-sheet piece faced to the outside and along the longitudinal center part folded almost in half (refer to FIG. 39(A)).

A wrapping body, includes an interlabial pad provided with a mini sheet piece for interlabial pad forming a finger insertion opening where an opening of fingerbreadth is secured and a finger insertion space following the same and a wrapping container for individually wrapping an interlabial pad for individually wrapping the interlabial pad. The interlabial pad is contained so that the finger insertion opening in the interlabial pad to be contained is positioned near the pre-unwrapping portion for unwrapping the wrapping container for individually wrapping an interlabial pad.

According to the wrapping body according to an implementation of the present invention, the interlabial pad is placed so that the mini sheet piece for the interlabial pad can be positioned in the neighborhood of the pre-opening part of the wrapping container. As a result, the finger insertion opening(s) of the interlabial pad is positioned in the neighborhood of the pre-opening part, and after opening the pre-opening part, the fingers can promptly be inserted in the finger insertion openings to hold the interlabial pad by the fingertips, therefore, it is possible to further reduce time to fix the interlabial pad.

A wrapping container for individual wrapping of sanitary napkin, wherein: the wrapping container is provided with a pocket portion for enclosing interlabial pad in order to enclose a used interlabial pad.

Especially, when the interlabial pad is constituted of a degradable material, a water-soluble material, or a water-dispersible material, the interlabial pad can be disposed into the toilet bowl together with the wrapping container by constituting also the materials forming the wrapping container the wrapping sheet and the pocket portion from the degradable material and/or the water-soluble material and/or the water-dispersible material, therefore, the handiness of disposal is improved.

Moreover, by packaging both a sanitary napkin and an interlabial pad in the wrapping container, a wearer has only to carry a single wrapping container to use both of them together, therefore, the package becomes excellent in portability.

Next, the embodiments of the present invention will be explained referring to the drawings.

[Interlabial Pad Individual Wrapping Container Separable to Two Sections]

First Embodiment

Figure 3:
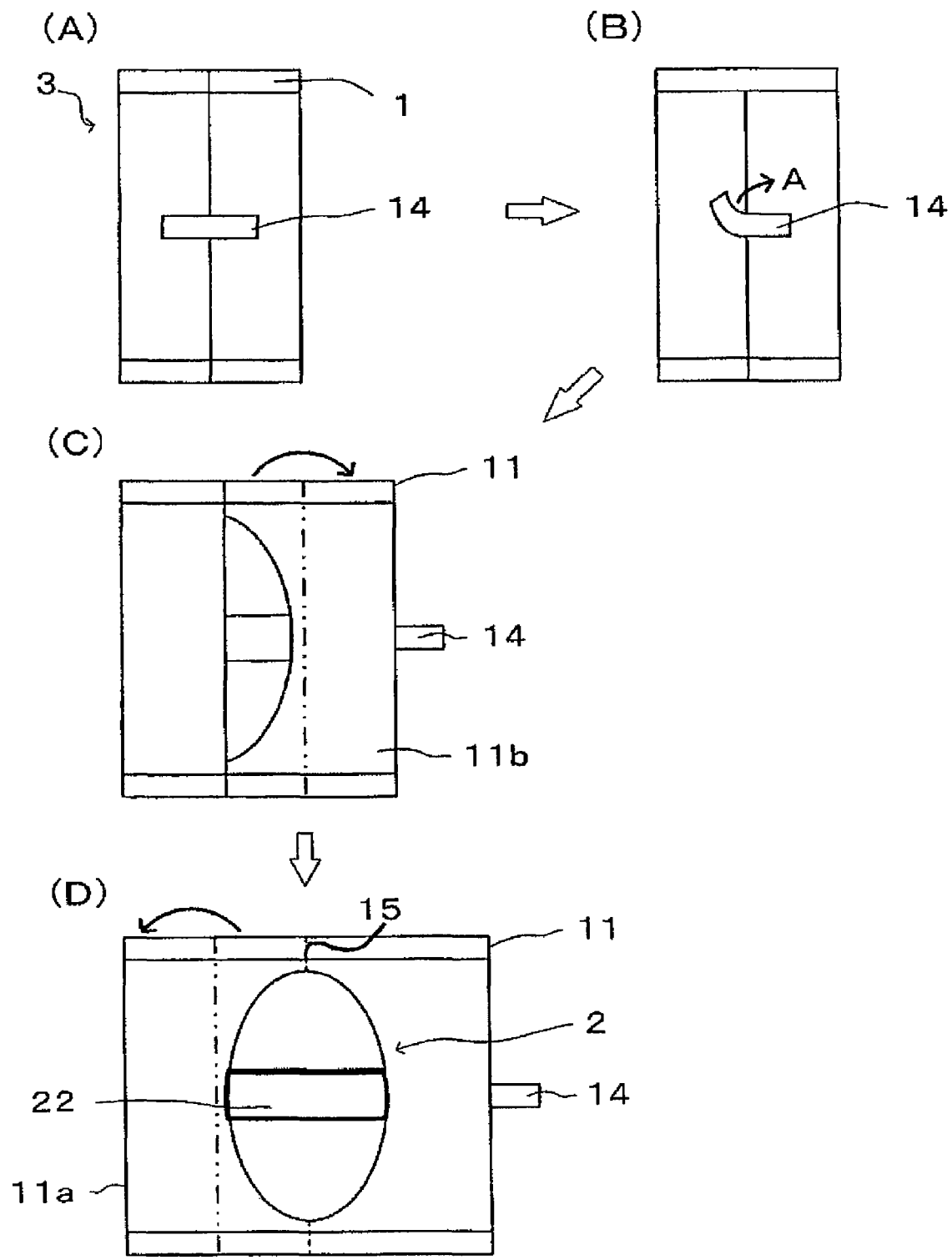
FIG. 3(A)-(D) illustrate a procedure for opening the pre-unwrapped opening of the interlabial pad individual wrapping container in accordance with the first embodiment.
Figure 4:
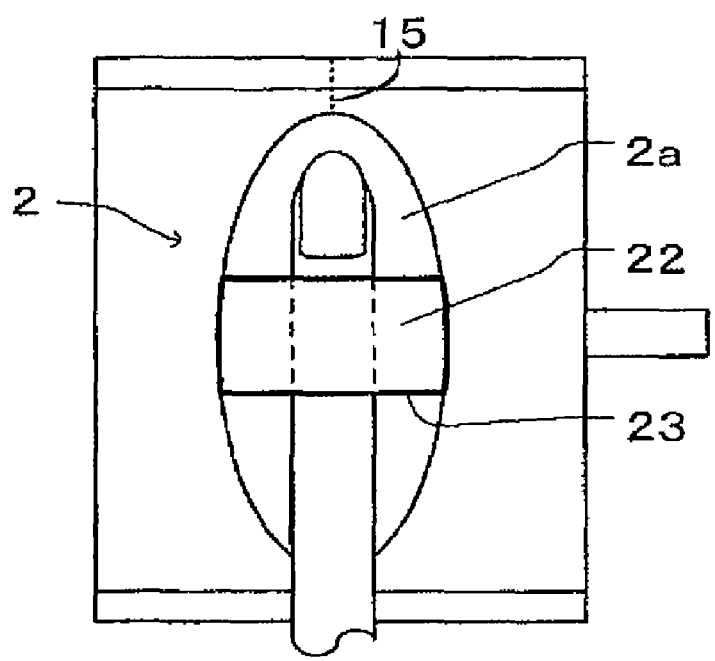
FIG. 4 illustrates a state of finger insertion in the mini-sheet piece for the interlabial pad fixed to the interlabial pad in accordance with this embodiment.

Firstly, the structure of the interlabial pad individual wrapping container (hereafter, simply called wrapping container) provided with mini-sheet for the wrapping container will be explained. FIGS. 1(A)-(D) illustrate a process for forming a wrapping body 3 by folding the wrapping body 11 for the wrapping container 1 while enclosing the interlabial pad 2 therein; FIG. 2 is a sectional view taken along the arrow line I-I of FIG. 1(D); FIG. 3 is a process drawing showing a method for opening the wrapping container; and FIG. 4 is a drawing showing a state in which an index finger is inserted in a belt body 22 which is a mini-sheet piece for the interlabial pad.

As shown in FIG. 1(A), the interlabial pad 2 is firstly placed with the opposite side face to body side face 2a. Next, as shown in (B) of the same figure, one side part 11a of the wrapping sheet 11 is folded inside along the longitudinal side edge part of the interlabial pad 2, and further, as shown in (C) of the same figure, the other end part 11b of the wrapping sheet 11 is also folded inside. Thus, as shown in (D) of the same figure an overlapping part 11c of the side part 11a and the side part 11b is formed, and this overlapping part becomes the pre-unwrapped opening. This overlapping part 11c is sealed with a peelable stop tape 14. And, by temporary tacking the upper and lower edges of the wrapping sheet by means of heat-sealing, ultrasonic-sealing, etc., so as to be unsealed again, the interlabial pad 2 is enclosed so as not to fall out and thus the wrapping body 3 is formed.

In the wrapping body 3, as shown in FIG. 2, the belt body 22 fixed on the interlabial pad 2 is positioned directly under the overlapping part 11c formed by the overlap of the side parts 11a, 11b of the wrapping sheet 11. Therefore, a wearer can immediately find the belt body 22 by opening the overlapping part 11c and can insert a finger in the finger insertion opening 23.

To open the wrapping body 3 shown in FIG. 3(A), the stop tape 14 is firstly picked up and pulled in the direction of A. Thus, the side part 11b of the wrapping sheet 11 is opened outward as shown in (C) of the same figure. Following this, as shown in (D) of the same figure, the other side part 11a of the wrapping sheet 11 is also opened outward, and thereby the belt body 22 fixed on the interlabial pad 2 can be exposed. Therefore, a wearer can easily find the belt body 22 without turning over the interlabial pad 2.

Then, as shown in FIG. 4, the wearer inserts the index finger or middle finger of her dominant hand (usually right hand) in the finger insertion opening 23 formed from the exposed belt body 22 so that the ball of the finger comes in contact with the opposite side face to body side face 2a of the interlabial pad 2, to hold the interlabial pad 2 on the fingertip.

Figure 7:
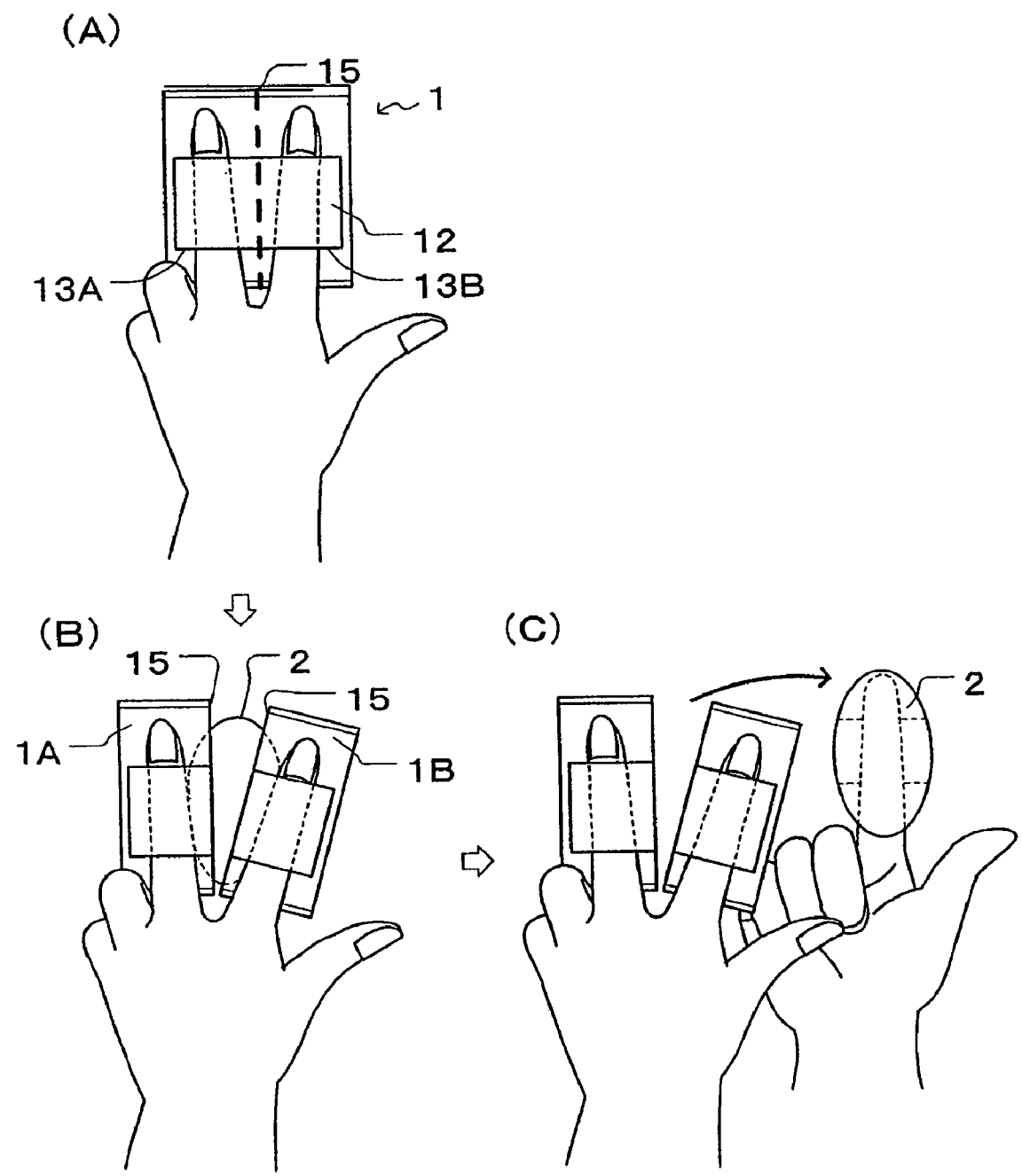
FIGS. 7(A)-(D) illustrate a method for separating the wrapping container for individually wrapping an interlabial pad along the broken line in accordance with the first embodiment.

Next, the mini-sheet piece for the wrapping container fixed on the wrapping container, and a method for separating the wrapping container by using the same will be explained. FIG. 5 shows the rear face of FIG. 3, and shows the views of the wrapping container 1 provided with a broken line 15 and a section part 17 which are the separation part for separating the belt body 12, which is the mini-sheet piece for the wrapping container, from the wrapping container 1, and FIG. 6 is a drawing showing another mode of the belt body 12, and FIG. 7 is a process drawing for showing a process of taking out the interlabial pad 2 by separating the wrapping pad 1 therefrom.

As shown in (A) of FIG. 5, the wrapping container 1 is provided with the broken line 15 in the center. And, the belt body 12, which is the mini-sheet piece for the wrapping container, is fixed thereon striding over this broken line 15. As shown in (B) of FIG. 5, a sectional view taken along the arrow line II-II of FIG. 5(A), the joining of this belt body 12 is performed with an adhesive 16 applied to the three points in total, which are both right and left side parts of the belt body 12 and the part along the broken line 15. The belt body 12 fixed in such a manner forms finger insertion parts 13A and 13B, and a wearer inserts two fingers of her non-dominant hand (usually left hand) in these finger insertion openings 13A and 13B, and can thereby hold the wrapping container 1 on the fingertips.

Here, the broken line 15 makes the separation parts in this embodiment, however, as shown in FIG. 5(C), the wrapping container 1 can be separated by providing the wrapping container 1 with a section part 17 on the upper part thereof for starting the separation with this. Moreover, as shown in FIG. 5(D), both of the broken line 15 and the section part 17 may be arranged.

Moreover, as shown in FIG. 6(A), two pieces of belt bodies 12 can symmetrically be arranged holding the broken line 15 in-between. Since the belt body 12 does not exist on the broken line 15 in such a manner, the breaking strength can be made almost constant at the time of separating the wrapping container 1 by tearing the broken line 15. Therefore, the wrapping container 1 shown in FIG. 6(A) can be divided more stably than the wrapping container 1 shown in FIG. 5(A).

Moreover, in this case, as shown in FIG. 6(B), a sectional view taken along the arrow line III-III of FIG. 6(A), the adhesive 16 is applied to the respective side edges of the two belt bodies 12, therefore, the adhesive 16 needs to be applied to four application areas in total.

Both of the belt bodies 12 are arranged to be of the same dimensions as shown in FIG. 6(A), but can be arranged to be of different dimensions as shown in (C) of the same figure. For example, as shown in (D) of the same figure, it is possible to induce a wearer to insert her middle finger in the finger insertion opening 13A, and her index finger in the finger insertion opening 13B by making the longitudinal lengths different from each other.

To divide the wrapping container 1, as shown in FIG. 7(A), firstly, two fingers, the index finger and middle finger of the left hand, are inserted in the finger insertion openings 13A and 13B formed holding the broken line 15 in-between, respectively. Next, as shown in (B) of the same figure, the two fingers are opened to the left and right. The wrapping container 1 is the torn along the broken line 15 to the left and right by this release force and the sections 1A and 1B are separated. And, the wearer can take out the interlabial pad 2 from the wrapping container 1 by moving the right hand holding the interlabial pad 2.

Figure 8:
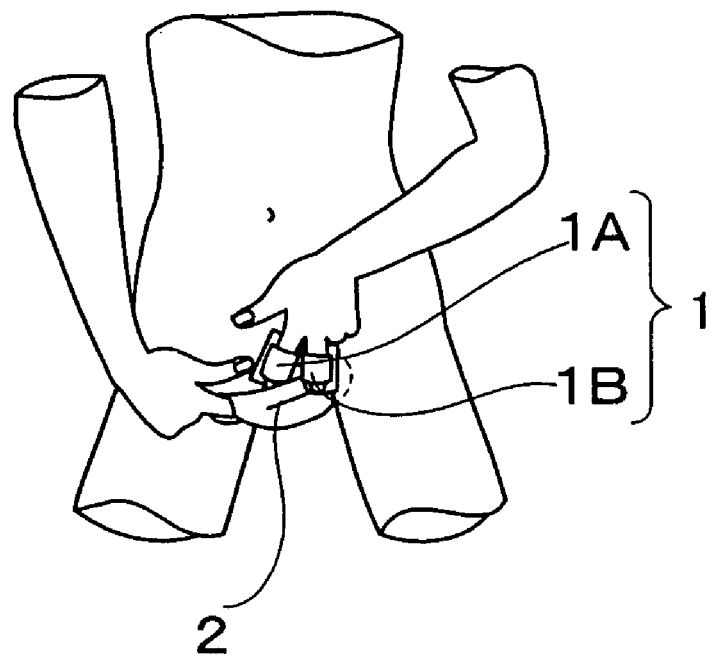
FIG. 8 is an explanatory drawing for explaining a state of fixing the interlabial pad by using the separated sections of the wrapping container for individually wrapping an interlabial pad in accordance with the first embodiment.

Then, as shown in FIG. 8, while opening the interlabial by the fingers of the left hand which are holding the sections 1A and 1B of the wrapping container 1, the wearer can fix the interlabial pad 2 held on the index finger of the right hand in the labia. Therefore, such a situation never occurs, as the fingers come in contact with the labia and menstrual blood during fixing action.

Figure 58:
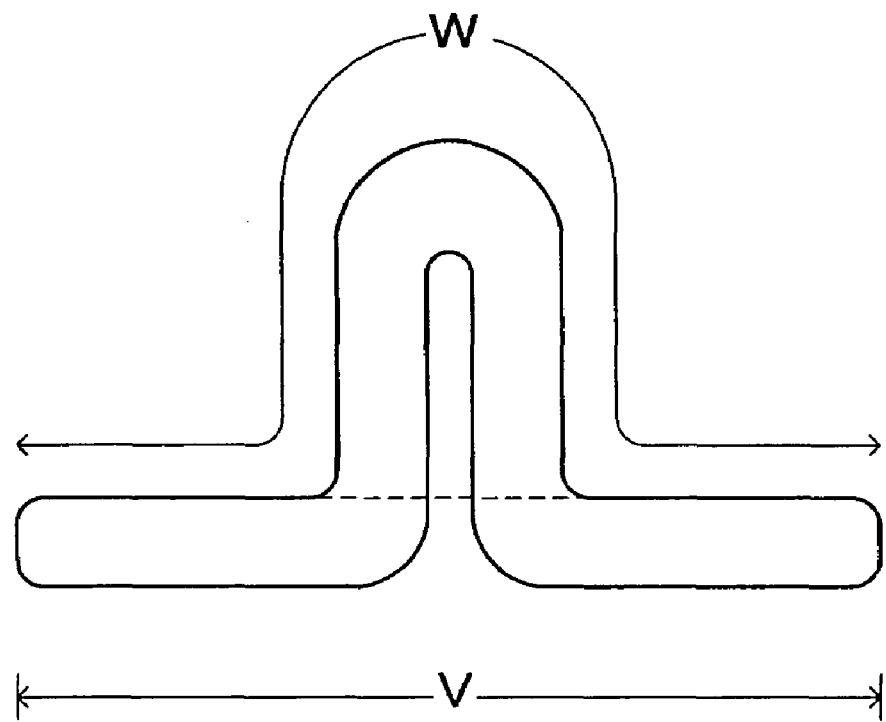
FIG. 58 is an explanatory drawing explaining the length dimensions of the interlabial pad in the widthwise direction.

In this embodiment, the dimensions of the interlabial pad 2 are such as can put into the labia without difficulty and can also be held by fastening force of the labia themselves, and further, the blocking property of the labia is also considered. Concretely, the longitudinal dimension is 60-150 mm, and the outward widthwise length of the interlabial pad is preferred to be 10-60 mm, more preferably, it is recommended to be in a range of 20-40 mm. When the widthwise length exceeds 60 mm, the region not lying between the labia rubs the femoral region etc. of the wearer and the friction force caused thereby exceeds the holding force of the labia, and the interlabial pad is in danger of falling out. Moreover, when widthwise length is shorter than 10 mm, the region capable of lying between the labia decreases and a touch area with the inner face of the labia decreases, and the interlabial pad is apt to fall out. Here, the above-mentioned "outward" means that the length is the shortest distance between the two points corresponding to V in FIG. 58). This is carefully defined because the way tracing the convex and concave form between the two points, namely, the distance between the two points in the state in which the convex and concave form is developed and flattened is sometimes treated as an actual distance (corresponding to W in FIG. 58) associated with the manufacturing process. Moreover, the thickness dimension is arranged in a range of 2-10 mm considering a comfort feeling without extremely damaging the feeling of wearing.

Considering such a filling property of the interlabial pad and a fitting property of the belt body 12, it is preferable that the lengthwise dimension is in a range of 80-170 mm and the widthwise dimension is in a range of 60-90 mm.

Moreover, it is necessary that the widthwise dimension of the belt bodies 12 are arranged so as not stick out of the width of such a wrapping container 1, and have a 25 mm width at least so that the width permits to insert two fingers in the two finger insertion openings 23A and 23B. Concretely, the width is preferred to be in a range of 25-80 mm.

Moreover, the lengthwise dimension of the belt body 12 may be at least 30 mm or longer, and it may be elongated up to the end of the wrapping container 1 unless it is in a range of sticking out of the wrapping container 1.

Second Embodiment

Figure 10:
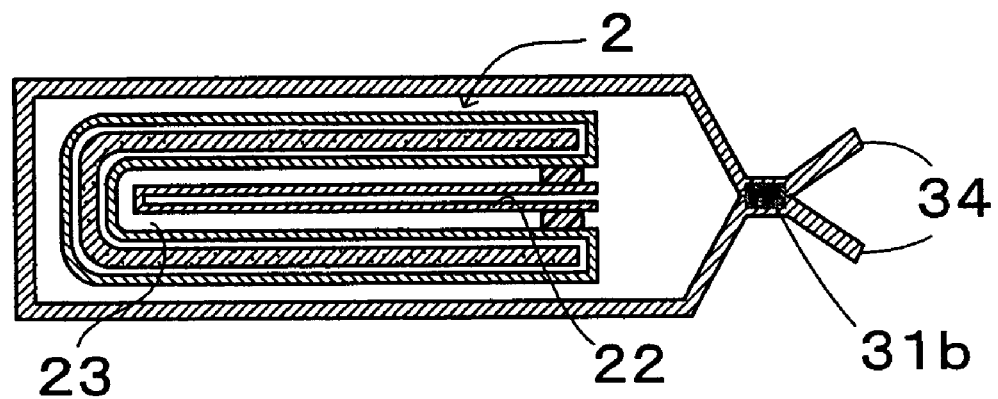
FIG. 10 is a sectional view taken along the arrow line IV-IV of FIG. 9(C).
Figure 11:
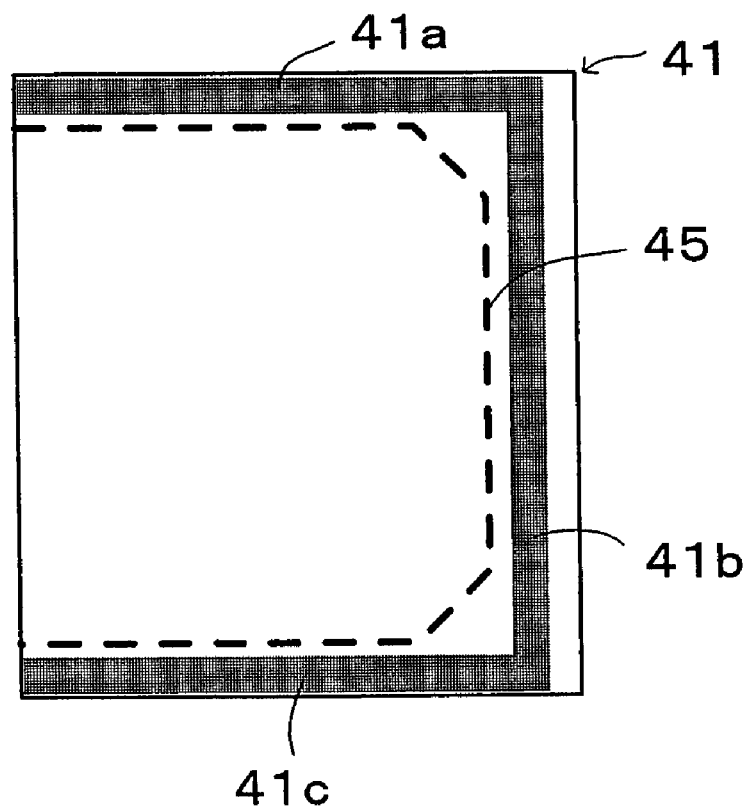
FIG. 11 is a drawing showing another constitution of the wrapping container for individually wrapping an interlabial pad in accordance with the second embodiment, and shows a mode in which the pre-unwrapped opening is formed from a broken line.
Figure 13:
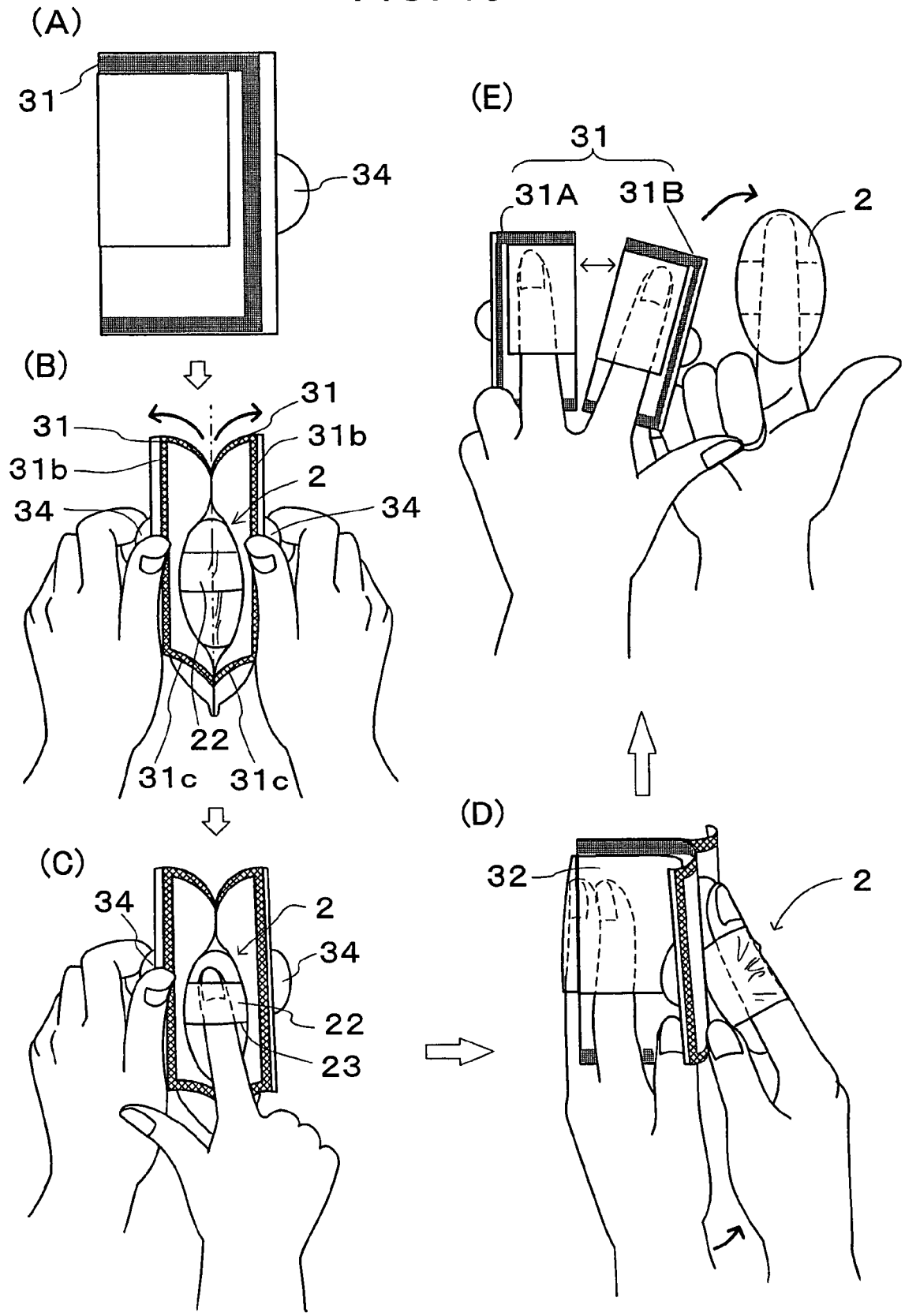
FIGS. 13(A)-(E) illustrate a method for opening the pre-unwrapped opening of the wrapping container for individually wrapping an interlabial pad in accordance with the second embodiment, and shows also a method for separating the wrapping container for individually wrapping an interlabial pad.

Next, a wrapping container provided with a mini-sheet piece for the wrapping container and folded in two will be explained. FIG. 9 is a process drawing illustrating the processes for forming the wrapping body 33 by containing the interlabial pad 2 in the wrapping container 31; FIG. 10 is a sectional view taken along the arrow line IV-IV of FIG. 9(C); FIG. 11 illustrates the wrapping container 41 on which the pre-unwrapped opening is formed from the broken line 45; FIG. 12 illustrates a wrapping container 51 formed by sticking two wrapping sheets 51A and 51B together; and FIG. 13 is a process drawing illustrating a method for opening the wrapping container 31 and taking out the interlabial pad 2, and also separating the wrapping container 31 into two sections 31A and 31B.

In order to form the wrapping body 33, as shown in FIG. 9(A), the interlabial pad 2 is folded along the vertical axis so that the left and right side edges overlap each other. In this case, the interlabial pad is folded with the opposite side face to body side face 2a inside, where the belt body 22, the mini-sheet piece for the interlabial pad, is fixed.

Next, as shown in (B) of the same figure, the folded interlabial pad 2 is placed on the right side of the wrapping sheet 31, and then the wrapping sheet 30 is folded in half centering the vertical axis of the wrapping sheet 30, to cover the interlabial pad 2. Following this, as shown in (C) of the same figure, joining parts 31a, 31b, 31c are arranged on the overlapping part for forming the pre-opening part, to make the wrapping body 33 by joining each of them. However, the tab 34 is not joined in this case. As a result, the belt body 32, which is the mini-sheet piece for the wrapping container, is to be placed on the surface of the wrapping body 33.

Inside this wrapping body 33, as shown in FIG. 10, the belt body 22 is positioned opposite to the joining part 31b. Therefore, peeling this joining part 31b to open the wrapping body, a wearer can immediately recognize the belt body 22.

In this embodiment, the pre-unwrapped opening of the wrapping container 31 is formed from the joining parts 31a, 31b and 31c joined by heat-sealing permitting re-peeling thereof, however, the pre-unwrapped opening can also be formed from the broken line 45 arranged inside the joining parts 41a, 41b, 41c as that on the wrapping container 41 shown in FIG. 11. It is possible to form an unwrapped opening by opening the pre-unwrapped opening by cutting out the end part of the wrapping container 41 along this broken line 45.

According to the embodiment shown in FIG. 11, the interlabial pad 2 is covered by a single wrapping sheet, however, as the wrapping container 51 shown in FIG. 12(A), two wrapping sheets 51A and 51B are used, and the interlabial pad 2 is placed in-between, and then both of the wrapping sheets 51A and 51B are stuck together by joining the four joining part 51a, 51b, 51c and 51d. In this case the broken line 55 is inside the joining parts 51a, 51b and 51c.

The wrapping container 31 in this embodiment has two tabs 34 as shown in FIG. 13(A). Therefore, as shown in (B) of the same figure, a wearer can open the wrapping container sequentially from the joining part 31b to the joining parts 31a, 31c by pulling the tabs 34 to the left and right, and can expose the belt body 22 attached to the interlabial pad 2. Next, as shown in (C) of the same figure, the index finger of the right hand is inserted in the finger insertion opening 23 formed from the body 22. Then, as shown in (D) of the same figure, the index finger and middle finger of the left hand are inserted into the belt body 32 of the wrapping container, to fix the wrapping container on the left hand.

In this state, the wearer can take out the interlabial pad 2 from the wrapping container 31 by raising the right hand to the upper right. Following this, as shown in (E) of the same figure, the wrapping container 31 can be separated in to the sections 31A and 31B by opening the index finger and the middle finger to the left and right. Thus, while the wearer is opening the labia using the sections 31A and 31B held on the fingers of the left hand, she can fix the interlabial pad 2 held on the right hand at an appropriate position in the labia.

Third Embodiment

Figure 14:
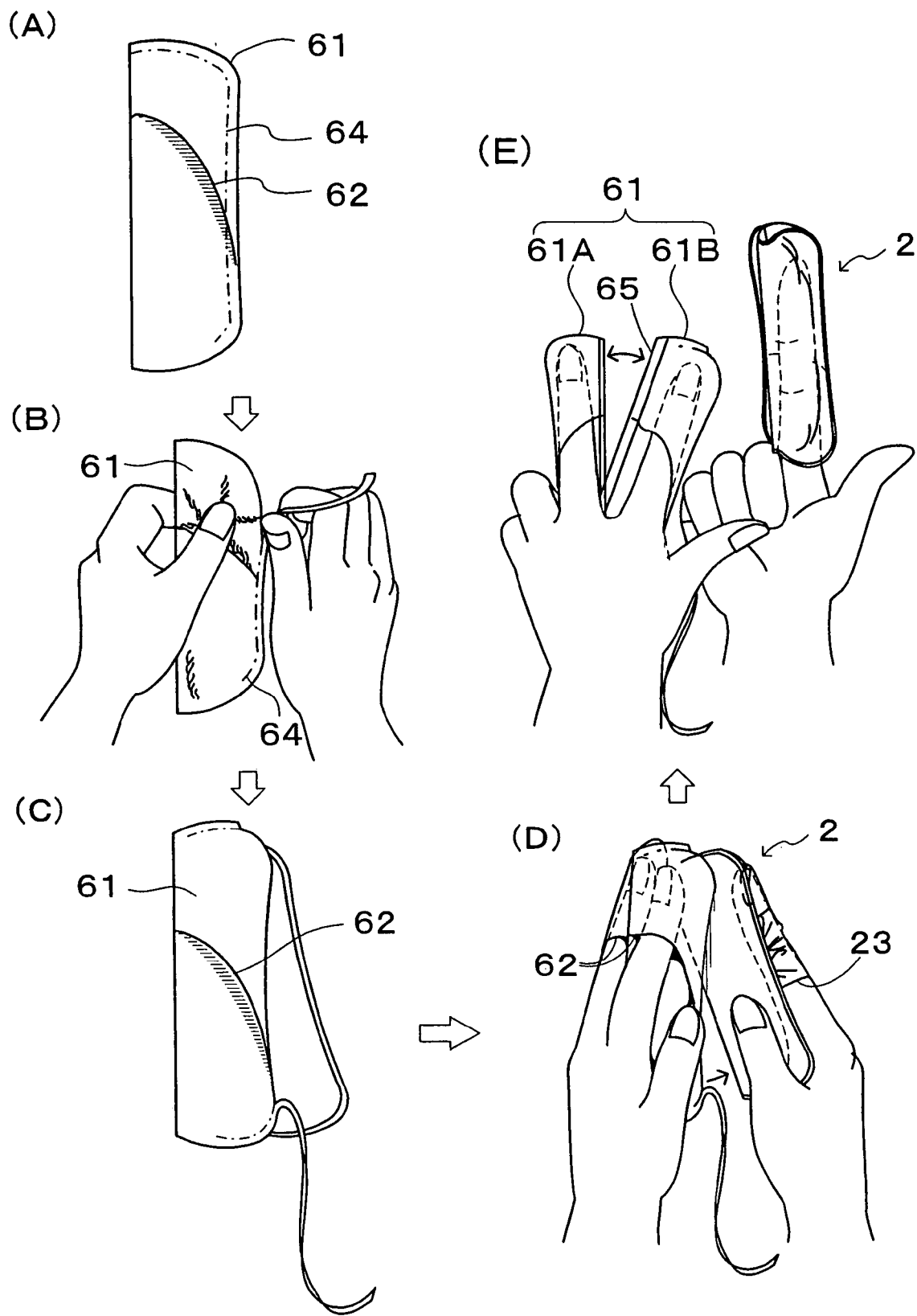
FIGS. 14(A)-(E) illustrate a method for opening the broken line forming the pre-unwrapped edge in the wrapping container for individually wrapping an interlabial pad in accordance with the third embodiment and a method for separating the wrapping container for individually wrapping an interlabial pad.

Next, a pod-like wrapping container having a finger cot on the side will be explained. FIG. 14 is a process drawing showing a method for opening a pod-like wrapping container 61, taking out the interlabial pad 2, and separating the wrapping container 61 into two sections 61A and 61B at the same time.

As shown in FIG. 14(A), the wrapping container 61 is provided with a broken line 64 for forming a pre-unwrapped opening. Therefore, as shown in (B) of the same figure, a wearer opens the wrapping container 61 by tearing off a part of the wrapping container 61 along the broken line 64 as shown in (C) of the same figure. Following this, as shown in (D) of the same figure, the wearer inserts her index finger and middle finger of the left hand in the two respective finger cot parts provided on both side faces of the wrapping container 61, while she inserts her index finger of the right hand in the finger insertion opening 23 of the interlabial pad 2. In this state, she can take out the interlabial pad 2 from the wrapping container 61 by moving the right hand. Further, as shown in (E) of the same figure, the wearer can separate the wrapping container 61 into the sections 61A and 61B apart along the separation edge 65 by opening the index finger and the middle finger of the left hand to the left and right. While opening the labia using these sections 61A and 61B, the wearer can put the interlabial pad fixed on the right hand at an appropriate position in the labia.

Fourth Embodiment

Figure 15:
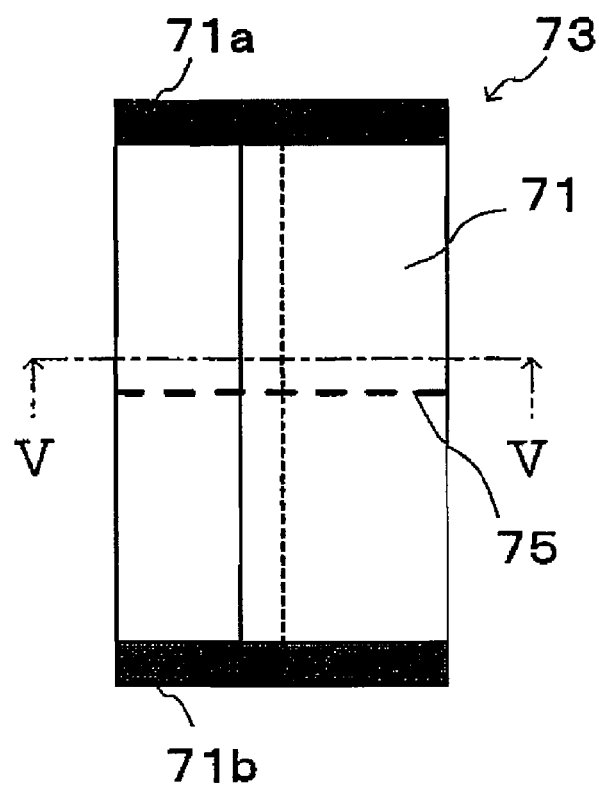
FIG. 15 shows a drawing which illustrates the wrapping container for individually wrapping an interlabial pad in accordance with the fourth embodiment.
Figure 16:
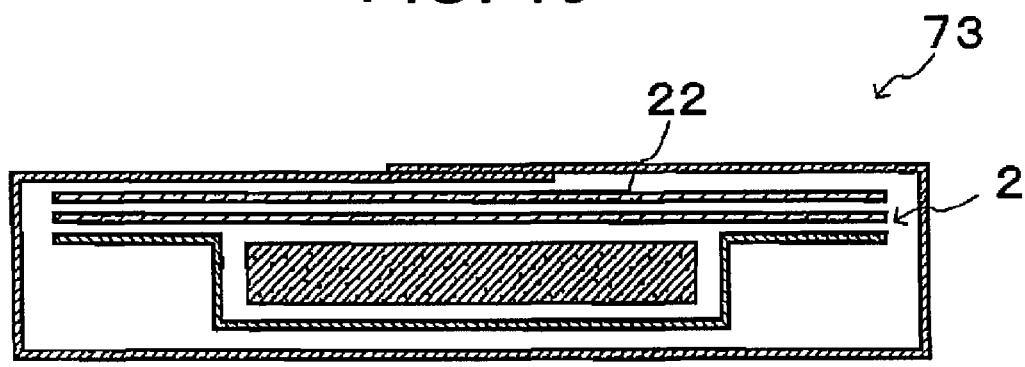
FIG. 16 is a sectional view taken along the arrow line V-V of FIG. 15.
Figure 18:
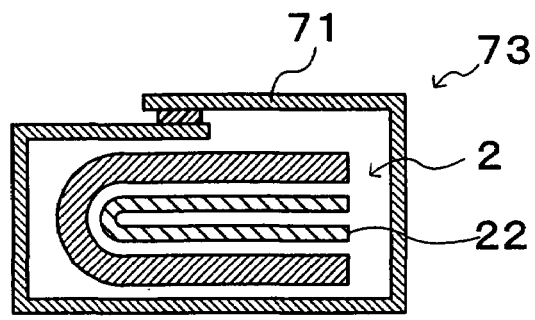
FIG. 18 is a longitudinal sectional view of the wrapping body illustrating the interlabial pad folded and enclosed therein.
Figure 19:
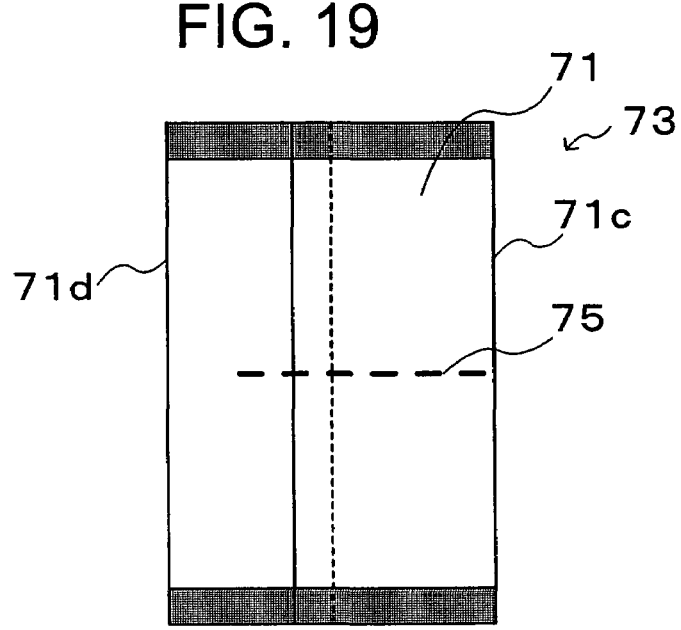
FIG. 19 is a drawing illustrating another constitution of the wrapping container for individually wrapping an interlabial pad in accordance with the fourth embodiment, where the broken line started from one side part is not extended on the other side part.
Figure 20:
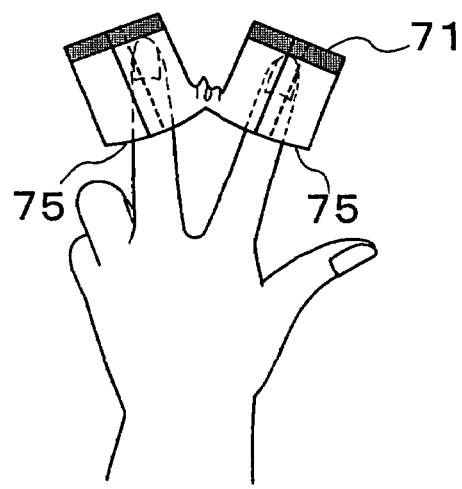
FIG. 20 is a drawing illustrating a state in which the fingers are fixed by breaking the wrapping container for individually wrapping an interlabial pad along the broken line thereon shown in FIG. 19.

Next, the wrapping container which itself serves as finger cots will be explained. FIG. 15 is a drawing for illustrating the wrapping container 71 provided with a broken line 75 about in the longitudinal middle area; FIG. 16 is a sectional view taken along the arrow line V-V of FIG. 15; FIG. 17 is a process drawing illustrating the state of fixing the sections 71A, 71B on the fingertips formed by separating the wrapping container 71 by opening it; FIG. 18 is a longitudinal sectional view of the wrapping body 73 containing the interlabial pad 2 in folded state; FIG. 19 is a drawing for showing the wrapping body 73 in which the broken line 75 staring from one side part 71c of the wrapping container 71 is not extended up to the other side part 71d; and FIG. 20 illustrates the state in which the wrapping container of FIG. 19 is separated from the broken line 75 and is fixed on the fingertips.

The wrapping body 73 shown in FIG. 15 is constructed by covering the interlabial pad 2 (not illustrated) provided with the belt body 22, making both longitudinal end parts of the rectangular wrapping sheet overlap each other to form it into a cylindrical form, joining the overlapping parts of this wrapping body 71 and the upper and lower edge ends, respectively, and enclosing the interlabial pad 2 therein. And, the wrapping container 71 is provided with a broken line 75 so as to be separated into two in the widthwise direction about in the lengthwise central region.

The overlapping parts of the wrapping sheet are joined with a hot melt type adhesive, hot air sealing, etc., and the top and bottom end edges are joined by heat-sealing, ultrasonic sealing or a combination of heat-sealing and hot melt type adhesive, etc.

As shown in FIG. 16, the wrapping body 73 is formed by wrapping the belt body 22 with the interlabial pad 2 in the wrapping sheet in the lengthwise direction. Moreover, the overlapping parts of the wrapping sheet is positioned on the opposite side to the body side on which the belt body 22 is fixed in this embodiment, but may be positioned on the body side.

Moreover, it is preferable that both of the fore and aft end edges of the wrapping container 71 are roundly edged and not acute. If both of the fore and aft end edges are acute, the labia may be harmed, however, the form as mentioned above reduces stimulation to labia at the time of opening the labia using the wrapping container 71.

To open the wrapping container 71 forming the wrapping body 73 shown in (A) of FIG. 17, as shown in (B) of the same figure, the wrapping container 71 is firstly separated into the sections 71A and 71B along the broken line 75. Thus, the wrapping container 71 is opened, and the interlabial pad 2 is exposed. Therefore, as shown in FIG. 17(C), it is possible to hold the interlabial pad 2 on the fingertip by inserting the index finger of the right hand in the finger insertion opening 23. And, when the wrapping container 71 is separated, the top and bottom parts 71a and 71b thereof are kept joined, therefore, the sections 71A and 71B are of a sack form. Therefore, as shown in (D) of the same figure, the sections 71A and 71B can be fixed on the fingertips like finger cots by inserting the fingers in the openings broken along the broken line 75, and when the interlabial pad 2 is fixed in the labia, the labia and the fingers are prevented from touching each other by opening the labia by the fingertips in such a state. Thus, the wrapping container 71 is used at the time of fixing the interlabial pad 2, therefore, the fixing action is performed sanitarily and smoothly without so much waste thrown away as in the case of putting on finger cots separately.

Moreover, as shown in FIG. 18, the interlabial pad 2 can be enclosed also in a folded state. In this case, the interlabial pad 2 is preferred to be folded so that a half of the opposite side face to body side face, where the belt body 22 is attached approximately along the center line of the longitudinal axis, is faced to the other half thereof. By folding the interlabial pad as the above, the wearer can visually check the body side for wearing the pad between the labia as soon as she opens the wrapping container 71, and she can wear the pad smoothly.

As shown in FIG. 17(A), the broken line 75 to be provided on the wrapping container 71 is arranged from one side part 71c toward the other side part 71d approximately in the longitudinal center of the wrapping container 71, however, as shown in FIG. 19, the broken line 75 starting from one edge part 71c may be so arranged that it is not extended up to the other edge part 71d but ends in the neighborhood of the edge part 71d. In this case, to open the wrapping container 71, the break according to the broken line 75 is interrupted at the end point of the broken line 75, and as shown in FIG. 20, the wrapping container 71 is not completely separated until the wrapping container 71 has been put on the fingers.

Moreover, the interlabial pad 2 (not illustrated) enclosed in the wrapping container is folded to be enclosed with the belt body 22 directed toward the end edge at the starting position of the broken line 75. Thus, the belt body 22 is automatically oriented in the direction visible to the wearer.

Other Embodiments

Fifth Embodiment

Next, a double wrapping container consisting of an inner wrapping container for directly housing the interlabial pad and an outer wrapping container for housing this inner wrapping container will be explained below.

Figure 25:
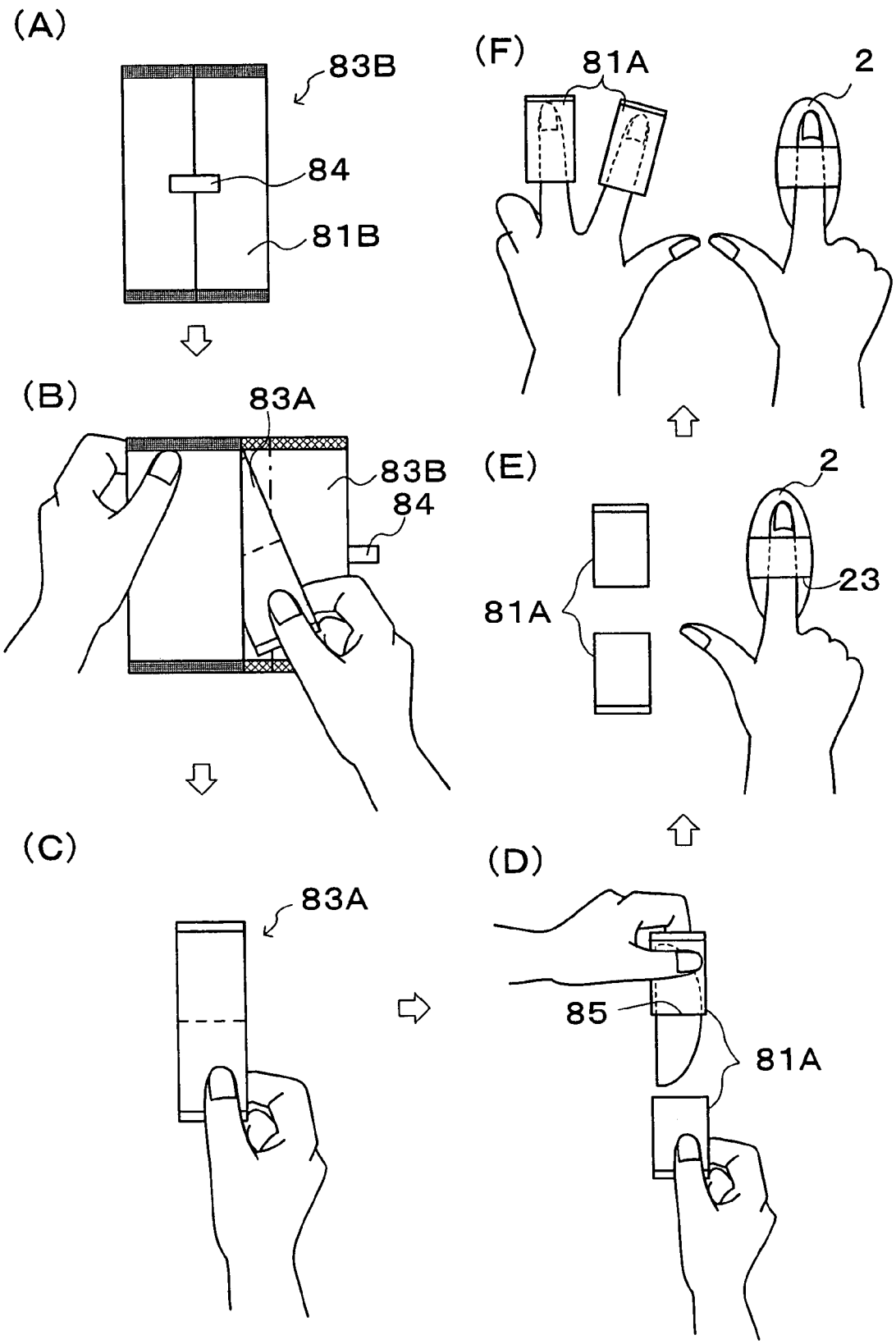
FIGS. 25(A)-(F) illustrate a method for opening the interlabial pad individual wrapping container in accordance with the fifth embodiment and a method for separating the inner wrapping body wrapping container.

FIG. 21 illustrates a state in which the inner wrapping body 83A is enwrapped in a series of wrapping sheets 80 to form the outer wrapping body 83B; FIG. 22 illustrates an outer wrapping container 81B with a pocket portion 88; FIG. 23 is a drawing illustrating a double-structured wrapping body in which the inner wrapping container 83A is enclosed in a pocket portion 88 arranged in the outer wrapping container 81B to form an outer wrapping body 83B; FIG. 24 illustrates a double-structured wrapping body in which the inner wrapping body 83A is arranged on the pocket portion 88 arranged in the outer wrapping container 81B to form the outer wrapping body 83B; and FIG. 25 shows a process drawing for illustrating a method for taking out the interlabial pad 2 enclosed in the double-structured wrapping container and putting it on a finger.

As shown in (A) of FIG. 21, the inner wrapping body 83A directly enclosing the interlabial pad (not illustrated) is provided with a broken line 85 in the lateral direction, and the inner wrapping container 81A can be opened along this broken line 85. This inner wrapping body 83A (not illustrated) is arranged on the wrapping sheet 80, and as shown in (B) of the same figure, this inner wrapping body 83A is enwrapped in the wrapping sheet 80 in the lateral direction, and the overlapping parts of the wrapping sheet 80 and both of top and bottom end edges are joined to be peelable again. In this case, both of the top and bottom end edges are joined so as not to be on the end edges of the inner wrapping body 83A (not illustrated).

Then, the overlapping parts of the wrapping sheet 80 is sealed with a stop tape 84 provided on the wrapping sheet 80. This top tape 84 maintains the sealing state of the outer wrapping body 83B and also it is picked up at the time of unsealing it. Further, to throw away a used interlabial pad 2, the stop tape can be used as a means for re-sealing the used interlabial pad 2 when re-packaging it in the wrapping sheet 80.

The outer wrapping container 81B can be provided with a pocket portion 88. More specifically, as shown in FIG. 22, the pocket portion 88 is formed by folding the wrapping sheet 80 inside, and joining only one side part 80d or both side parts of 80c and 80d in the end part opposite to the end part where the stop tape 84 of the wrapping sheet 80 is fixed. By forming the outer wrapping container 83B by thus folding the wrapping sheet 80, it becomes possible to enclose a used interlabial pad 2 (not illustrated) and an inner wrapping container 81A (not illustrated) used as a finger cot in the pocket portion 88 arranged in the outer wrapping container 81B beforehand, and this improves convenience for waste disposal more.

When enclosing the inner wrapping body 83A in the outer wrapping container 81B having such a pocket portion 88, as shown in FIG. 23(A), the inner wrapping body 83A is enclosed in the pocket portion 88 to form the outer wrapping body 83B by sealing the outer wrapping container 81B with the stop tape 84, but the inner wrapping body 83A may be arranged on the pocket portion 88 as shown in FIG. 24(A). When the inner wrapping body 83A is enclosed in the pocket portion 88, as shown in FIG. 23(B), the pocket portion 88 is positioned so as to envelope the interlabial pad inside the outer wrapping body 83B, and when the inner wrapping body 83A is arranged on the pocket portion 88, as shown in FIG. 24(B), the pocket portion 88 is positioned under the lower side of the inner wrapping body 83A inside of the outer wrapping body 83B.

When using the interlabial pad 2 enclosed in such a double-structured wrapping container, as shown in FIG. 25(A), firstly, holding the outer wrapping body 83B with the stop tape 84 plane up, a wearer picks up such a stop tape 84 to unseal the outer wrapping container 81B. Next, the wearer takes out the inner wrapping body 83A, and holds the inner wrapping body 83A as shown in (B) of the same figure. Then, as shown in (D) of the same figure, the wearer separates the inner wrapping container 81A into two small sections along the broken line 85, takes out the interlabial pad 2 as shown in (E) of the same figure, and inserts her finger through the finger insertion opening 23 to hold the pad on the fingertip. Further, as shown in (F) of the same figure, the wearer holds the two sections of the inner wrapping container 81A on the two fingertips of the left hand.

Sixth Embodiment

Figure 26:
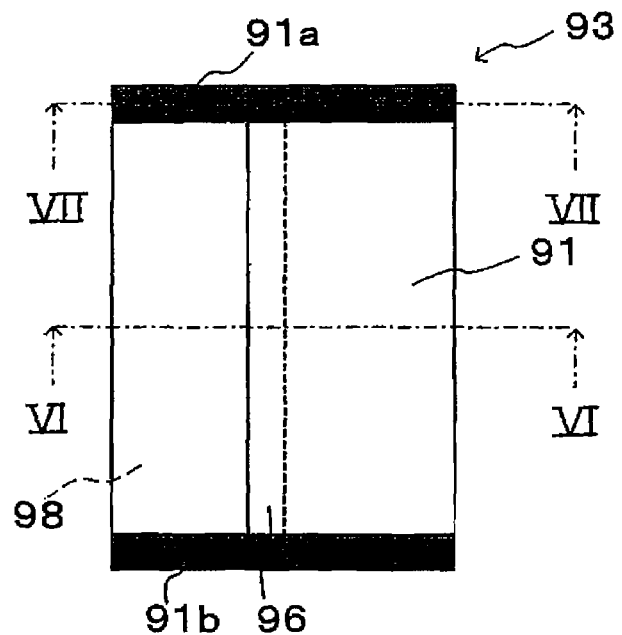
FIG. 26 is a drawing showing the wrapping body enclosing the interlabial pad in the interlabial pad individual wrapping container in accordance with the sixth embodiment.
Figure 27:
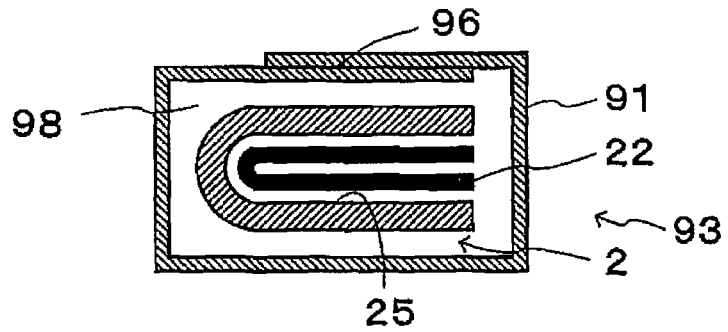
FIG. 27 is a section view taken along arrow line VI-VI of FIG. 26.
Figure 28:
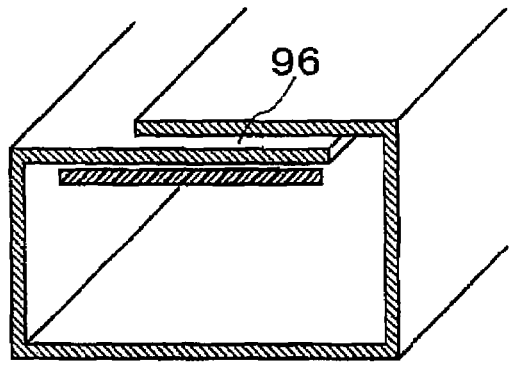
FIG. 28 is a sectional perspective view taken along the arrow line VII-VII of FIG. 26.
Figure 29:
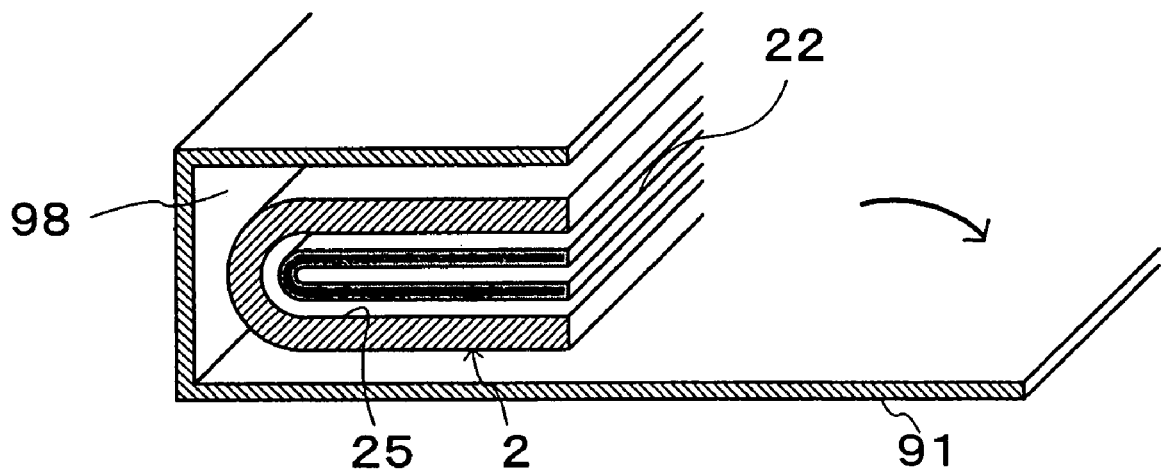
FIG. 29 is a sectional perspective view showing the unsealed state of the interlabial pad individual wrapping container in accordance with the sixth embodiment.
Figure 30:
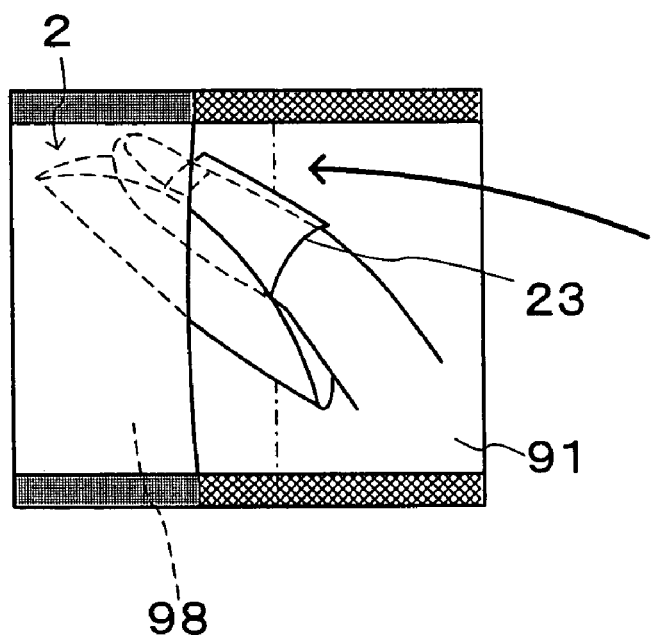
FIG. 30 is a drawing illustrating a state of holding the interlabial pad on the fingertip by inserting a finger in the finger insertion opening of the interlabial pad enclosed in the pocket portion of the unsealed interlabial pad individual wrapping container in accordance with the sixth embodiment.

Next, a wrapping container having a packet part will be explained below. FIG. 26 illustrates the external of a wrapping body 93 enclosing the interlabial pad 2 in a wrapping container 91 having a pocket portion 98 for enclosing the interlabial pad 2; FIG. 27 is a sectional view taken along the arrowed line VI-VI of FIG. 26; FIG. 28 is a sectional view take along the arrowed line VII-VII of FIG. 26, FIG. 29 is a sectional view illustrating the unsealed state of the wrapping container 91; FIG. 30 illustrates the state in which a wearer inserts her finger in the finger insertion opening 23 of the interlabial pad 2 in the unsealed wrapping container 91 and holds the interlabial pad on the finger; and FIG. 31 is a process drawing illustrating the process of unfixing a used interlabial pad 2 by using the wrapping container 91 with the pocket portion 98.

[Constitution of Wrapping Container]

In the wrapping body 93 shown in FIG. 26, as shown in FIG. 27, the interlabial pad 2 folded along the longitudinal center line is enclosed in the pocket portion 98 formed by partly folding one end part of the wrapping sheet in the wrapping container 91 formed from a series of wrapping sheets. And further, the other end part is folded so as to overlap with the pocket portion 98, and the overlapping pat is joined to be peelable by a known technique such as connection by heat-embossing pressure, male-female embossing, etc., to form a pre-opening part 96 for unsealing the wrapping container 91.

Moreover, the top and bottom end edges 91a, 91b are also joined to be peelable so as not to overlap with the enclosed interlabial pad 2. In order to strengthen this joining condition, not only known techniques such as heat-sealing and male-female embossing but also an adhesive can be used together. Specifically, referring to FIG. 28, an adhesive (not shown) is applied beforehand to the wrapping sheet in the neighborhood of the overlapping pre-opening part 96. The adhesive can be selected from hot-melt type adhesives without restriction, and is applied in a known application pattern in a form of plane, stripes, spiral, Ω, etc. In such a manner, it is possible to surely eliminate a danger of exfoliation between the wrapping container 91 and the interlabial pad 2 when enclosing a used interlabial pad 2 which will be described later. Moreover, the interlabial pad 2 is stuck to the wrapping container 91 with the above adhesive applied in the wrapping container 91 before it is opened.

Here, as obvious from FIG. 29, in the pocket portion 98, the interlabial pad 2 is folded so that its rear face sheet faces each other, therefore, the belt body 22 is positioned on the innermost plane. Moreover, since the folded part of the interlabial pad 2 is formed almost along the longitudinal center line, the finger is inserted in the interlabial pad 2 in the same direction as its crease, the wearer can easily hold the interlabial pad 2 on the fingertip at the time of wearing it. In this point, when the interlabial pad 2 is folded centering the lateral axis, the direction of the finger insertion and the crease differ in direction, therefore, the wearer has to open once the folded interlabial pad 2 before inserting the finger in the finger insertion opening 23, and this prevents the wearer from speedily and smoothly fixing the interlabial pad 2 on the finger.

[Unsealed State]

As shown in FIG. 29, when the wrapping container 91 is unsealed, the wearer can observe the belt body 22 at the same time as she opens it, and as shown in FIG. 30, she can insert her finger in the finger insertion opening in that state and can hold the interlabial pad 2 on the finger.

Regarding this point, when the pre-opening part 96 and the folded part of the interlabial pad 2 are positioned at the same place, the folded side of the interlabial pad 2 is observed by the wearer when she opens it, and the wearer has to turn the direction of the interlabial pad 2 to find the finger insertion opening 23 of the interlabial pad 2, this makes the action complex and a smooth wearing action is prevented.

In contrast to the above, in this embodiment, it is possible to sanitarily take out the interlabial pad 2 without contact between the body side of the interlabial pad 2 and the finger, and also the wearing direction is induced, and, further, pushing pressure over the lengthwise direction for pushing the interlabial pad between the labia can be obtained at the stage when the interlabial pad 2 is secured. Namely, if the actions of inserting the finger in the finger insertion opening 23 and holding the interlabial pad on the fingertip are once performed, it is possible for the wearer to perform in that state a series of actions such as taking the interlabial pad 2 from the wrapping container 91, wearing it in labia, and pushing it to labia.

[Disposal of Used Interlabial Pad]

To dispose of a used interlabial pad 2, the interlabial pad 2 is taken from between the labia firstly by, as shown in FIG. 31(A), inserting the finger in the finger insertion opening of the interlabial pad 2 and holding it on the fingertip. Next, as shown in (B) of the same figure, a wearer inserts a finger holding the interlabial pad in the pocket portion 98 of the wrapping container 91, and pinches the interlabial pad 2 from outside of the wrapping container 91 by the opposite hand. Then, as shown in (C) of the same figure, the wearer draws her right hand from the finger insertion opening 23, and as shown in (D) of the same figure, she folds the wrapping sheet 90 and holds it on the pocket portion 98 with a stop tape 94 for sealing it. This stop tape 94 prevents the wrapping body 93 from being unsealed when it is thrown away. Sealing means other than using the stop tape are; application of an adhesive to the overlapping part, sticking a magic tape (a registered trade mark), a chuck arrangement for engaging the male and female parts with each other, etc.

Moreover, when a wearer takes out the interlabial pad from the labia, she can remove it also by pinching the belt body 22. Since the belt body 22 is positioned on opposite side face to body side face, the belt body 22 never comes into contact with absorbed menstrual blood, and the menstrual blood does not adhere to the finger of the wearer also at the time of removing the interlabial pad 2 from the labia.

Seventh Embodiment

Next, a wrapping container having two unwrapped openings will be explained below. FIG. 32 illustrates a wrapping container 101 enclosing an interlabial pad 210 having two finger insertion openings 213A and 213B.

The interlabial pad 210 is provided with two finger insertion openings 213A and 213B to be chosen according to depths of labia of wearers (cf FIG. 47). The wrapping container 101 is provided with two pre-opening parts 106A and 106B corresponding to the two finger insertion openings of this interlabial pad 210. The characters of "shallow" and "deep" are added to the respective pre-opening parts as the marks for indicating which finger insertion opening is positioned therefore. Therefore, as shown in FIG. 32(A), a wearer having a shallow depth of labia can select the pre-opening part 106A with the character "shallow" to open, and as shown in FIG. 32(B), a wearer having a deep depth of labia can select the pre-opening part 106B with the character "deep" to open. Thus, it is possible for a wearer to judge which pre-opening part to open even from the outward looking of the wrapping container 101.

Eighth Embodiment

Figure 33:
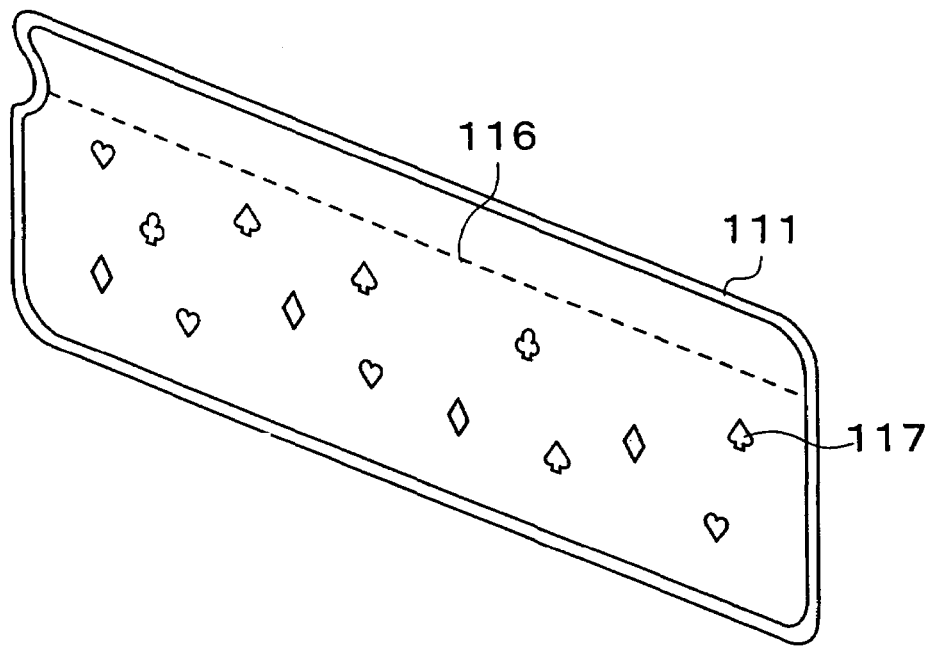
FIG. 33 shows a drawing illustrating the interlabial pad individual wrapping container in accordance with the eighth embodiment.

Next, a wrapping container the opening direction of which is indicated by a pattern will be explained below. FIG. 33 illustrates the wrapping container 111 provided with a pattern 117.

As shown in FIG. 33, the wrapping container 111 can be provided with a pattern 117 having the top and bottom. In such a manner, not only fashionability is added to the wrapping container 111, but a wearer can understand the upper part at a glance where the pre-opening part 116 as an opening position is positioned.

[Wrapping Container for Individually Packaging Sanitary Napkin with Pocket Portion for Enclosing Interlabial Pad]

Figure 34:
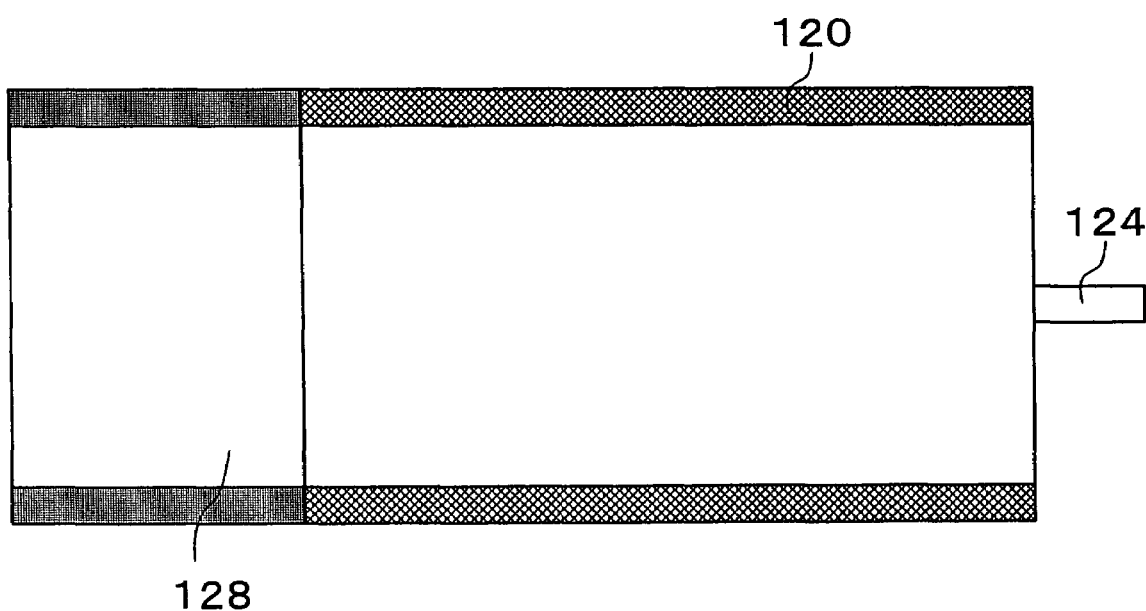
FIG. 34 is a drawing illustrating the wrapping sheet with a pocket portion keeping a sanitary napkin therein.
Figure 36:
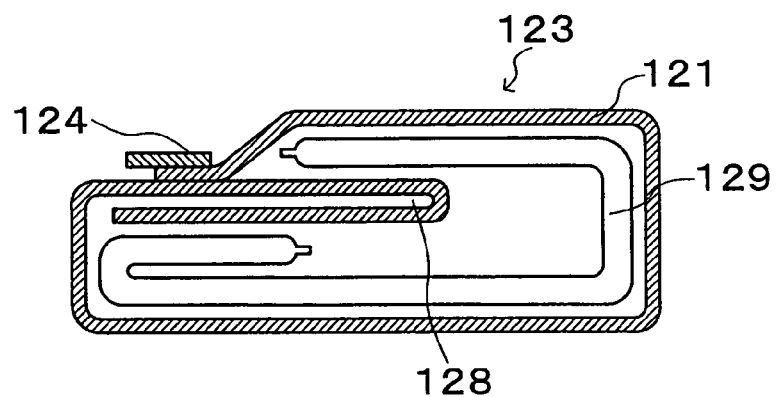
FIG. 36 is a perspective sectional view taken along the arrow line VIII-VIII of FIG. 35(E).
Figure 37:
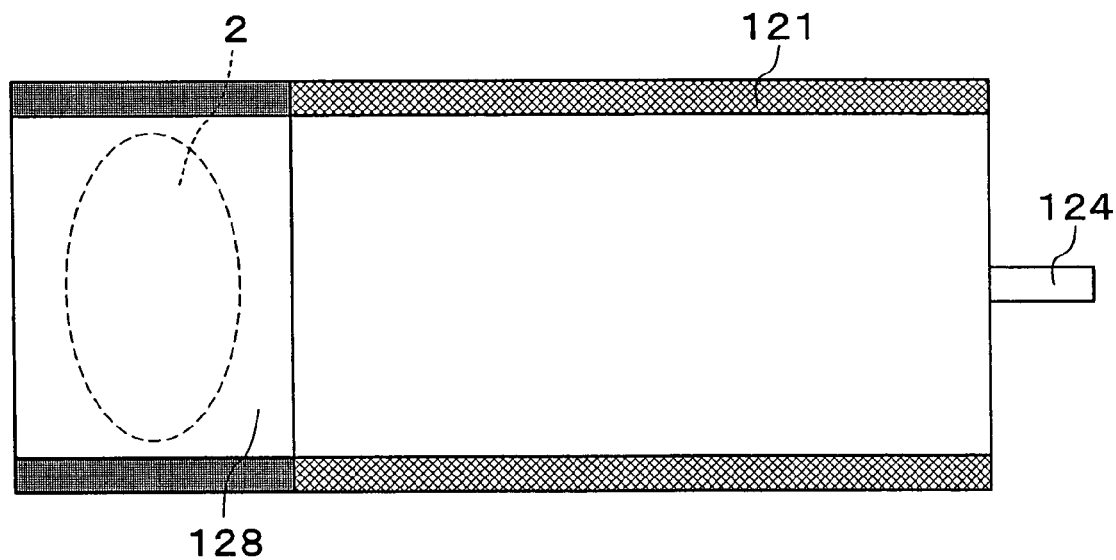
FIG. 37 is a drawing showing the wrapping sheet with the pocket portion after having unsealed the wrapping container and taken out the sanitary napkin therefrom.

Next, a wrapping container for individually packaging a sanitary napkin having a pocket portion for enclosing an interlabial pad will be explained below. FIG. 34 is a drawing for illustrating a wrapping sheet 120 with a pocket portion 128 for enclosing a sanitary napkin therein; FIG. 35 is a process drawing illustrating a method for enclosing the sanitary napkin 129 in a wrapping container 121 formed from a wrapping-sheet 120 to form a wrapping body 123; FIG. 36 is a section view taken along the arrowed line VIII-VIII of FIG. 35(D); and FIG. 37 illustrates the wrapping sheet 120 after the wrapping container 121 has been opened and the sanitary napkin 129 has been taken out.

In the wrapping sheet 120 for the sanitary napkin shown in FIG. 34, the pocket portion 128 is formed by folding one end part thereof, and joining both lengthwise overlapping edge parts of this folded part of the wrapping sheet 120 by heat-sealing etc.

The pocket portion 128 can also be formed by using another material, and joining this on a part of the wrapping sheet 120. In this method, heat-sealing, ultrasonic sealing, hot-melt type adhesive, etc. can be used for the joining, and as for the material, a film, paper, non-woven fabric, etc. can be used singly or compositely.

When the sanitary napkin 129 is wrapped in the wrapping sheet 120, as shown in FIG. 35(A), the wrapping sheet 120 is firstly placed with the pocket portion 128 up, and secondly, as shown in (B) of the same figure, the sanitary napkin 129 is placed thereon with its body side face faced to the sheet. Next, as shown in (C) of the same figure, the end part 12a of the wrapping sheet 120 with the pocket portion 128 is folded inside together with the end part 129a of the sanitary napkin 129. Following this, as shown in (D) of the same figure, the other end part 120b of the wrapping sheet 120 and the other end part 129b of the sanitary napkin 129 are also folded inside. And in order to maintain this folded state, a part 126 of the overlapping part, where the edge parts 120a and 120b of the wrapping sheet 120 overlap with each other, is temporarily tacked so as to be re-opened and sealed with a stop tape 124. Moreover, the edge parts 120c and 120d of the wrapping sheet 120 as the top and bottom of the wrapping container 121 are also temporarily tacked by heat-sealing, ultrasonic sealing, etc. so as to be re-opened. Thus, as shown in (E) of the same figure, the wrapping body 123 is formed.

As shown in FIG. 36, the part in which only the wrapping sheet 120 is wrapped up is formed inside of the wrapping body 123. As shown in FIG. 34, this part is the pocket portion 128 which was already formed in the wrapping sheet 120 before enclosing the sanitary napkin 129, and as shown in FIG. 37, it is possible to put the used interlabial pad 2 in this pocket 128 after the wrapping container 121 is opened.

The sanitary napkin 129 can be taken out of the wrapping body 123 by picking up the stop tape 124 first, pulling it to open one edge part 120b of the wrapping sheet 120 outside, opening the temporarily tacked overlapping part 126, and then opening also the other edge part 120a of the wrapping sheet 120 outside. Thus, the wrapping container 121 is completely opened.

Here, the direction in which the end part 120b of the wrapping container 120 is pulled is opposite to the direction in which the pocket portion 128 is formed. Therefore, the pulling action for opening the overlapping part 126 has no influence on the pocket portion 128, and the pocket portion 128 is reduced in receiving damage.

Moreover, in order to strengthen the maintenance state of the pocket portion 128, it is also possible to apply an adhesive only to the inside of the sealing part for forming the pocket portion 128 and reinforce the opening part of the pocket portion 128.

The opposite side face to body side face of the sanitary napkin 129 is coated with an adhesive for being attached to an underwear. Therefore, the wrapping sheet 120 is provided with a peeling part on the part corresponding to the region coated with this adhesive, so that such an adhesive can be protected to be peelable. Such a peeling part may be formed by separately applying a removable material thereto such as removable paper and separate film, and the wrapping sheet itself may be provided with peeling treatment. When a removable material is attached, this material is preferred to be adhered to the wrapping sheet with an adhesive in advance. In such a manner, it becomes possible to prevent extra waste from being thrown away during the fixing action of the sanitary napkin 129 as in the case that the removable material separate from the wrapping sheet is stuck on an adhesive, and this improves the convenience of the action.

The sanitary napkin which can be used in this embodiment is not to be restricted to a specific type but various types such as a type with wing and a type without wing and the likes can be applied.

[Wrapping Body]

Next, a wrapping body, in which the interlabial pad is enclosed so that the finger insertion opening of the interlabial pad is positioned in the neighborhood of the pre-opening part of the wrapping container, will be explained below.

Figure 38:
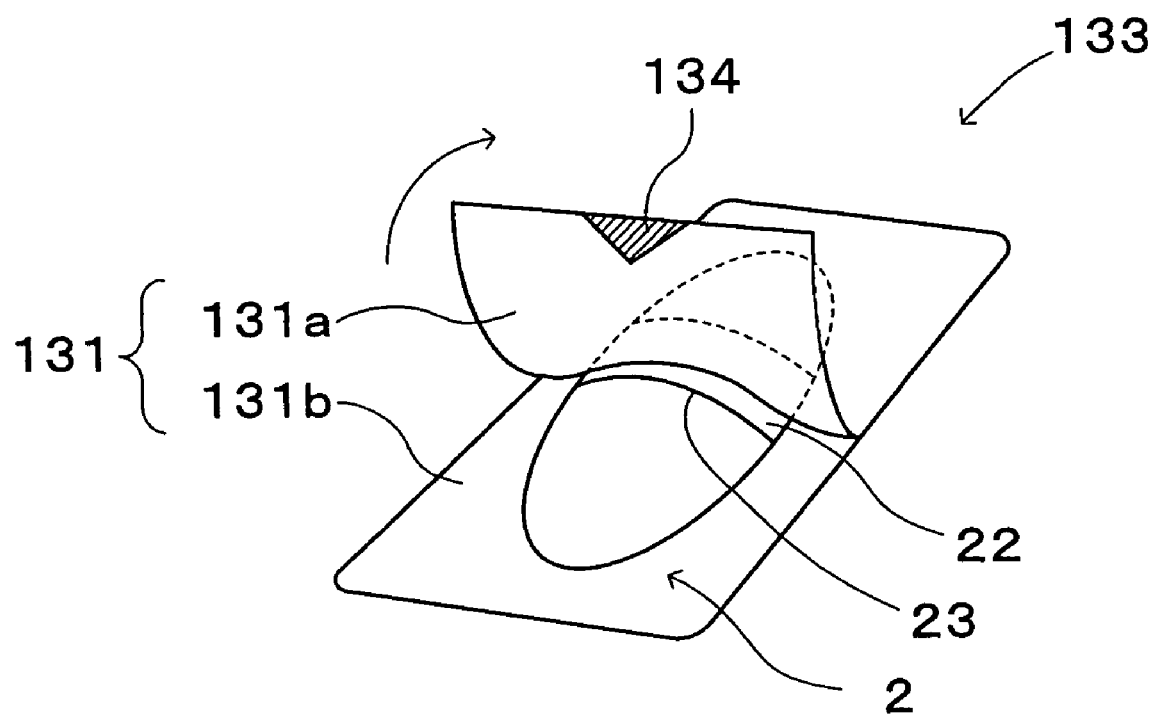
FIG. 38 illustrates the wrapping body containing the interlabial pad in accordance with this embodiment therein as it is without being folded.

FIG. 38 illustrates a wrapping body 133 in which the interlabial pad 2 in accordance with this embodiment is enclosed in the wrapping container 131 as it is, without being folded; FIG. 39 illustrates a wrapping body 143 enclosing the interlabial pad 2 folded with the belt body 22 shaped like a chevron; FIG. 40 illustrates a wrapping body 153 in which the interlabial pad 2 is folded and enclosed in a wrapping container 151 to be opened in a double-door form; FIG. 41 illustrates a wrapping body enclosing the interlabial pad 2 folded centering the lateral line, and a wrapping body enclosing the interlabial pad 2 with only a part of both sides folded.

As shown in FIG. 38, when the interlabial pad 2 is enclosed in such a wrapping container 131 as is opened by stripping the upper side 131a upward from the lower side 131b, the interlabial pad 2 is placed and enclosed therein with the belt body faced upward. Thus, a wearer is able to hold the interlabial pad 2 on the fingertip by inserting the finger in the finger insertion opening 23 immediately after the wrapping container 131 is opened. Moreover, it is preferable that a marking 134 or the like is provided on the upper side 131a in order to clearly show the direction of stripping.

In FIG. 38 mentioned above, the interlabial pad 2 is enclosed in the wrapping container 131 as it is, without being folded, however, it is also preferred to be folded for being enclosed so that the finger insertion opening 23 is naturally opened when the wrapping container is unsealed. When the interlabial pad 2 is folded, for example, as shown in FIG. 39(A), the interlabial pad 2 can be enclosed in the wrapping container 141 with the whole pad folded in a chevron shape. Moreover, as shown in (B) of the same figure, it is also possible to shape only the belt body 22 like a chevron, but fold the main body part of the interlabial pad 2 in a V-shape toward the opposite side to the body side on the other hand for enclosing the pad in the wrapping container 141. Moreover, as shown in FIG. 40, even a wrapping container 151 to be unsealed by pulling both sides 151A and 151B toward left and right from the top (what is called a set of folding doors method), the interlabial pad 2 can enclose the interlabial pad therein with the belt body 22 folded The folding mode of the interlabial pad 2 can be changed appropriately according to the wrapping containers, and it does not matter whether the interlabial pad 2 is folded in half in the vertical direction as shown in FIG. 41(A) or only both side edge parts of the interlabial pad 2 are folded as shown in FIG. 41(B).

[Interlabial Pad]

<Basic Configuration of Interlabial Pad>

Figure 42:
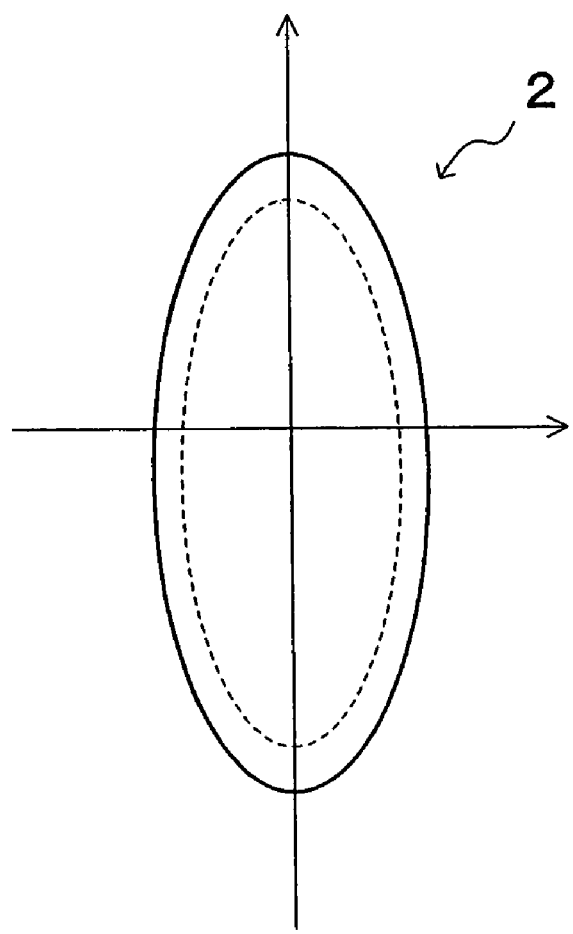
FIG. 42 is a body side schematic drawing of the interlabial pad.
Figure 43:
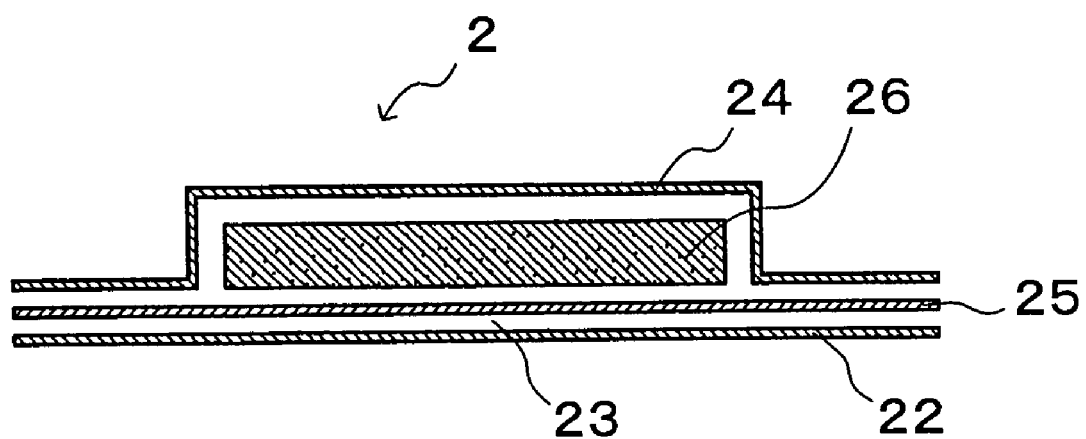
FIG. 43 is a cross sectional schematic drawing of the interlabial pad.

The basic configuration of the interlabial pad in this embodiment will be explained below. FIG. 42 is a schematic drawing of the body side of the interlabial pad 2, and FIG. 43 is a cross sectional view of the interlabial pad 2. Moreover, the interlabial pad 2 can be used for absorbing excretions (vaginal discharge) other than menstrual blood discharged from a ostium vaginae, and can also be used for absorbing urine discharged from an urethral opening, namely, it can be used against incontinence of urine.

The interlabial pad 2 in this embodiment is substantially an oblong form with a lateral dimension and a longitudinal dimension. Moreover, the outline form is elliptic, but as long as it has such a shape as can preferably be held, and it can arbitrarily be selected from a rectangle, an oblong ellipse, a sandglass type, etc.

As shown in FIG. 43, the interlabial pad is comprised of a body side surface in direct contact with the inside of labia and an opposite side face to body side face which is faced to the opposite side to the body side of a wearer and is not in direct contact with the inside of labia. And, the absorbent body 26 is placed between a water permeable surface sheet 24 positioned on the body side and a water impermeable underside sheet 25 positioned on the opposite side face to body side face, and the surface sheet 24 and the underside sheet 25 are joined to each other in the periphery of the absorbent body 26.

And, a belt body 22, a mini-sheet piece for the interlabial pad, is attached on the side part of the opposite side face to body side face of the underside sheet 25 so as to traverse the interlabial pad 2 in the widthwise direction. A finger insertion opening 23 into which the finger can be inserted is formed between this belt body 22 and the underside sheet 25.

In order for a wearer to easily discriminate the belt body 22, it can also be adjusted so as to differ in a color tone, a pattern, or chromaticity from the underside sheet of the interlabial pad by means of coloring, printing, etc.

<Other Configurations of Interlabial Pad>

Figure 44:
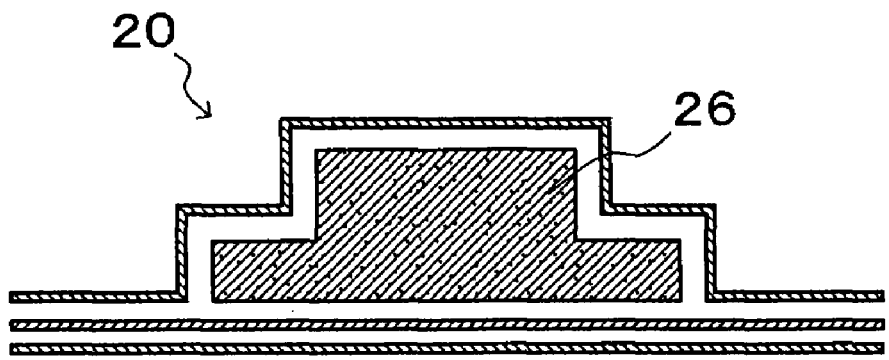
FIG. 44 shows a cross-sectional view of an interlabial pad of another structure illustrating a convex structure of the interlabial pad in which a middle area of the contained absorbent body is raised.
Figure 45:
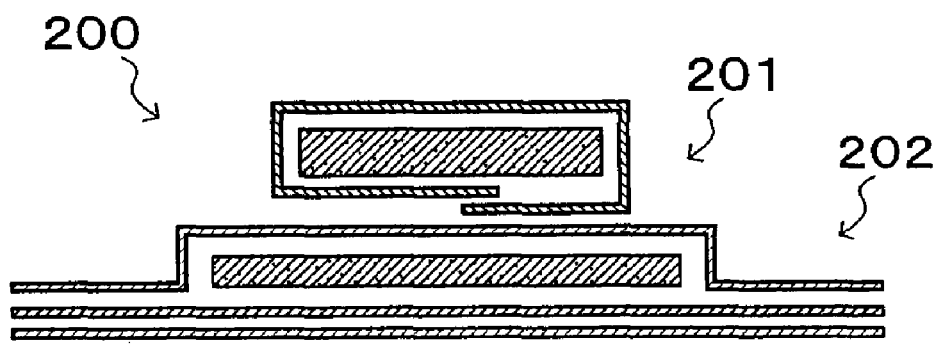
FIG. 45 is a drawing illustrating an interlabial pad formed by piling up two sheets of different widthwise lengths.
Figure 46:
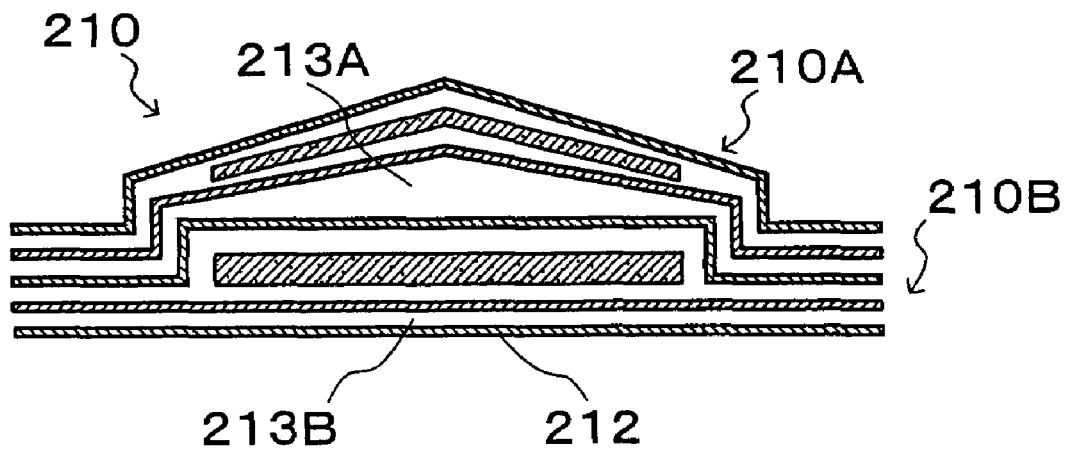
FIG. 46 is a drawing showing an interlabial pad including a main sheet body and a sub-sheet body.

Next, the other configurations of the interlabial pad 2 will be explained below. FIG. 44 illustrates an interlabial pad 20 of a mid-upheaval structure in which the mid-area of the absorbent body 26 is upheaved; FIG. 45 illustrates an interlabial pad 200 made by putting two sheets together differing in the widthwise length; FIG. 46 illustrates an interlabial pad 210 consisting of two layers of a main sheet body 210A which can be fitted deep in the labia and a sub-sheet 210B; and FIG. 47 illustrates a state in which the interlabial pad 210 is held on the finger.

In the interlabial pad 20 shown in FIG. 44, the absorbent body 26 is partly upheaved in the widthwise center to increase adherence of the interlabial pad 20 in the labia of a wearer. Therefore, it is possible to prevent menstrual blood from leaking outside.

As to the interlabial pad 200 shown in FIG. 45, the auxiliary sheet body 201 having a shorter widthwise length is laid on the body side surface of the ordinary interlabial pad 202, and both are joined together at the front and rear with an adhesive or heat-sealing, ultrasonic sealing, etc., or the overlapping part is joined to each other with an adhesive, or both joining methods are used together. This auxiliary sheet body 201 improves a body fluid absorbing ability of the interlabial pad, and thereby improves the effect of preventing menstrual blood from leaking.

Further, the interlabial pad 210 shown in FIG. 46 is comprised of a main sheet body 210A and a sub-sheet body 210B, and both are joined together at each lengthwise edge part, and both are apart inside thereof, and further, in the widthwise direction, at least one of both sleeve parts is not joined. Therefore, a wearer can insert a finger into the two holes which are the first finger insertion opening 213A between the main sheet body 210A and the-sub sheet body 210B, and the second finger insertion opening 213B between the mini-sheet body 212 for the interlabial pad and the sub-sheet body 210B. Therefore, the wearer is able to choose either of them according to her own depth of labia, and for example, a wearer with a shallow depth of labia inserts her finger from the first finger insertion opening 213A as shown in FIG. 47(A), while a wearer with a deep depth of labia inserts her finger from the second finger insertion opening 213B as shown in FIG. 47(B).

Moreover, the wrapping container for enclosing such an interlabial pad 210 is preferred to be provided with the pre-opening parts at two places as the wrapping container 101 shown in FIG. 32. Moreover, when the interlabial pad 210 is enclosed in the wrapping container 101, the finger insertion opening 213A is positioned to the pre-opening part 106A with the character "shallow", and the finger insertion opening 213B is positioned in the periphery of the pre-opening part 106B with the character "deep".

[Construction Material of Wrapping Container]

<Wrapping Sheet>

Known materials can be used as the wrapping sheet for the wrapping container. For example, 15-60 micron polyethylene, polylpropyrene-polyester, polyvinyl-alcohol; poly-lactic acid, polybutyl-succinate, or non-woven fabric, paper, and laminated materials of these can be used. Specifically, a film consisting essentially of LDPE (low density polyethylene) resin adjusted to 15-30 g/mm$^2$ specific weight per unit area is generally used.

A laminated material of which the outside surface is composed of a film of non-woven fabric or paper can be used considering wiping property, liquid blocking property, etc. Specifically, a composite material can be used, on which a film consisting essentially of the LDPE resin adjusted 5-20 g/m$^2$ specific weight per unit area is laminated on one side of the composite non-woven fabric consisting of spun bond, melt blown, spunbond of 6-10 gsm, 5-20 gsm, 6-10 gsm by weight.

Moreover, when washing suitability is considered, non-woven fabric such as polybutylene-succinate, poly-lactic acid, polyisocyanate, starch can be used, and when the material is obtained from a film and water soluble, a film consisting essentially of polyvinyl-alcohol can be used, and use of toilet paper is also possible. Specifically, a laminated material of a polyvinyl-alcohol film adjusted to 5-10 g/m$^2$ specific weight per unit area and water soluble paper adjusted to 15-30 g/m$^2$ can be mentioned.

The wrapping sheet can be used also for wrapping a used interlabial pad and disposing of it when the interlabial pad is disposed of after use. In this case, it is preferable that menstrual blood adhering to the interlabial pad or absorbed into it is prevented from oozing from the wrapping sheet, namely, it is preferable that the menstrual blood is prevented from adhering to the finger when a wearer picks up the wrapping sheet wrapping the used interlabial pad. Therefore, a material rich in liquid blocking property, for example, a film consisting of about 15-60 μm thick polyethylene, polypropylene, etc., or a laminated material obtained by laminating the raw materials for the film is recommended for the use.

Moreover, it is preferable that the wrapping sheet is able to shield the color of the menstrual blood adhering to or absorbed in the interlabial pad.

To obtain such a shield effect, for example, the wrapping sheet is photogravured with an ink consisting of a 5-40 wt % pigment, a 10-20 wt % resin, and a 40-85 wt % solvent, or a sheet material opaqued by mixing a 0.2-10 wt % pigment in the raw material resin of the wrapping sheet is recommended for the use. Otherwise, the wrapping sheet may be dyed. The pigment for the use may be white or colored, for example, the following pigments can be used singly or in combination: C.I. basic violet 3, etc. as basic dyes; C.I. vat blue 1 etc. as vat dyes; blue 1, blue 2, C.I. acid red 51, etc. as acid dyes; C.I. direct yellow 12, C.I. direct orange 26, C.I. direct violet 51, C.I. direct blue 1, C.I. direct red 23, etc. as direct dyes; C.I. reactive orange 16, C.I. reactive black 5, C.I. reactive blue 21, C.I. reactive red 21, etc. as reactive dyes; titanium oxide, titanium yellow, calcium carbonate, carbon black, ultramarine blue, etc. as inorganic pigments; and yellow 401, orange 204, blue 404, red 201, C.I. pigment yellow 14, C.I. pigment green 7, C.I. pigment violet 19, C.I. pigment blue 27, C.I. pigment red 166, etc. as organic pigments.

It is preferable that the pre-opening part and the overlapping part of the wrapping sheet forming the unsealing part are made to be repealable and to prevent foreign matters from being mixed there. Such measures can be achieved by such known techniques as not only an arrangement of a stop tape to cover the overlapping part of the wrapping sheet, but also coating of a small quantity of an adhesive along the overlapping direction, joining by embossing, perforations provided inside of the area joined by embossing, etc.

<Mini-Sheet Piece for Wrapping Container>

A material used for the mini-sheet piece used for the wrapping container is preferred to be selected considering that the material has strength to be kept undamaged when a finger is inserted therein, and the material can be selected singly from among non-woven fabric, elastic nonwoven fabric film, foamed film, elastic film, foamed sheet, tissue paper, etc. or lamination of these. Preferred breaking strength of the material is at least 0.6 N/inch lateral, and when considering the toughness, it is to be selected from a range of 0.6-2.5 N/inch. Specifically, the material used is a film consisting essentially of an LDPE resin having a density of 0.915 adjusted to 15-30 .mu.m in thickness, and a foamed film can be mentioned as an especially preferable material which facilitates drawing a finger from the mini-sheet piece for the wrapping container, and consists essentially of an LDPE resin having capillaries, a density of 0.920, a volume of 0.3-1.0 mm, a 15-60% rate of hole area, and a 0.3-1.5 mm hole diameter.

Moreover, to provide the material with biodegradabilty and water washing capability, the synthetic resin composing the structure is replaced with biodegradable or water-soluble resin such as poly-lactic acid, polybutyl-succinate, PVA resin, etc. Further, a laminated material of tissue and the biodegradable or water-soluble resin can be used.

It is also effective to provide the mini-sheet piece for the wrapping container with tensibility or elasticity in the widthwise direction of the underside sheet in order to allow a wearer to effectively use the interlabial pad according to an embodiment of the present invention irrespective of the fingertip size of the wearer.

In order to provide the mini-sheet piece for the wrapping container with elasticity, tensible spun bond non-woven fabric can be used, which has stress of 0.1-0.5 N/25 mm at the time of 5% elongation when it is elongated with a 100 mm knob distance, and a 100 mm/min constant stretching speed. Moreover, in order to provide the mini-sheet piece for the wrapping container with elasticity, elastic materials such as a fibrous sheet and film sheet using thermoplastic elastomer resin, thermoplastic elastomer resin itself, and crude rubber may singly be used or these may be combined with an inelastic material for the use.

Moreover, in order to provide the mini-sheet piece with tensibility, the film consisting essentially of the LDPE can also be corrugated.

<Stop Tape>

For the stop tape, known materials such as a film layer coated with an adhesive on one side, or tissue coated with an adhesive on one side when considering water washing capability, etc. can be used, and are not to be restricted.

[Inhibition Treatment of Number of Living Bacteria]

It is more preferable from sanitary point of view to perform a treatment for suppressing the number of living bacteria in the individual wrapping container according to an embodiment of the present invention, especially in the part in contact with the interlabial pad and the handling member thereof. As the treatments for inhibiting the number of living bacteria, sterilizing treatment or germicidal treatment during production, use of antibacterial material for the individual wrapping container, etc. can be mentioned.

[Information Supply for the Usage]

Next, the usage of the interlabial pad enclosed in the wrapping container and a means for supplying information therefore will be explained below.

<Fixing Method of Interlabial Pad enclosed in Individual Wrapping Container related to First Embodiment>

[1] Unseal the pre-unwrapped opening of the wrapping container related to the first embodiment to expose the finger insertion opening, and insert a finger of the dominant hand therein.

[2] Insert two fingers of the other hand in the finger insertion openings of the wrapping container.

[3] Open the inserted fingers to the left and right and separate a part or the whole of the wrapping container along the broken line.

[4] Laterally widen the labia by the fingers holding the separated sections of the wrapping container.

[5] Fix the interlabial pad held on the fingers of the dominant hand between the labia while seeking a fixing point.

[6] Throw away the sections of the wrapping container.

<Fixing Method of Interlabial Pad enclosed in Individual Wrapping Container related to Second Embodiment>

[1] Unseal the pre-unwrapped opening by picking the tab on the wrapping container consisting of a two-fold wrapping sheet and open the wrapping container to the left and right, to expose the finger insertion opening of the interlabial pad, and insert a finger of the dominant hand therein.

[2] Insert two fingers of the other hand in the respective finger insertion parts arranged on the side part of the wrapping container.

[3] Open the two inserted fingers to the left and right and separate a part or the whole of the wrapping container along the broken line.

[4] Laterally widen the labia by the fingers holding the separated sections of the wrapping container.

[5] Fix the interlabial pad held on the finger of the dominant hand between the labia while seeking a fixing point.

[6] Throw away the sections of the wrapping container.

<Fixing Method of Interiabial Pad enclosed in Individual Wrapping Container related to Third Embodiment>

[1] Tear a part of the pod-like wrapping container along the broken line to expose the finger insertion opening of the interlabial pad, then insert a finger of the dominant hand.

[2] Insert two fingers of the other hand in the finger insertion part on the side part of the wrapping container.

[3] Open the two fingers inserted in [2] to the left and right and separate a part or the whole of the wrapping container along the broken line.

[4] Laterally widen the labia by the fingers holding the sections separated in [3] of the wrapping container.

[5] Fix the interlabial pad held on the finger of the dominant hand between the labia while seeking a fixing point.

[6] Throw away the sections of the wrapping container.

<Fixing Method of Interlabial Pad enclosed in Individual Wrapping Container related to Fourth Embodiment>

[1] Separate the wrapping container along the broken line in the center of the wrapping container into two sections.

[2] Take out the interlabial pad and insert a finger of the dominant hand from the finger insertion opening of the interlabial pad.

[3] Put the wrapping container separated in two in [1] on two fingers of the other hand.

[4] Laterally widen the labia by the fingers holding the sections of the wrapping container.

[5] Fix the interlabial pad held on the finger of the dominant hand between the labia while seeking a fixing point.

[6] Throw away the sections of the wrapping container.

<Fixing Method of Interlabial Pad enclosed in Individual Wrapping Container related to Fifth Embodiment>

[1] Unseal the wrapping container consisting of the three-fold wrapping sheet positioned outside.

[2] Separate the inner wrapping body along the broken line in the center part.

[3] Take out the interlabial pad and insert a finger of the dominant hand from the finger insertion opening of the interlabial pad.

[4] Put the inner wrapping container separated in [2] on two fingers of the other hand.

[5] Laterally widen the labia by the fingers holding the sections of the inner wrapping container.

[6] Fix the interlabial pad held on the finger of the dominant hand between the labia while seeking a fixing point.

[7] Throw away the sections of the inner wrapping container.

<Fixing Method of Interlabial Pad enclosed in Individual Wrapping Container related to Sixth Embodiment>

[1] Expose the pocket portion by pulling the stop tape and open the wrapping sheet outside.

[2] Insert a finger in the finger insertion opening of the interlabial pad enclosed in the pocket portion (or the upper part of the pocket portion).

[3] Take out the interlabial pad from the wrapping container by drawing the finger out of the pocket portion.

[4] Fix the interlabial pad held on the finger of the dominant hand between the labia while seeking a fixing point.

<Fixing Method of Interlabial Pad enclosed in Individual Wrapping Container related to Seventh Embodiment>

[1] Confirm which is suitable for own depth of labia of the two pre-opening parts from the marks added in the neighborhood of the pre-opening parts of the wrapping container.

[2] Expose the finger insertion opening of the interlabial pad suitable for the depth of own labia by unsealing the pre-opening part with the character suited for the depth of own labia.

[3] Insert the finger of the dominant hand in the finger insertion opening exposed in [2].

[4] Fix the interlabial pad held on the finger of the dominant hand between the labia while seeking a fixing point.

<Fixing Method of Interlabial Pad enclosed in Individual Wrapping Container related to Eighth Embodiment>

[1] Confirm the top and bottom of the wrapping container by the pattern and hold the wrapping container in the correct direction.

[2] Confirm the pre-opening part and unseal it.

[3] Confirm the mini-sheet piece for the interlabial pad attached on the interlabial pad in the unsealed inner wrapping container, and then insert a finger in the finger insertion opening between the opposite side face to body side face of the interlabial pad and the mini-sheet piece.

[4] Take out the interlabial pad held on the inserted finger from the wrapping container by lifting it up.

The above usage is to induce the correct using methods for fixing the interlabial pad enclosed in the wrapping container between labia, and it is not to be restricted whether the interlabial pad is singly used or it is used together with a sheet-like absorbent article such as a sanitary napkin and a panty liner, and also with a tampon, a pants-formed sanitary napkin, etc. Moreover, when the interlabial pad is used together with another sanitary article such as a sanitary napkin and tampon, such actions as fixing the sanitary napkin to the underwear, inserting the tampon in the ostium of vagina, etc. are performed before entering the above using methods.

<Method for Removing (Replacing) the Interlabial Pad>

[1] Lower the underwear.

[2] Remove the used interlabial pad from between the labia. Or throw it away with urination into toilet bowl.

[3] Wipe the section with some wiping sheets like tissue etc.

[4] Fix a new interlabial pad.

[5] Raise the underwear.

The interlabial pad individual wrapping container is used as the member for the actions in the above [2] or [4], or in both.

Moreover, when the interlabial pad is used together with another sanitary article, the disposal process of such a sanitary article is added to the above procedure for the use.

<Information Supply for the Usage>

In order to prevent a wrong fixing method with regard to the interlabial pad according to an embodiment of the present invention, it is preferable to provide a wearer with the information on the usage as stated as above.

Here, the following cases can be mentioned as wrong fixing methods of the interlabial pad, for example: the interlabial pad is tried to be fixed laterally to the vulva slit; the interlabial pad is tried to be vertically inserted into the ostium of vagina like a tampon; the interlabial pad is fixed with the inside turned out when; and the interlabial pad is not fitted inside of the labia but is placed as if it were put on the surface of the sanitary napkin used together. In such cases, there is a fear of impairing the wear feeling, inducing excessive leak of menstrual blood, or coming off of the interlabial pad from inside of the thigh of the wearer.

With regard to the interlabial pad and the wrapping container according to an embodiment of the present invention, in order to prevent such wrong fixing, it is preferable that a wearer is correctly notified of the correct use procedures of the interlabial pad for its sufficient effect, and moreover, the wearer is clearly notified of the fixing method for being enabled to smoothly perform the wearing action.

As methods for supplying the information to wearers, the following methods can be mentioned, namely: the explanation of the usage is arranged in the individual wrapping container together with the interlabial pad; the usage is printed on the surface and inner wall of the individual wrapping container;

The description therefore is enclosed in the outer package; the usage is presented on a cooperative magazine together with the explanation of the article; the usage is presented on a home page through the Internet; the usage is presented on a display rack of a shop together with the article; the description therefore is enclosed in a sample article package; posting the description into toilets for women; oral explanation at a customers' clinic; etc. Preferable methods among such ones are those which can be confirmed by wearers every time they use it, namely: an individual wrapping container is provided with the description of the usage therein together with the interlabial pad, and the usage is printed on the outer and inner surfaces of the individual wrapping container, and more preferable method is to enclose the description attached to the interlabial pads in the outer package of them.

Figure 48:
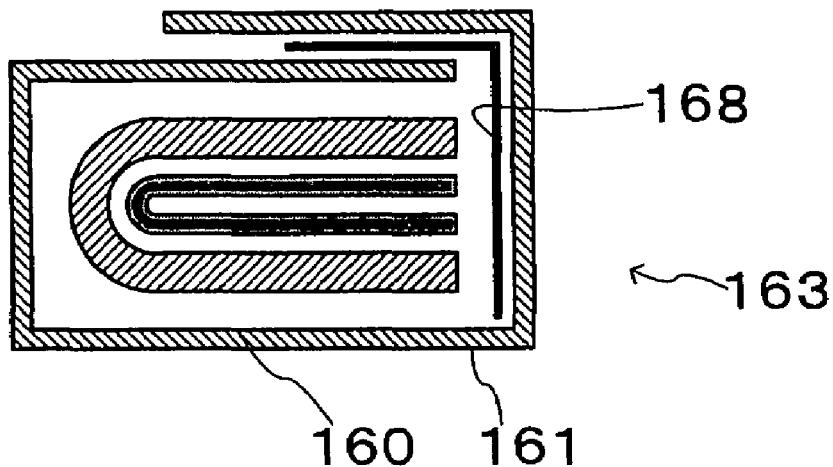
FIG. 48 is a drawing illustrating a state in which an instruction is enclosed in the interlabial pad individual wrapping container.
Figure 49:
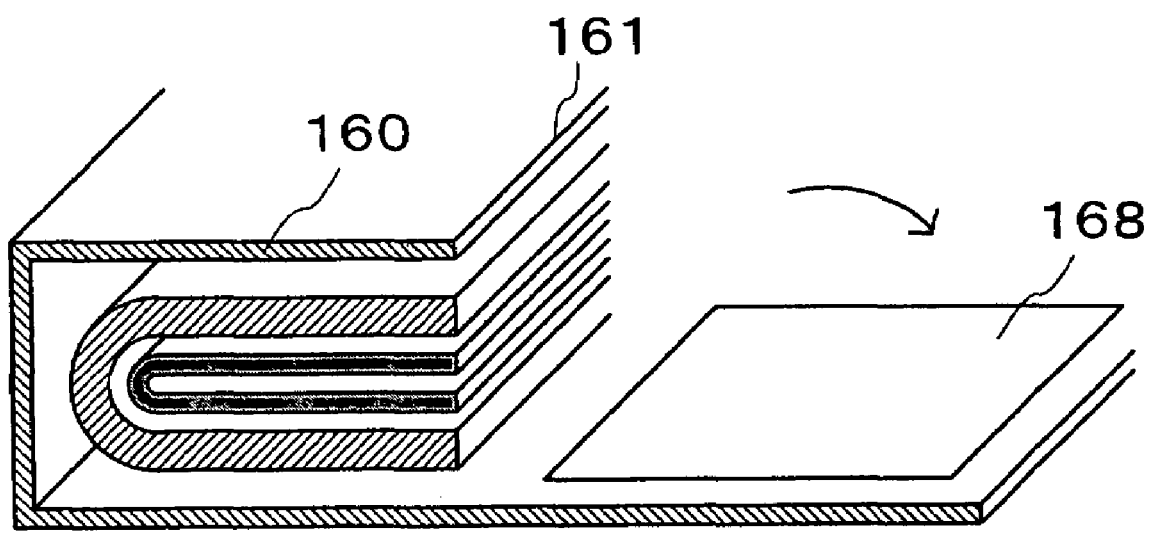
FIG. 49 is a perspective sectional view showing a state in which the interlabial pad individual wrapping container provided with the instruction is opened.

A method for providing the individual wrapping container with the description of the usage is, for example, as shown in FIG. 48, through placing the description 168 inside of the wrapping sheet 160, and folding the description 168 together with the wrapping sheet 160 at the time of enclosing the interlabial pad therein, to form them into the wrapping body 163. In such a manner, as shown in FIG. 49, when the wrapping container 161 is unsealed, the description 168 is exposed immediately, therefore, the description 168 surely attracts wearers' notice when they use the interlabial pads.

Figure 50:
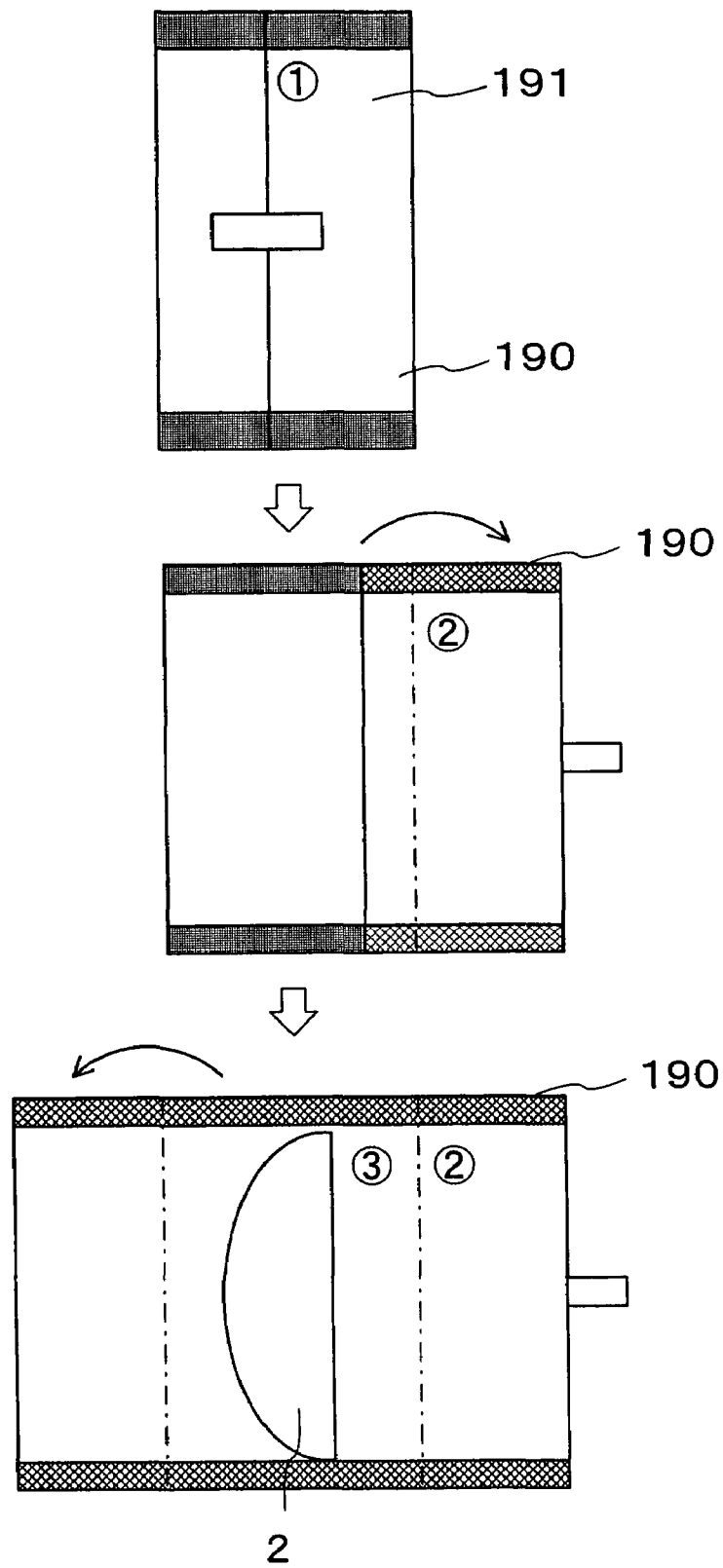
FIG. 50 is a process drawing showing a procedure for opening the interlabial pad individual wrapping container with the printed instructions for use.
Figure 51:
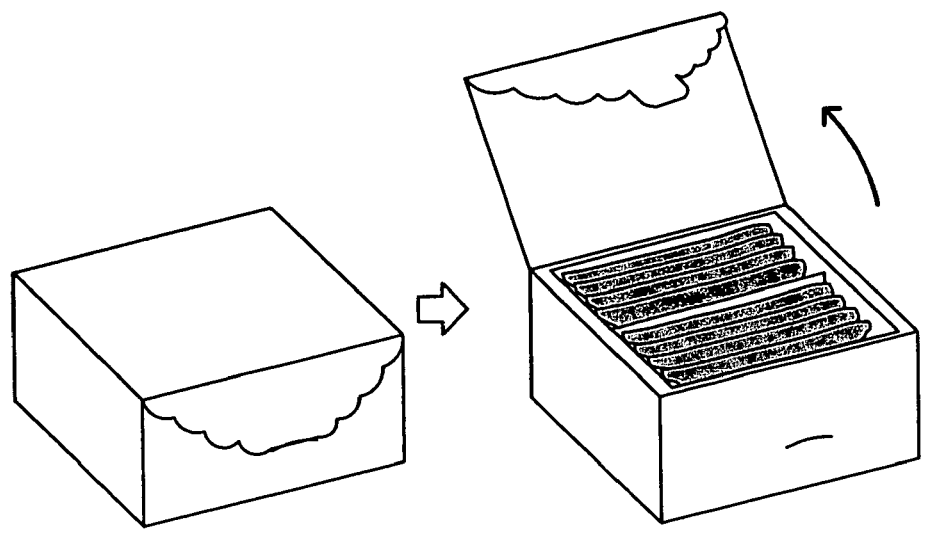
FIG. 51 illustrates the states of an outer package for packaging the interlabial pad individual wrapping containers before and after it is opened.
Figure 52:
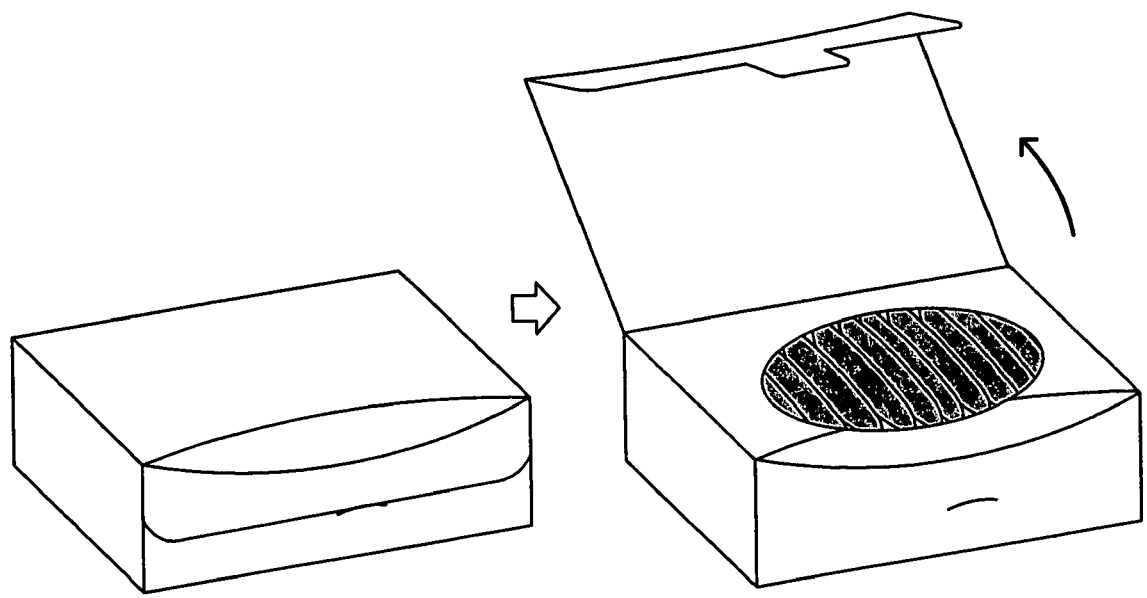
FIG. 52 illustrates the states of an outer package for packaging the interlabial pad individual wrapping containers before and after it is opened.
Figure 53:
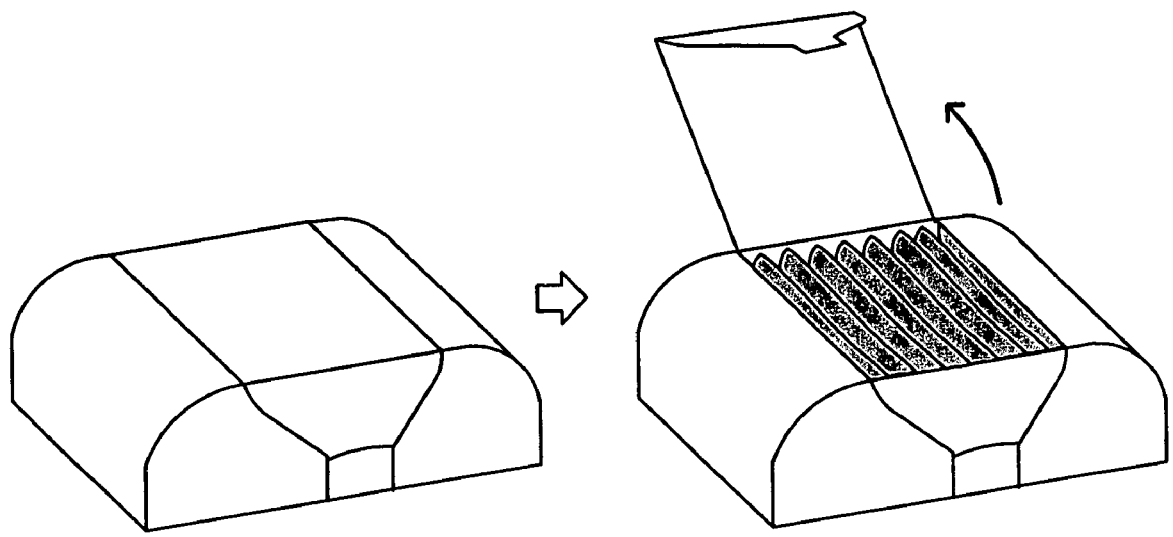
FIG. 53 illustrates the states of an outer package for packaging the interlabial pad individual wrapping containers before and after it is opened.
Figure 54:
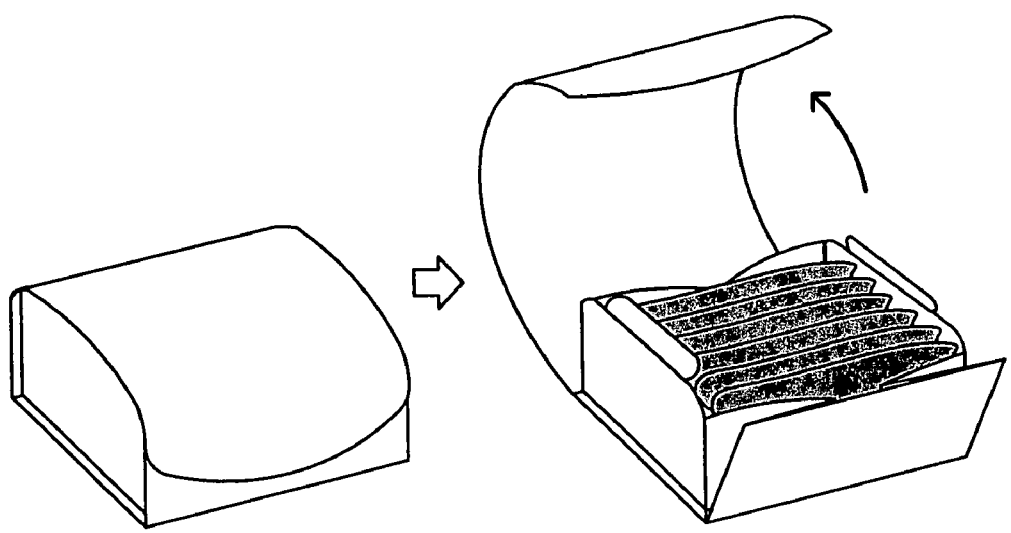
FIG. 54 illustrates the states of an outer package for packaging the interlabial pad individual wrapping containers before and after it is opened.
Figure 55:
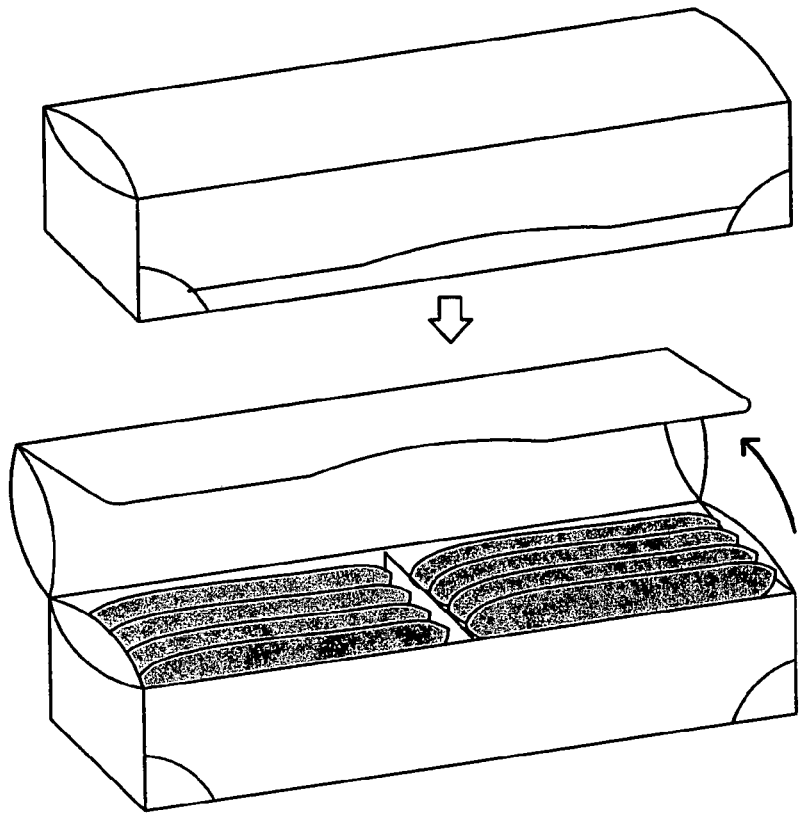
FIG. 55 illustrates the states of an outer package for packaging the interlabial pad individual wrapping containers before and after it is opened.
Figure 56:
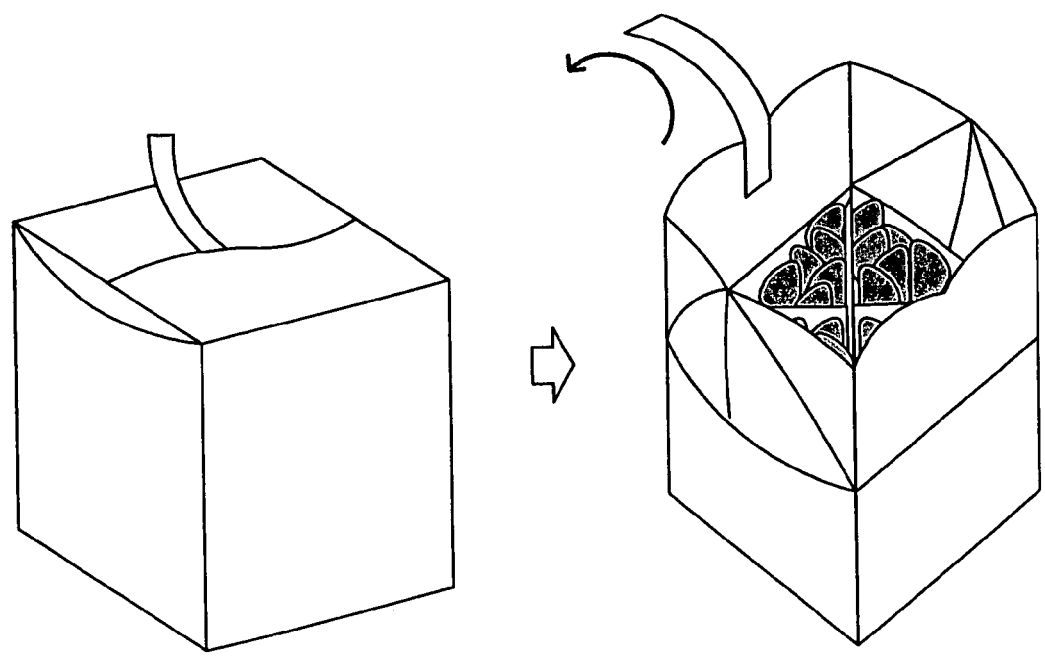
FIG. 56 illustrates the states of an outer package for packaging the interlabial pad individual wrapping containers before and after it is opened.

Moreover, as a method for printing the usage on the individual wrapping container, it is preferable to print it in the neighborhood of the pre-opening part for unsealing the individual wrapping container in order to prevent wearers from overlooking the printed part. Specifically, as shown in FIG. 50, numbers and symbols are used for inducing a sight line of a wearer so that the wearer is able to sequentially follow the usage according to the actions in which the wearer unfolds the folded wrapping sheet 190 and unseals the wrapping container 191. Moreover, the usage can be printed using pictures and sentences according to such numbers and symbols, however, only patterns may be used for the printing. Moreover, it is preferable to print the sentences in the direction orthogonal to the opening direction. When the description of the usage is printed directly on the individual wrapping container so as to be faced to the front of the wearer, such a troublesome action can be omitted, as the description has to be thrown away every time a wearer uses the interlabial pad, compared with the case in which the description is provided separately, and the fitting is more simplified.

As a method for enclosing the description in the outer package, it is especially preferable that a box type outer package formed from a carton or a thermoplastic resin is provided with an entrance on the top for taking out the interlabial pad so that the description can be taken out immediately when such an entrance is opened.

Moreover, it is also possible to stick the description on the top side (surface) or on the back side (inner surface) of the outer package, and to directly print the explanatory sentences and drawings on the top surface or on the inner surface of the outer package, or on the front face (especially, front upper face). In such a manner, it becomes possible to let a wearer visually check the explanatory sentences and drawings every time she takes out the interlabial pad individual wrapping body from the outer package.

As an outer package, various shapes can be adopted from the view points such as wearers' preference and ease of use, easiness for the manufacturing process, and superiority and inferiority of the distribution. For example, using the outer packages as shown in FIG. 51 through FIG. 56, the individual wrapping containers can be enclosed therein.

Figure 57:
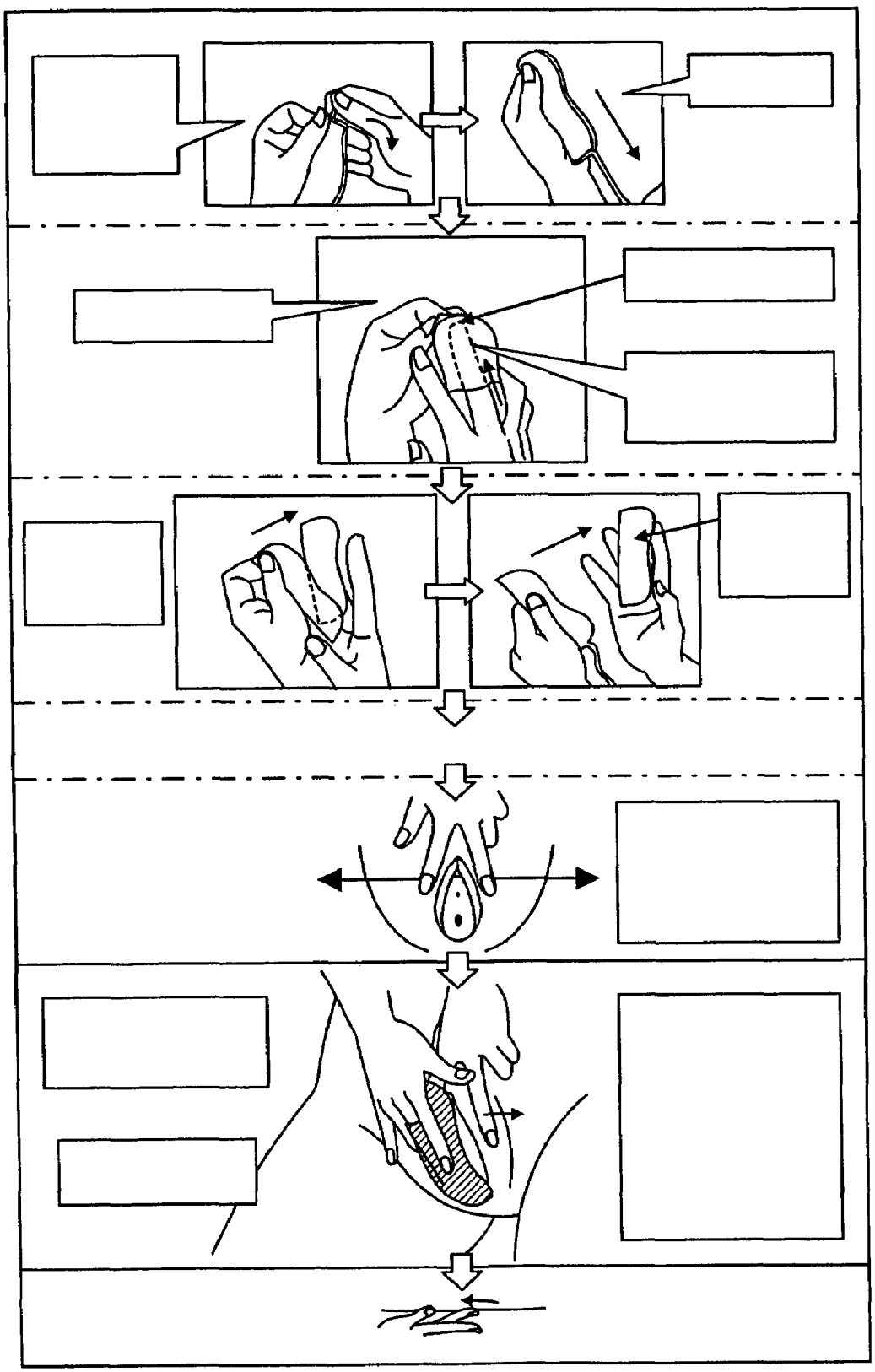
FIG. 57 is an explanatory drawing showing a method for fixing the interlabial pad.

Moreover, as an example of the description to be provided on the individual wrapping containers and the outer package, a combination of photographs and the explanatory sentences corresponding thereto can be mentioned as shown in FIG. 57.

INDUSTRIAL APPLICABILITY

As explained above, according to an embodiment of the present invention, when a wearer fixes or unfixes the interlabial pad, the wearer can makes use of the interlabial wrapping container, Therefore, it is possible for the wearer to perform such actions while preventing her fingers from coming in contact with the labia, without complicating the fixing and unfixing actions.

Moreover, since the interlabial pad is enclosed in the interlabial pad individual wrapping container so that a finger can be inserted in the finger insertion opening of the interlabial pad immediately after the interlabial pad individual wrapping container is unsealed, the interlabial pad can be held on the fingertip quickly and smoothly, and the fixing and unfixing actions of the interlabial pad can also be performed quicker.

What is claimed is:

1. A wrapping container which wraps an interlabial pad comprising:

a pad having an elongated shape;

a liquid permeable surface sheet having a body faceable side and an opposite side;

a liquid impermeable back sheet having a body faceable side and an opposite side;

an absorbent body in between the surface sheet and the back sheet; and a belt-like mini sheet piece directly affixed to the opposite side of the back sheet along first opposing edges thereof which are opposed along a first transverse direction of the backsheet and pad and unattached along second opposing edges which are opposed along a second direction that is transverse to the first direction to provide an opening in combination with the opposite side of the back sheet for inserting and passing a finger therethrough in order to remove the pad from a wrapping container with one hand and insert and remove the pad from a wearer, and the wrapping container having;

a wrapping sheet for enclosing the pad having an interior surface and an exterior surface;

a broken line defining perforations disposed on the wrapping sheet for completely separating or dividing separable sections of the wrapping container into two separate sections; and finger insertion portions formed by two mini sheet pieces that are directly attached to the exterior surface of the two separable sections of the wrapping container, respectively;

wherein each of the two mini sheet pieces is attached to one of the two separable sections along first opposing edges of the mini sheet which first opposing edges are opposed along a first direction that is transverse to the broken line, each of the two mini sheet pieces is unattached along second opposing edges of the mini sheet, which second opposing edges are opposed along a second direction that is parallel to the broken line to provide an opening in combination with the exterior surface of the one separable section for inserting and passing a respective finger therethrough to mount the container on the opposite hand and once the fingers are inserted permit the fingers to move apart along the first direction to separate and divide the container into two separate sections so that the labia of the wearer can be opened by the fingers holding the separate sections and the wearer can fix the interlabial pad removed from the container and held on the finger of the one hand in the labia in such a way as the fingers of the other hand never come in contact with the labia or menstrual blood;

wherein the body faceable side of the surface sheet of the interlabial pad when contained being in contact with the broken line of the wrapping sheet before the wrapping container is divided and separated and facing a portion of the sheet which includes the finger insertion portions and the outer side of the back sheet of the interlabial pad with the directly affixed belt-like mini sheet piece being on a side of the interlabial pad opposite to the body faceable side of the surface sheet so as to face away from the broken line of the wrapping sheet.

2. The wrapping container and interlabial pad of claim 1, wherein the wrapping sheet comprises a laminate material having a fiber sheet on the interior surface, and a film sheet on the extierior surface.

3. The wrapping container and interlabial pad of claim 1, wherein the wrapping sheet comprises a biodegradable material and/or a water-soluble material and/or a water dispersible material.

4. The wrapping container and interlabial pad according to claim 1, wherein one of the two mini sheet pieces on one of the two separable sections and the other of the two mini sheet pieces on the other of the two separable sections are attached at equal and opposing distances from the broken line.

* * * * *